United States Patent
Alvaro et al.

(10) Patent No.: US 7,855,218 B2
(45) Date of Patent: *Dec. 21, 2010

(54) COMPOUNDS

(75) Inventors: Giuseppe Alvaro, Verona (IT); Daniele Andreotti, Verona (IT); Markus Bergauer, Verona (IT); Riccardo Giovannini, Verona (IT); Agostino Marasco, Verona (IT)

(73) Assignee: Convergence Pharmaceuticals Limited, London (GB)

( * ) Notice: Subject to any disclaimer, the term of this patent is extended or adjusted under 35 U.S.C. 154(b) by 39 days.

This patent is subject to a terminal disclaimer.

(21) Appl. No.: 11/570,556

(22) PCT Filed: Oct. 6, 2006

(86) PCT No.: PCT/EP2006/009746

§ 371 (c)(1), (2), (4) Date: Jul. 19, 2008

(87) PCT Pub. No.: WO2007/042250

PCT Pub. Date: Apr. 19, 2007

(65) Prior Publication Data

US 2008/0306122 A1 Dec. 11, 2008

(30) Foreign Application Priority Data

| Oct. 10, 2005 | (GB) | .................. 0520561.2 |
| Nov. 11, 2005 | (GB) | .................. 0523028.9 |
| Feb. 27, 2006 | (GB) | .................. 0603899.6 |
| Sep. 18, 2006 | (GB) | .................. 0618336.2 |

(51) Int. Cl.
*A61K 31/454* (2006.01)
*A61K 31/40* (2006.01)
*C07D 401/02* (2006.01)
*C07D 207/00* (2006.01)

(52) U.S. Cl. .................. 514/326; 514/422; 548/409; 546/276.4

(58) Field of Classification Search .............. 514/326, 514/422; 546/276.4; 548/409
See application file for complete search history.

(56) References Cited

U.S. PATENT DOCUMENTS

| 5,236,957 | A | 8/1993 | Dostert et al. |
| 6,201,016 | B1 | 3/2001 | Cai et al. |
| 6,306,903 | B1 | 10/2001 | Pevarello et al. |
| 6,951,861 | B1 | 10/2005 | Alvaro et al. |
| 2004/0097578 | A1 | 5/2004 | Jolidon et al. |
| 2004/0235752 | A1 | 11/2004 | Pitt et al. |
| 2005/0234065 | A1 | 10/2005 | Hulin et al. |
| 2008/0269208 | A1 | 10/2008 | Alvaro et al. |
| 2008/0293753 | A1 | 11/2008 | Alvaro et al. |

| 2008/0306122 | A1 | 12/2008 | Alvaro et al. |

FOREIGN PATENT DOCUMENTS

| WO | 00/57877 | 10/2000 |
| WO | 2004/083189 | 9/2004 |
| WO | 2004/092140 | 10/2004 |
| WO | 2004/094395 | 11/2004 |
| WO | 2005/000309 | 1/2005 |
| WO | 2005/040108 A1 | 5/2005 |
| WO | 2006/119390 A1 | 11/2006 |
| WO | 2006/119451 A1 | 11/2006 |
| WO | 2006/124865 A2 | 11/2006 |
| WO | 2008/090114 A1 | 7/2008 |
| WO | 2008/090115 A1 | 7/2008 |
| WO | 2008/090116 A1 | 7/2008 |
| WO | 2008/090117 A1 | 7/2008 |
| WO | 2008090114 A1 | 7/2008 |
| WO | 2008090115 A1 | 7/2008 |
| WO | 2008090116 A1 | 7/2008 |
| WO | 2008090117 A1 | 7/2008 |
| WO | 2008/122546 A1 | 10/2008 |
| WO | 2008122546 A1 | 10/2008 |

OTHER PUBLICATIONS

Morissette et al. Advanced Drug Delivery Reviews 2004, 56, 275-300.*
Vippagunta, Sudha R. "Crystalline Solids." Advanced Drug Delivery Reviews 48(2001): 3-26.*
Wolff; Burger's Medicinal Chemistry, 5th Ed., Part 1; 1995; pp. 975-977; John Wiley & Sons.
Gavezzotti et al.; "Are Crystal Structures Predictable?"; Accounts of Chemical Research; 1994; vol. 27; pp. 309-314.
Banker et al.; Modern Pharmaceutics, 3rd Ed.; 1996; pp. 451 and 596; Marcel Dekker.

(Continued)

*Primary Examiner*—Kamal A Saeed
*Assistant Examiner*—Samantha L Shterengarts
(74) *Attorney, Agent, or Firm*—Amy H. Fix; Womble Carlyle Sandridge & Rice, PLLC

(57) ABSTRACT

Compounds of formula (I) wherein the variables are defined herein, pharmaceutical compositions thereof and methods for treatment using the same.

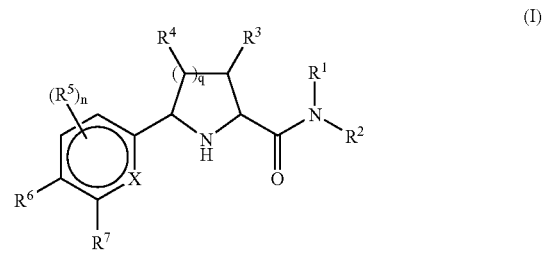

16 Claims, No Drawings

OTHER PUBLICATIONS

Shao et al.; "Phenoxyphenyl Pyridines as Novel State-Dependent, High-Potency Sodium Channel Inhibitors"; Journal of Medicinal Chemistry; 2004; vol. 47, No. 17; pp. 4277-4285.
Wolff; Burger's Medicinal Chemistry, 5th Ed., Part 1; 1995; pp. 975-977; John Wiley & Sons;.

Gavezzotti et al; "Are Crystal Structures Predictable?"; Accounts of Chemical Research; 1994; vol. 27; pp. 309-314; .
Banker et al.; Modern Pharmaceutics, 3rd Ed.; 1996; pp. 451 and 596; Marcel Dekker;.

* cited by examiner

COMPOUNDS

This application is filed pursuant to 35 U.S.C. §371 as a United States National Phase Application of International Patent Application Serial No. PCT/EP2006/009746 Filed Oct. 6, 2006, which claims priority from Great Britain Application No. 0520561.2 Filed in the United Kingdom on Oct. 10, 2005, Great Britain Application No. 0523028.9 filed in the United Kingdom on Nov. 11, 2005. Great Britain Application No. 0603899.6 filed in the United Kingdom on Feb. 27, 2006, and Great Britain Application No. 0618336.2 filed in the United Kingdom on Sep. 18, 2006, the Content of each of which is incorporated herein by reference.

The present invention relates to α-aminocarboxyamide derivatives, salts and prodrugs thereof, and to the use of these derivatives, salts and prodrugs thereof in treating diseases and conditions mediated by modulation of use-dependent voltage-gated sodium channels. In addition, the invention relates to compositions containing these derivatives, salts and prodrugs thereof, and processes for their preparation.

Voltage-gated sodium channels are responsible for the initial phase of the action potential, which is a wave of electrical depolarisation usually initiated at the soma of the neuron and propagated along the nerve axon to the terminals. At the terminals, the action potential triggers the influx of calcium and the release of neurotransmitter. Drugs, such as lidocaine, that block voltage-gated sodium channels are used as local anaesthetics. Other sodium channel blockers, such as lamotrigine and carbamazepine are used to treat epilepsy. In the latter case, partial inhibition of voltage-gated sodium channels reduces neuronal excitability and reduces seizure propagation. In the case of local anaesthetics, regional block of sodium channels on sensory neurons prevents the conduction of painful stimuli. A key feature of these drugs is their use-dependent mechanism of action. The drugs are thought to stabilise an inactivated configuration of the channel that is adopted rapidly after the channel opens. This inactivated state provides a refractory period before the channel returns to its resting (closed) state ready to be reactivated. As a result, use-dependent sodium channel blockers retard the firing of neurons at high frequency, for example in response to painful stimuli, and will help to prevent repetitive firing during periods of prolonged neuronal depolarisation that might occur, for example, during a seizure. Action potentials triggered at low frequencies, for example in the heart, will not be significantly affected by these drugs, although the safety margin differs in each case, since at high enough concentrations each of these drugs is capable of blocking the resting or open states of the channels.

The voltage-gated sodium channel family is made up of 10 subtypes, four of which are brain specific, NaV1.1, 1.2, 1.3 and 1.6. Of the other subtypes, NaV1.4 is found only in skeletal muscle, NaV1.5 is specific to cardiac muscle, and NaV1.7, 1.8, and 1.9 are found predominantly in sensory neurons. The hypothesised binding site for use-dependent sodium channel blockers is highly conserved between all the subtypes. As a result, drugs such as lidocaine, lamotrigine and carbamazepine do not distinguish between the subtypes. However, selectivity can be achieved as a result of the different frequencies at which the channels normally operate.

Drugs that block voltage-gated sodium channels in a use-dependent manner are also used in the treatment of bipolar disorder, either to reduce symptoms of mania or depression, or as mood stabilisers to prevent the emergence of mood episodes. Clinical and preclinical evidence also suggests that use-dependent sodium channel blockers may help to reduce the symptoms of schizophrenia. For example, lamotrigine has been shown to reduce symptoms of psychosis induced by ketamine in healthy human volunteers, and furthermore, studies in patients suggest that the drug can augment the antipsychotic efficacy of some atypical antipsychotic drugs, such as clozapine or olanzapine. It is hypothesised that efficacy in these psychiatric disorders may result in part from a reduction of excessive glutamate release. The reduction in glutamate release is thought to be a consequence of use-dependent sodium channel inhibition in key brain areas, such as the frontal cortex. However, interaction with voltage-gated calcium channels may also contribute to the efficacy of these drugs.

International published patent application WO05/000309 (Ionix Pharmaceuticals Limited) discloses the use of compounds of formula (I), wherein $R_1$ is an organic substituent, $X_1$ and $X_2$ are direct bonds or spacer moieties, Ar is aryl or heteroaryl and Y is a substituted aminoalkyl group or a heteroaryl-, heterocyclyl- or phenyl-containing moiety:

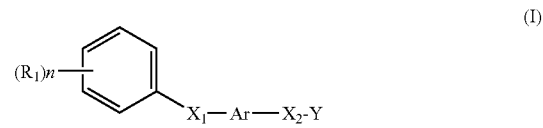

(I)

Such compounds are inhibitors of sensory neuron specific sodium channels and are said to be useful in the treatment of chronic and acute pain, tinnitus, bowel disorders, bladder dysfunction and demyelinating diseases.

International published patent application WO04/083189 (Merck & Co.) discloses biaryl substituted triazole compounds of formula (I), (II) and (III) as sodium channel blockers:

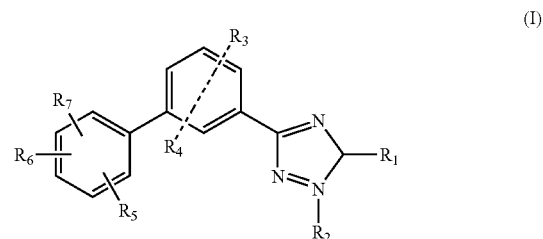

(I)

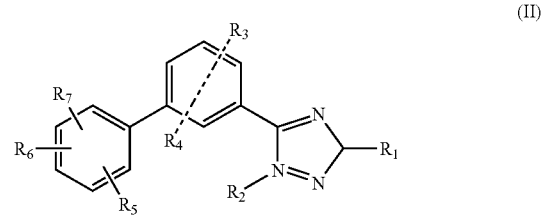

(II)

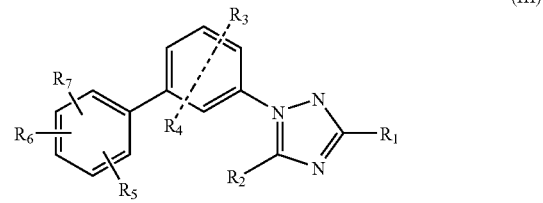

(III)

Such compounds are said to be useful in the treatment of conditions associated with sodium channel activity including, for example, acute pain, chronic pain, visceral pain, epilepsy, irritable bowel syndrome, depression and others.

International published patent application WO04/092140 (Merck & Co.) discloses biaryl substituted pyrazoles of formula (I), (II), (III) and (IV) as sodium channel blockers:

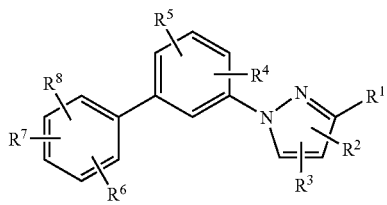
(I)

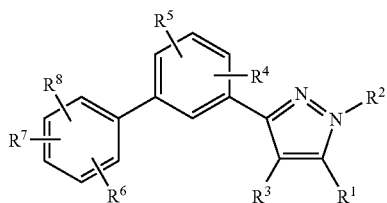
(II)

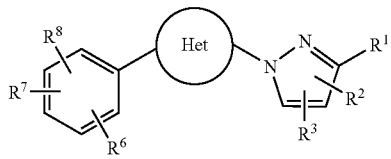
(III)

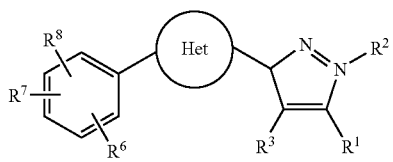
(IV)

The compounds are said to be useful in the treatment of conditions including acute pain, chronic pain, visceral pain, inflammatory pain and neuropathic pain.

International published patent application WO04/094395 (Merck & Co.) discloses biaryl substituted thiazoles, oxazoles and imidazoles of formula (I) as sodium channel blockers:

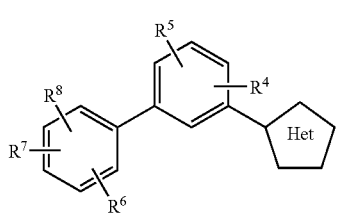
(I)

The compounds are said to be useful in the treatment of conditions including acute pain, chronic pain, visceral pain, inflammatory pain and neuropathic pain.

International patent application WO04/026826 (F. Hoffman La Roche A G) discloses 4-pyrrolidinophenyl-benzyl ether derivatives of formula (I):

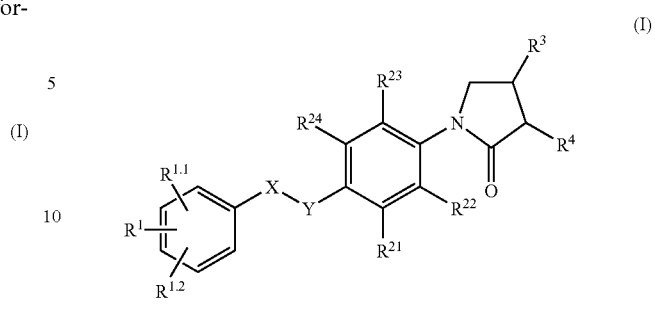
(I)

The compounds are said to be monoamine oxidase B inhibitors and are said to be useful in the treatment of conditions such as Alzheimer's disease or senile dementia.

The object of the present invention is to identify alternative compounds which modulate voltage-gated sodium channels.

In one embodiment, the compounds will be use dependent sodium channel inhibitors.

In another embodiment, the compounds will be a subtype NaV1.3 sodium channel use dependent inhibitors.

In another embodiment, the compounds will be use dependent sodium channel inhibitors which have a suitable developability profile on oral administration, for example in terms of exposure (Cmax) and/or bioavailability.

In another embodiment, the present invention provides compounds which modulate voltage-gated sodium channels and which additionally exhibit Monoamine Oxidase B inhibition.

In a still further embodiment, the present invention provides compounds which modulate voltage-gated sodium channels and which don't exhibit Monoamine Oxidase B inhibition.

According to a first aspect, the invention provides a compound of formula (I), a pharmaceutically acceptable salt, solvate or prodrug thereof

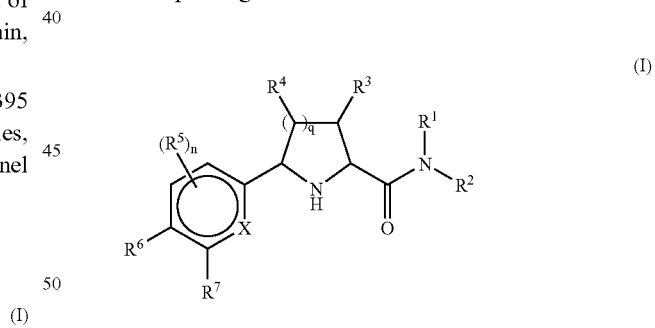
(I)

wherein $R^1$ and $R^2$ are independently hydrogen, $C_{1-6}$alkyl or $C_{3-6}$cycloalkyl$C_{1-6}$alkyl; or $R^1$ and $R^2$, together with the nitrogen to which they are attached, may form an unsubstituted 3-, 4-, 5- or 6-membered saturated ring;

q is 1 or 2;

$R^3$ and $R^4$ are hydrogen; or when q is 1, $R^3$ and $R^4$, together with the interconnecting atoms, may form a cyclopropane ring;

X is carbon or nitrogen;

n is 0, 1 or 2, wherein when present each $R^5$ is independently selected from the list consisting of $C_{1-3}$alkyl, halogen, cyano, halo$C_{1-3}$alkyl, hydroxy, $C_{1-3}$alkoxy and $C_{1-3}$haloalkoxy; and either R⁶ or R⁷ is —O—R⁸ or —OCH₂R⁸, wherein the other R⁶ or R⁷ is hydrogen or R⁵; and wherein R⁸ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

Unless otherwise indicated, any alkyl group is straight or branched regardless of whether it forms part of another group, for example, alkoxy, haloalkyl and haloalkoxy.

As used herein, a haloalkyl group means an alkyl group substituted by one or more halogen atoms. A haloalkoxy group should be similarly construed.

The term 5- or 6-membered aromatic heterocyclic ring means a heterocyclyl group containing one or more carbon atoms, one or more hydrogen atoms and one or more heteroatoms such as nitrogen, oxygen and sulfur; the carbon and heteroatoms being interconnected to form a ring. For example furyl, thienyl, pyrrolyl, imidazolyl, oxazolyl, thiazolyl, pyrazolyl, isoxazolyl, isothiazolyl, oxadiazolyl, triazolyl, thiadiazolyl, pyridyl, pyridazinyl, pyrimidinyl, pyrazinyl and tetrazolyl.

Halo means fluoro, chloro, bromo or iodo.

In a further embodiment the invention provides a compound of formula (I), a pharmaceutically acceptable salt, solvate or prodrug thereof

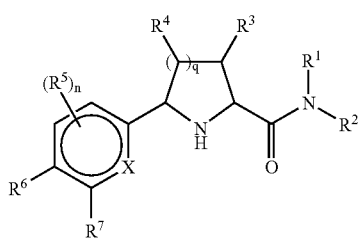

wherein
$R^1$ and $R^2$ are independently hydrogen, $C_{1-6}$alkyl or $C_{3-6}$cycloalkyl$C_{1-6}$alkyl; or $R^1$ and $R^2$, together with the nitrogen to which they are attached, may form an unsubstituted 3-, 4-, 5- or 6-membered saturated ring;
q is 1 or 2;
$R^3$ and $R^4$ are hydrogen; or when q is 1, $R^3$ and $R^4$, together with the interconnecting atoms, may form a cyclopropane ring;
X is carbon or nitrogen;
n is 0, 1 or 2, wherein when present each $R^5$ is independently selected from the list consisting of $C_{1-3}$alkyl, halogen, cyano, halo$C_{1-3}$alkyl, hydroxy, $C_{1-3}$alkoxy and $C_{1-3}$haloalkoxy; and
either $R^6$ or $R^7$ is —O—$R^8$ or —OCH₂$R^8$, wherein the other $R^6$ or $R^7$ is hydrogen or $R^5$; and wherein $R^8$ is a phenyl ring or wherein the phenyl ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

In a further embodiment the invention provides a compound of formula (I), a pharmaceutically acceptable salt, solvate or prodrug thereof

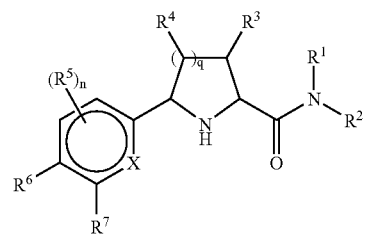

wherein
$R^1$ and $R^2$ are independently hydrogen, $C_{1-6}$alkyl or $C_{3-6}$cycloalkyl$C_{1-6}$alkyl; or such $R^1$ and $R^2$, together with the nitrogen to which they are attached, may form an unsubstituted 3-, 4-, 5- or 6-membered saturated ring;
q is 1 or 2;
$R^3$ and $R^4$ are hydrogen; or when q is 1, $R^3$ and $R^4$, together with the interconnecting atoms, may form a cyclopropane ring; or such $R^3$ and $R^1$, together with the interconnecting atoms may form a saturated or unsaturated 5- to 6-membered ring;
X is carbon or nitrogen;
n is 0, 1 or 2, wherein when present each $R^5$ is independently selected from the list consisting of $C_{1-3}$alkyl, halogen, cyano, halo$C_{1-3}$alkyl, hydroxy, $C_{1-3}$alkoxy and $C_{1-3}$haloalkoxy;
either $R^6$ or $R^7$ is —O—$R^8$, —OCHR⁹$R^8$, —NCH₂$R^8$ or —(CH₂)₂$R^8$ wherein the other $R^6$ or $R^7$ is hydrogen or $R^5$; and wherein $R^8$ is a phenyl ring or wherein the phenyl ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy; and
$R^9$ is hydrogen or $C_{1-3}$alkyl.

In an embodiment, X is carbon.
In another embodiment, X is nitrogen.
In an embodiment, q is 1. In another embodiment, q is 2.
In an embodiment, n is 0 or 1. In another embodiment n is 0.
In an embodiment, $R^1$ and $R^2$ are independently H or $C_{1-6}$alkyl. In an alternative embodiment, $R^1$ and $R^2$ are both H. In another embodiment $R^1$ and $R^2$ are independently H or $C_{1-3}$alkyl. In a further embodiment $R^1$ and $R^2$ are independently H or methyl.

In an embodiment, $R^3$ and $R^4$ are hydrogen. In another embodiment, $R^3$ and $R^1$, together with the interconnecting atoms may form a saturated or unsaturated 5-membered ring.

In an embodiment, n is 1 and $R^5$ is $C_{1-3}$alkoxy or cyano. In an alternative embodiment, n is 1 and $R^5$ is methoxy or cyano.

In an embodiment, $R^6$ is —O—$R^8$ or —OCH₂$R^8$, and $R^7$ is hydrogen or $R^5$; and wherein $R^8$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

In an embodiment, $R^6$ is —OCH₂$R^8$, and $R^7$ is hydrogen or $R^5$; and wherein $R^8$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

In another embodiment, $R^6$ is —OCH $R^9R^8$, —NCH$_2R^8$, —OR$^8$, or —(CH$_2$)$_2R^8$ and $R^7$ is hydrogen or $R^5$; and wherein $R^8$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

In an embodiment, $R^6$ is —OCH $R^9R^8$, and $R^7$ is hydrogen or $R^5$; and wherein $R^8$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

In a further embodiment, $R^6$ is —OR$^8$, and $R^7$ is hydrogen or $R^5$; and wherein $R^8$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

In a still further embodiment, $R^6$ is —NCH$_2R^8$, and $R^7$ is hydrogen or $R^5$; and wherein $R^8$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

In an additional further embodiment, $R^6$ is —(CH$_2$)$_2R^8$, and $R^7$ is hydrogen or $R^5$; and wherein $R^8$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

In another embodiment, $R^6$ is —O—$R^8$ or —OCH $R^9R^8$, and $R^7$ is hydrogen or $R^5$; and wherein $R^8$ is a phenyl ring optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

In a yet another embodiment, $R^6$ is —O—$R^8$ or —OCH $R^9R^8$, and $R^7$ is hydrogen or $R^5$; and wherein $R^8$ is either a phenyl ring optionally substituted by one group independently selected from the list consisting of $C_{1-3}$alkyl, halogen, cyano, halo$C_{1-3}$alkyl, hydroxy, $C_{1-3}$alkoxy and $C_{1-3}$haloalkoxy.

In a still further another embodiment, $R^6$ is —O—$R^8$ or —OCH $R^9R^8$, and $R^7$ is hydrogen or $R^5$; and wherein $R^8$ is either a phenyl ring optionally substituted in the ortho position by one group independently selected from the list consisting of $C_{1-3}$alkyl, halogen, cyano, halo$C_{1-3}$alkyl, hydroxy, $C_{1-3}$alkoxy and $C_{1-3}$haloalkoxy.

In a still further another embodiment, $R^6$ is —O—$R^8$ or —OCH $R^9R^8$, and $R^7$ is hydrogen or $R^5$; and wherein $R^8$ is either a phenyl ring optionally substituted in the meta position by one group independently selected from the list consisting of $C_{1-3}$alkyl, halogen, cyano, halo$C_{1-3}$alkyl, hydroxy, $C_{1-3}$alkoxy and $C_{1-3}$haloalkoxy.

In yet another embodiment, $R^5$ is —OCH$_2$-phenyl optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy. In yet another embodiment, $R^5$ is —OCH$_2$phenyl substituted by halogen, trifluoromethoxy or cyano.

In a further embodiment, $R^5$ is —OCH$_2$phenyl substituted by one fluorine atom.

In yet another embodiment, $R^5$ is —Ophenyl optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy. In yet another embodiment, $R^5$ is —Ophenyl substituted by halogen or cyano.

In another embodiment, $R^5$ is phenoxy, fluorophenoxy or cyanophenoxy. In a further embodiment $R^5$ is 2-cyano phenoxy, 4-cyano phenoxy, 3-fluorophenoxy or 4-fluorophenoxy.

In another embodiment, $R^5$ is benzyloxy, fluorobenzyloxy, trifluoromethylbenzyloxy or cyanobenzyloxy. In a further embodiment $R^5$ is 2-fluorobenzyloxy, 3-fluorobenzyloxy, 4-fluorobenzyloxy, 2-cyanobenzyloxy, 3-cyanobenzyloxy, 4-cyanobenzyloxy or 2-trifluoromethylbenzyloxy.

In an embodiment, $R^9$ is hydrogen or methyl. In another embodiment, $R^9$ is hydrogen.

In an embodiment, the compounds of formula (I) are selected from the list consisting of:

(2S,6R)-6-(4-{[(3-fluorophenyl)methyl]oxy}phenyl)-2-piperidinecarboxamide;
(2R,6S)-6-(4-{[(3-fluorophenyl)methyl]oxy}phenyl)-2-piperidinecarboxamide;
(5R)-5-{4-[(phenylmethyl)oxy]phenyl}-L-prolinamide;
(5R)-5-(4-{[(2-fluorophenyl)methyl]oxy}phenyl)-L-prolinamide;
5 (5R)-5-(4-{[(3-fluorophenyl)methyl]oxy}phenyl)-L-prolinamide;
(5R)-5-(4-{[(3-cyanophenyl)methyl]oxy}phenyl)-L-prolinamide;
(5R)-5-(4-{[(4-fluorophenyl)methyl]oxy}phenyl)-L-prolinamide;
(5R)-5-(4-{[(2-cyanophenyl)methyl]oxy}phenyl)-L-prolinamide;
(5R)-5-(4-{[(4-cyanophenyl)methyl]oxy}phenyl)-L-prolinamide;
(5R)-5-{4-[({2-[(trifluoromethyl)oxy]phenyl}methyl)oxy]phenyl}-L-prolinamide;
(5R)-5-(4-{[(1R)-1-phenylethyl]oxy}phenyl)-L-prolinamide;
(5R)-5-{4-[(4-fluorophenyl)oxy]phenyl}-L-prolinamide;
(5R)-5-{4-[(4-cyanophenyl)oxy]phenyl}-L-prolinamide;
(5R)-5-[4-(phenyloxy)phenyl]-L-prolinamide;
(5R)-5-{4-[(3-fluorophenyl)oxy]phenyl}-L-prolinamide;
(5R)-5-{4-[(2-cyanophenyl)oxy]phenyl}-L-prolinamide;
(5S)-5-{4-[(phenylmethyl)oxy]phenyl}-L-prolinamide;
(5S)-5-{4-({[(2-fluorophenyl)methyl]oxy}phenyl)-L-prolinamide;
(5S)-5-{4-[(phenylmethyl)oxy]phenyl}-D-prolinamide;
(5S)-5-(4-{[(2-fluorophenyl)methyl]oxy)phenyl}-D-prolinamide;
(5R)-5-(4-{[(2-fluorophenyl)methyl]oxy}phenyl)-D-prolinamide;
(5R)-5-(2-fluoro-4-{[(2-fluorophenyl)methyl]oxy}phenyl)-L-prolinamide; and
(5R)-5-{3-[(phenylmethyl)oxy]phenyl}-L-prolinamide;

or a pharmaceutically acceptable salt, solvate or prodrug thereof.

In another embodiment the compounds of formula (I) are selected from the list consisting of:

(2S,6R)-6-(4-{[(3-fluorophenyl)methyl]oxy}phenyl)-2-piperidinecarboxamide;
(2R,6S)-6-(4-{[(3-fluorophenyl)methyl]oxy}phenyl)-2-piperidinecarboxamide;
(5R)-5-(4-[(phenylmethyl)oxy]phenyl)-L-prolinamide;
(5R)-5-(4-{[(2-fluorophenyl)methyl]oxy}phenyl)-L-prolinamide;
(5R)-5-(4-{[(3-fluorophenyl)methyl]oxy}phenyl)-L-prolinamide;
(5R)-5-(4-{[(3-cyanophenyl)methyl]oxy}phenyl)-L-prolinamide;
(5R)-5-(4-{[(4-fluorophenyl)methyl]oxy}phenyl)-L-prolinamide;
(5R)-5-(4-{[(2-cyanophenyl)methyl]oxy}phenyl)-L-prolinamide;
(5R)-5-(4-{[(4-cyanophenyl)methyl]oxy}phenyl)-L-prolinamide;
(5R)-5-{4-[({2-[(trifluoromethyl)oxy]phenyl}methyl)oxy]phenyl}-L-prolinamide;
(5R)-5-(4-{[(1R)-1-phenylethyl]oxy}phenyl)-L-prolinamide;
(5R)-5-{4-[(4-fluorophenyl)oxy]phenyl}-L-prolinamide;
(5R)-5-{4-[(4-cyanophenyl)oxy]phenyl}-L-prolinamide;
(5R)-5-[4-(phenyloxy)phenyl]-L-prolinamide;
(5R)-5-{4-[(3-fluorophenyl)oxy]phenyl}-L-prolinamide;
(5R)-5-{4-[(2-cyanophenyl)oxy]phenyl}-L-prolinamide;
(5S)-5-{4-[(phenylmethyl)oxy]phenyl}-L-prolinamide;
(5S)-5-(4-{[(2-fluorophenyl)methyl]oxy}phenyl)-L-prolinamide;
(5S)-5-{4-[(phenylmethyl)oxy]phenyl}-D-prolinamide;
5-(4-{[(2-fluorophenyl)methyl]oxy}phenyl)-D-prolinamide;
5-(4-{[(2-fluorophenyl)methyl]oxy}phenyl)-D-prolinamide;
(5R)-5-(2-fluoro-4-{[(2-fluorophenyl)methyl]oxy)phenyl}-L-prolinamide;
(5R)-5-{3-[(phenylmethyl)oxy]phenyl}-L-prolinamide;
(5R)-5-[4-{([(2-fluorophenyl)methyl]oxy}-3-(methyloxy)phenyl]-L-prolinamide;
(5R)-5-(4-{[(2-fluorophenyl)methyl]amino}phenyl)-L-prolinamide;
(5R)-5-(3-cyano-4-{[(2-fluorophenyl)methyl]oxy}phenyl)-L-prolinamide;
(5R)-5-[4-(2-phenylethyl)phenyl]-L-prolinamide;
(5R)-5-(5-{[(2-fluorophenyl)methyl]oxy}-2-pyridinyl)-L-prolinamide;
(2S,3aS,6aS)-2-(4-{[(2-fluorophenyl)methyl]oxy}phenyl)hexahydropyrrolo[3,4-b]pyrrol-6(1H)-one;
(5R)-5-(4-{[(2-fluorophenyl)methyl]oxy}phenyl)-N-methyl-L-prolinamide;
(5R)-5-(4-{[(2-fluorophenyl)methyl]oxy}phenyl)-N,N-dimethyl-L-prolinamide;

or a pharmaceutically acceptable salt, solvate or prodrug thereof.

In another embodiment, the compounds of formula (I) are selected from the group consisting of hydrochloride salts, or solvates thereof, of the compounds listed below:

(2S,6R)-6-(4-{[(3-fluorophenyl)methyl]oxy}phenyl)-2-piperidinecarboxamide;
(2R,6S)-6-(4-{[(3-fluorophenyl)methyl]oxy}phenyl)-2-piperidinecarboxamide;
(5R)-5-{4-[(phenylmethyl)oxy]phenyl}-L-prolinamide;
(5R)-5-(4-{[(2-fluorophenyl)methyl]oxy)phenyl)-L-prolinamide;
(5R)-5-(4-([(3-fluorophenyl)methyl]oxy}phenyl)-L-prolinamide;
(5R)-5-(4-{[(3-cyanophenyl)methyl]oxy}phenyl)-L-prolinamide;
(5R)-5-(4-{[(4-fluorophenyl)methyl]oxy}phenyl)-L-prolinamide;
(5R)-5-(4-{[(2-cyanophenyl)methyl]oxy}phenyl)-L-prolinamide;
(5R)-5-(4-{[(4-cyanophenyl)methyl]oxy}phenyl)-L-prolinamide;
(5R)-5-{4-[({2-[(trifluoromethyl)oxy]phenyl}methyl)oxy]phenyl}-L-prolinamide;
(5R)-5-(4-{[(1R)-1-phenylethyl]oxy}phenyl)-L-prolinamide;
(5R)-5-{4-[(4-fluorophenyl)oxy]phenyl}-L-prolinamide;
(5R)-5-(4-[(4-cyanophenyl)oxy]phenyl)-L-prolinamide;
(5R)-5-[4-(phenyloxy)phenyl]-L-prolinamide;
(5R)-5-{4-[(3-fluorophenyl)oxy]phenyl}-L-prolinamide;
(5R)-5-{4-[(2-cyanophenyl)oxy]phenyl}-L-prolinamide;
(5S)-5-{4-[(phenylmethyl)oxy]phenyl}-L-prolinamide;
(5S)-5-(4-{[(2-fluorophenyl)methyl]oxy}phenyl)-L-prolinamide;
(5S)-5-{4-[(phenylmethyl)oxy]phenyl}-D-prolinamide;
5-(4-{[(2-fluorophenyl)methyl]oxy}phenyl)-D-prolinamide;
5-(4-{[(2-fluorophenyl)methyl]oxy}phenyl)-D-prolinamide;
(5R)-5-(2-fluoro-4-{[(2-fluorophenyl)methyl]oxy}phenyl)-L-prolinamide;
(5R)-5-{3-[(phenylmethyl)oxy]phenyl}-L-prolinamide;
(5R)-5-[4-{[(2-fluorophenyl)methyl]oxy}-3-(methyloxy)phenyl]-L-prolinamide;
(5R)-5-(4-{[(2-fluorophenyl)methyl]amino}phenyl)-L-prolinamide;
(5R)-5-(3-cyano-4-{[(2-fluorophenyl)methyl]oxy}phenyl)-L-prolinamide;
(5R)-5-[4-(2-phenylethyl)phenyl]-L-prolinamide;
(5R)-5-(5-{[(2-fluorophenyl)methyl]oxy}-2-pyridinyl)-L-prolinamide;
(2S,3aS,6aS)-2-(4-{[(2-fluorophenyl)methyl]oxy}phenyl)hexahydropyrrolo[3,4-b]pyrrol-6(1H)-one;
(5R)-5-(4-{[(2-fluorophenyl)methyl]oxy}phenyl)-N-methyl-L-prolinamide;
(5R)-5-(4-{[(2-fluorophenyl)methyl]oxy}phenyl)-N,N-dimethyl-L-prolinamide.

In a further embodiment the compound of formula (I) is selected from the list consisting of:

(5R)-5-(4-{[(2-fluorophenyl)methyl]oxy}phenyl)-L-prolinamide;
(5R)-5-[4-{[(2-fluorophenyl)methyl]oxy}-3-(methyloxy)phenyl]-L-prolinamide;
(5R)-5-(4-{[(2-fluorophenyl)methyl]amino}phenyl)-L-prolinamide;

or a pharmaceutically acceptable salt, solvate or prodrug thereof.

In another embodiment, the compounds of formula (I) are selected from the group consisting of hydrochloride salts, or solvates thereof, of the compounds listed below:

(5R)-5-(4-{[(2-fluorophenyl)methyl]oxy}phenyl)-L-prolinamide;
(5R)-5-[4-{[(2-fluorophenyl)methyl]oxy}-3-(methyloxy)phenyl]-L-prolinamide;
(5R)-5-(4-{[(2-fluorophenyl)methyl]amino}phenyl)-L-prolinamide.

In a further embodiment the compound of formula (I) is (5R)-5-(4-{[(2-fluorophenyl)methyl]oxy}phenyl)-L-prolinamide or a pharmaceutically acceptable salt, solvate or prodrug thereof.

In a further embodiment the compound of formula (I) is (5R)-5-(4-{[(2-fluorophenyl)methyl]oxy}phenyl)-L-prolinamide hydrochloride or a solvate thereof.

In a further embodiment the compound of formula (I) is selected from the list consisting of:
(2S,6R)-6-(4-{[(3-fluorophenyl)methyl]oxy}phenyl)-2-piperidinecarboxamide;
(2R,6S)-6-(4-{([(3-fluorophenyl)methyl]oxy}phenyl)-2-piperidinecarboxamide;
(5R)-5-(4-{[(1R)-1-phenylethyl]oxy}phenyl)-L-prolinamide;
(5R)-5-{4-[(4-fluorophenyl)oxy]phenyl}-L-prolinamide;
(5R)-5-{(4-[(4-cyanophenyl)oxy]phenyl}-L-prolinamide;
(5R)-5-[4-(phenyloxy)phenyl]-L-prolinamide;
(5R)-5-[4-{([(2-fluorophenyl)methyl]oxy}-3-(methyloxy) phenyl]-L-prolinamide;
(5R)-5-(4-{[(2-fluorophenyl)methyl]amino}phenyl)-L-prolinamide;
(5R)-5-(4-{[(2-fluorophenyl)methyl]oxy}phenyl)-N-methyl-L-prolinamide;
(5R)-5-(4-{[(2-fluorophenyl)methyl]oxy}phenyl)-N,N-dimethyl-L-prolinamide;

or a pharmaceutically acceptable salt, solvate or prodrug thereof.

In a further embodiment the compound of formula (I) is selected from the list consisting of:
(5R)-5-{4-[(phenylmethyl)oxy]phenyl}-L-prolinamide
(5R)-5-(4-{[(2-fluorophenyl)methyl]oxy}phenyl)-L-prolinamide;
(5R)-5-(4-{[(3-fluorophenyl)methyl]oxy}phenyl)-L-prolinamide;
(5R)-5-(4-{[(3-cyanophenyl)methyl]oxy}phenyl)-L-prolinamide;
(5R)-5-(4-{[(4-fluorophenyl)methyl]oxy}phenyl)-L-prolinamide;
(5R)-5-(4-{[(2-cyanophenyl)methyl]oxy}phenyl)-L-prolinamide;
(5R)-5-(4-{[(4-cyanophenyl)methyl]oxy}phenyl)-L-prolinamide;
(5R)-5-{4-[({2-[(trifluoromethyl)oxy]phenyl}methyl)oxy] phenyl}-L-prolinamide;
(5S)-5-(4-{[(2-fluorophenyl)methyl]oxy}phenyl)-L-prolinamide;
(5S)-5-{4-[(phenylmethyl)oxy]phenyl}-D-prolinamide;
5-(4-{[(2-fluorophenyl)methyl]oxy}phenyl)-D-prolinamide;
5-(4-{[(2-fluorophenyl)methyl]oxy}phenyl)-D-prolinamide;
(5R)-5-(3-cyano-4-{[(2-fluorophenyl)methyl]oxy}phenyl)-L-prolinamide;

or a pharmaceutically acceptable salt, solvate or prodrug thereof.

For the avoidance of doubt, unless otherwise indicated, the term "substituted" means substituted by one or more defined groups. In the case where groups may be selected from a number of alternative groups, the selected groups may be the same or different.

For the avoidance of doubt, the term "independently" means that where more than one substituent is selected from a number of possible substituents, those substituents may be the same or different.

The pharmaceutically or veterinarily acceptable salts of the compounds of formula (I) which contain a basic centre are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention.

Hereinafter, compounds and their pharmaceutically acceptable salts, solvates and prodrugs defined in any aspect of the invention (except intermediate compounds in chemical processes) are referred to as "compounds of the invention".

The pharmaceutically acceptable solvates of the compounds of the invention include the hydrates thereof.

Also included within the scope of the compound and various salts of the invention are polymorphs thereof.

The compounds of the invention may possess at least two or more chiral centres and so exist in a number of stereoisomeric forms. All stereoisomers and mixtures thereof are included in the scope of the present invention.

It will be appreciated by the person skilled in the art that at least four possible diastereoisomers may exist for compounds of formula (I), i.e. compounds of formula (Ia), (Ib), (Ic) and (Id). These are shown below:

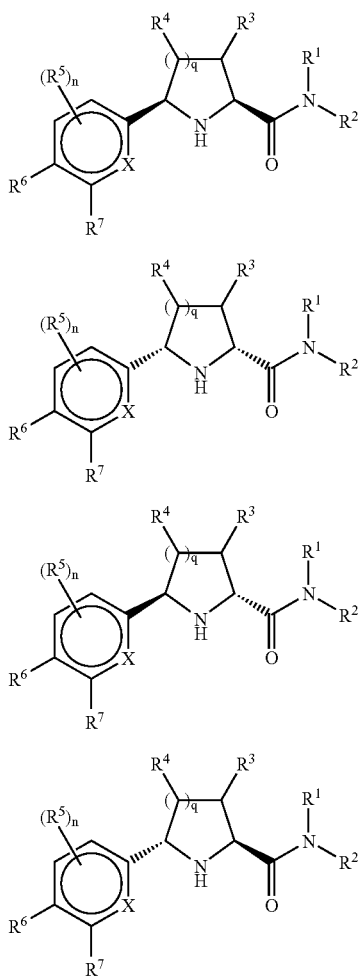

In one embodiment, the present invention provides compounds of formula (Ia)

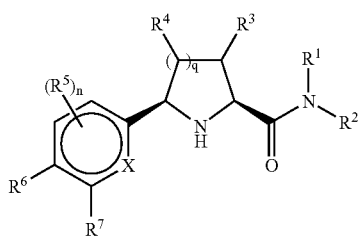

wherein $R^1$, $R^2$, $R^3$, $R^4$, $R^5$, $R^6$, $R^7$, X, n and q are as defined above, or pharmaceutically acceptable salts, solvates or prodrugs thereof.

Diastereoisomers of compounds of the invention may be obtained according to methods well known in the literature, for example by preparative HPLC or by chromatographic purifications. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of the invention.

The compounds of the invention may exist in one or more tautomeric forms. All tautomers and mixtures thereof are included in the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^2H$, $^3H$. $^{13}C$, $^{14}C$, $^{15}N$, $^{17}O$, $^{18}O$, $^{31}P$, $^{32}P$, $^{35}S$, $^{18}F$ and $^{36}Cl$ respectively. Certain isotopic variations of the invention, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples hereafter using appropriate isotopic variations of suitable reagents.

Compounds of the invention may be prepared in a variety of ways. In the following reaction schemes and hereafter, unless otherwise stated $R^1$ to $R^9$, X, n and q are as defined in the first aspect. These processes form further aspects of the invention.

Throughout the specification, general formulae are designated by Roman numerals (I), (II), (III), (IV) etc. Subsets of these general formulae are defined as (Ia), (Ib), (Ic) etc. . . . (IVa), (IVb), (IVc) etc.

Hydrochloride salts of compounds of formula (I) may be prepared according to Reaction Scheme 1 by reacting compounds of formula (II) with an excess (eg 2.5 eq) of acetyl chloride and methanol. Typical reaction conditions comprise reacting (II) in a suitable aprotic solvent (such as EtOAc) at room temperature.

Reaction Scheme 1

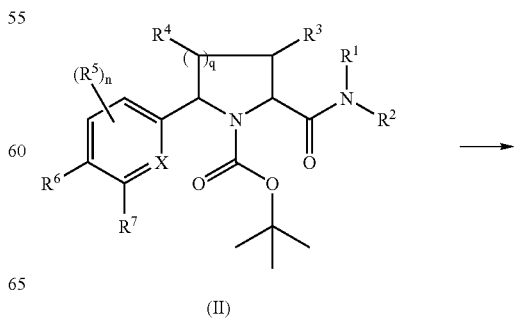

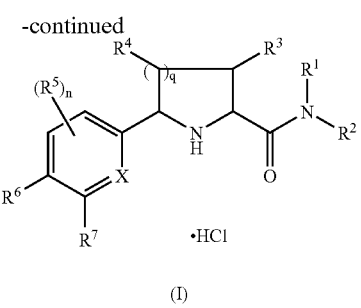

(I)

Compounds of formula (IIa), i.e. compounds of formula (II) where $R^6$ is —$OCH_2R^8$, can be prepared according to Reaction Scheme 2 by reacting compounds of formula (III) with an excess (eg 1.5 eq) of $R^8CH_2Y$ (where Y is a suitable leaving group—for examples see J. March, Advanced Organic Chemistry: reactions, mechanisms, and structure, John Wiley & Sons (1992), 4$^{th}$ Ed., p 352). Typical reaction conditions comprise reaction in a suitable solvent (such as acetonitrile or DMF) at a temperature ranging from room temperature to solvent reflux. It will be appreciated that compounds of formula (IIa) where $R^7$ is —$OCH_2R^8$, can be prepared by analogous methods starting from the hydroxy compound corresponding to compounds of formula (III). Compounds of formula $R^8CH_2Y$ are either commercially available or can be synthesized via methodologies widely known in the literature.

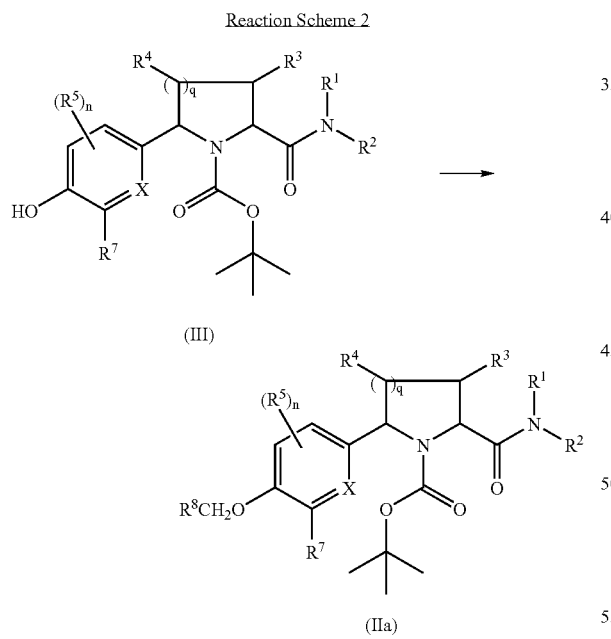

Compounds of formula (IIb), i.e. compounds of formula (II) where $R^6$ is —$OR^8$, may be prepared according to Reaction Scheme 3 by reacting compounds of formula (III) with $R^8$—$B(OH)_2$. Typical reaction conditions comprise treatment with a suitable catalyst (such as copper (II) acetate) and a suitable base (such as TEA, pyridine) in a halogenated hydrocarbon solvent (such as DCM) at a temperature ranging from room temperature to solvent reflux. Compounds of formula $R^8$—$B(OH)_2$ are either commercially available or may be synthesised via methodologies known in the literature.

Alternatively compounds of formula (IIb) where $R^8$ contains one or more electron withdrawing substituents, may be obtained according to Reaction Scheme 3 by reacting compounds of formula (III) with $R^8$—F in the presence of a suitable base (such as $K_2CO_3$) in an appropriate solvent (such as DMF) by heating with microwave irradiation.

Compounds of formula $R^8$—F are either commercially available or may be synthesised via methodologies known in the literature.

It will be appreciated that compounds of formula (II) where $R^7$ is —$OR^8$, may be prepared by analogous methods starting from the hydroxy compound corresponding to compound of formula (III).

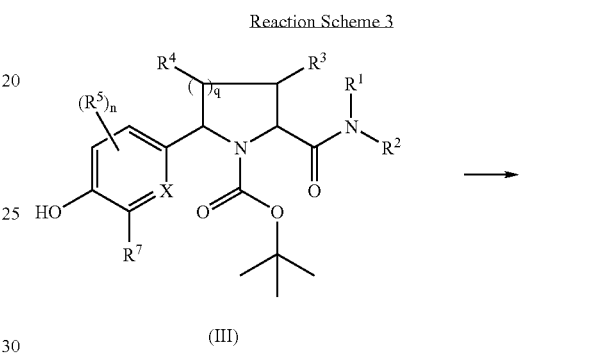

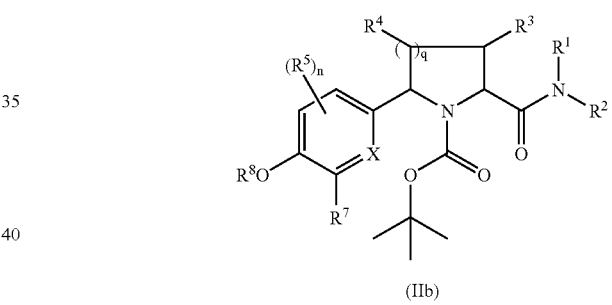

Compounds of formula (III) may be prepared according to Reaction Scheme 4 by reacting compounds of formula (IV) with palladium on carbon under a hydrogen atmosphere (such as 1 atm) in a suitable alcoholic solvent (such as methanol) at room temperature.

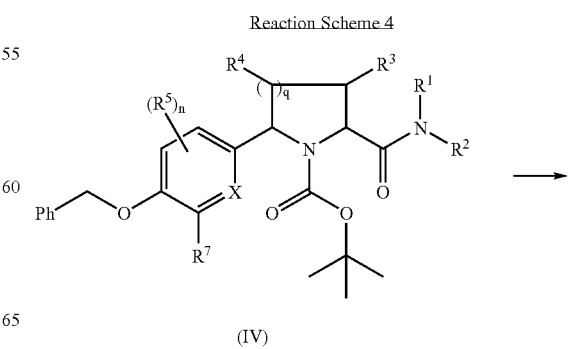

-continued

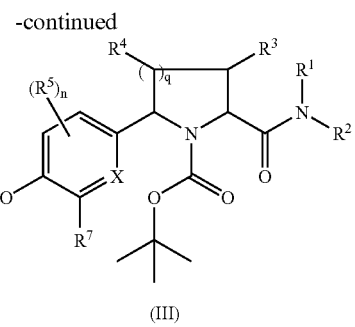

(III)

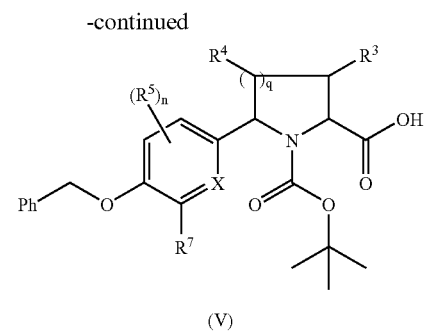

(V)

Compounds of formula (IV) may be obtained according to reaction Scheme 5 by reacting compounds of formula (V) with an amine of formula (VI) in the presence of an appropriate coupling agent (such as HATU or TBTU), a suitable base (such as TEA or DIPEA) in an aprotic solvent (such as DMF) at room temperature.

Compounds of formula (VII) can be prepared according to Reaction Scheme 7 by reacting compounds of formula (VIII), wherein R is a lower alkyl group, with a suitable base (such as LiOH) in a THF/water mixture (such as 1:1) at room temperature.

Reaction Scheme 5

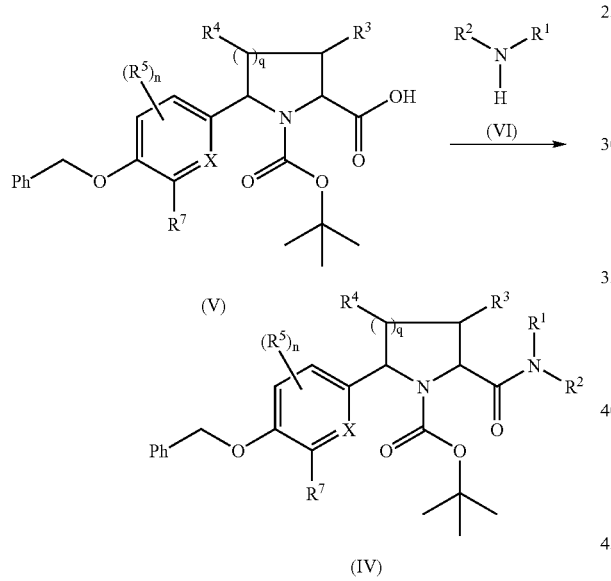

(IV)

Reaction Scheme 7

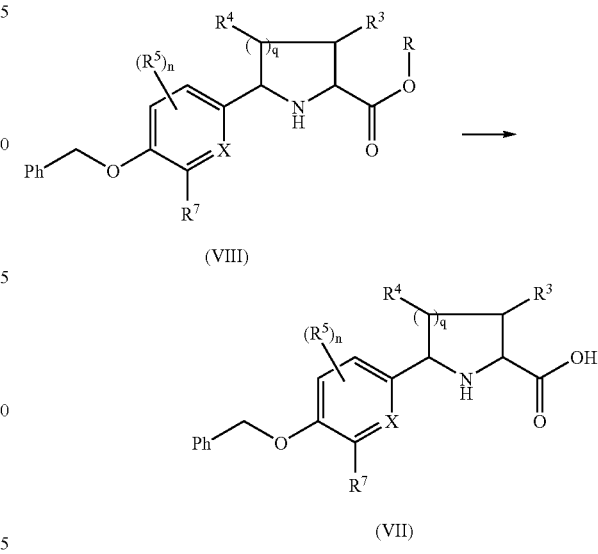

(VII)

Compounds of formula (V) may be prepared according to Reaction Scheme 6. Typical reaction conditions comprise reacting compounds of formula (VII) with a reagent suitable for introducing a BOC protecting group onto an amine (such as di-tert-butyl dicarbonate) in an aprotic solvent (such as THF) at room temperature.

Compounds of formula (VIII) can be prepared according to Reaction Scheme 8 by reacting compounds of formula (IX) with PtO$_2$ under an atmosphere of hydrogen at elevated pressure (such as 2 atm) in a suitable alcoholic solvent (such as methanol) at room temperature.

Reaction Scheme 6

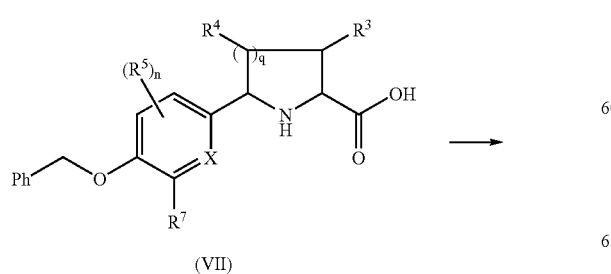

(VII)

Reaction Scheme 8

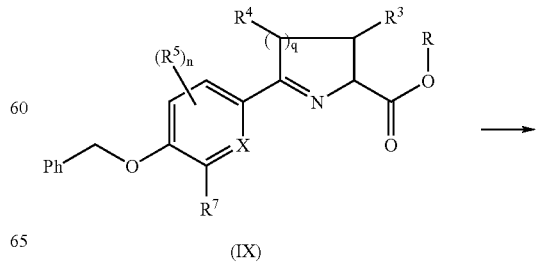

(IX)

-continued

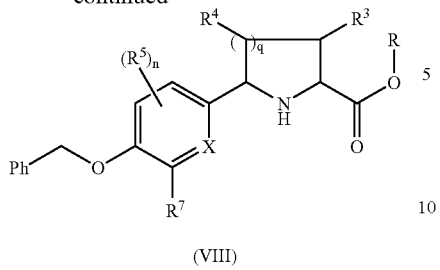

(VIII)

-continued

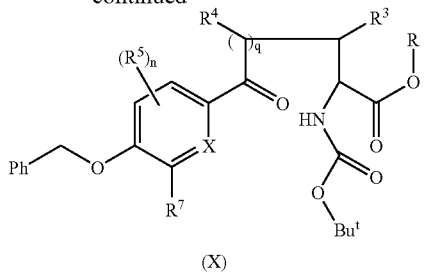

(X)

Compounds of formula (IX) may be prepared according to Reaction Scheme 9 by reacting compounds of formula (X) with trifluoroacetic acid in a halogenated hydrocarbon solvent (such as DCM) at low temperature (such as 0° C.).

The compounds of general formula (XIIa) where M is MgZ (where Z is Cl, Br or I) may be generated according to Reaction Scheme 11 via methodologies known in the literature by reacting the appropriate compound of general formula (XIII) with magnesium metal in ether. Typical reaction conditions comprise reaction at low temperature (ranging from −78° C. to 0° C.) in a suitable solvent (such as ether or THF).

Reaction Scheme 9

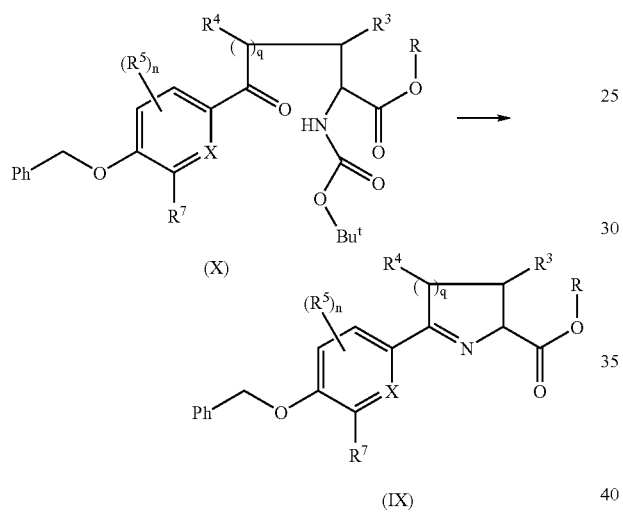

Reaction Scheme 11

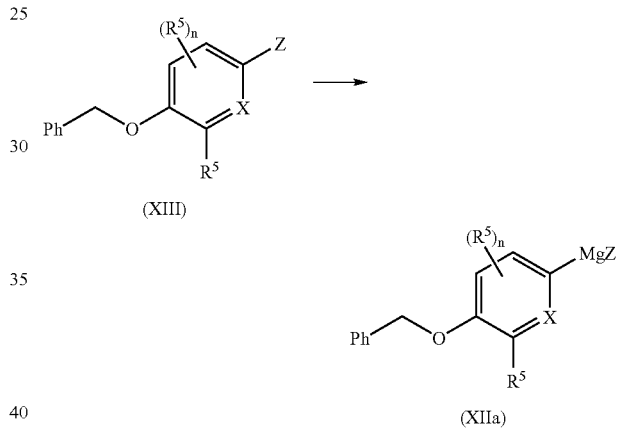

Compounds of formula (X) may be obtained according to Reaction Scheme 10. Typical reaction conditions comprise reacting compounds of formula (XI) with a suitable metallated compound of formula (XII) where M is for example MgZ (where Z is Cl, Br or I) or lithium in a suitable solvent (such as diethyl ether or THF) at low temperature (such as −78° C.).

Compounds of general formula (XIII) are either commercially available or may be synthesized following the procedures described in Reaction Scheme 12 by reacting compounds of formula (XIV) with benzyl bromide in the presence of a suitable base (such as potassium carbonate) in a suitable solvent (such as acetonitrile or DMF) at a temperature ranging from room temperature to reflux.

Reaction Scheme 10

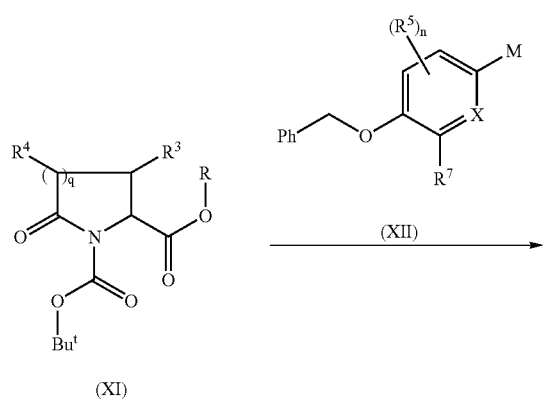

Reaction Scheme 12

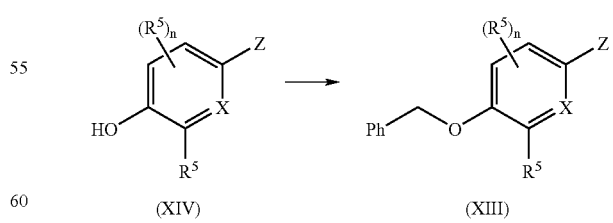

The compounds of formula (XIIb), i.e. compounds of general formula (XII) wherein M is lithium may be generated according to Reaction Scheme 13 via methodologies widely known in the literature by reacting the appropriate compound of general formula (XIII) with n-butyllithium. Typical reaction conditions comprise reaction at low temperature (ranging from −78° C. to 0° C.) in a suitable solvent (such as ether or THF).

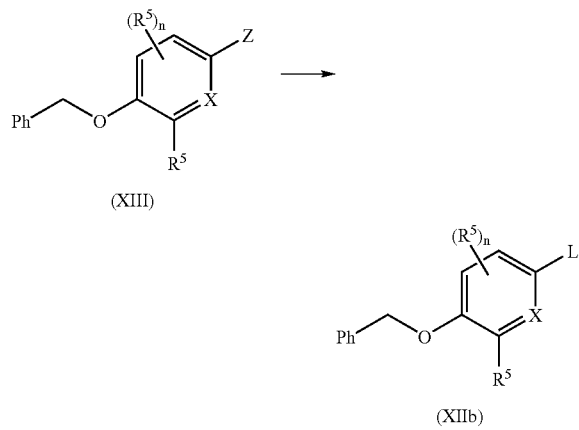

It will be appreciated that the reactions shown in Reaction Schemes 2 to 13 are applicable to the preparation of compounds of formula (I) where $R^7$ is —$OR^8$ or —$OCH_2R^8$ as appropriate.

Compounds of formula (XI) may be prepared according to Reaction Scheme 14 by reacting compounds of formula (XV) with a reagent suitable for introducing a BOC group onto an amine (i.e. di-tert-butyl dicarbonate) in the presence of a suitable base (such as 4-DMAP) in an aprotic solvent (such as DCM) at room temperature.

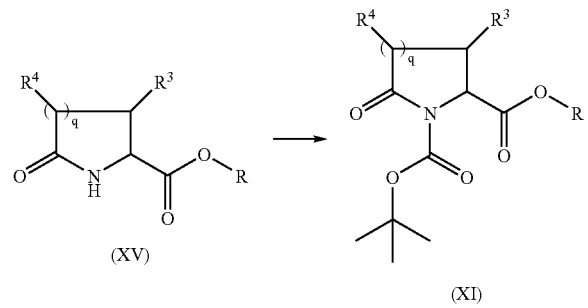

Compounds of general formula (XV) where q is 1 and $R^3$ and $R^4$ are hydrogen are commercially available.

Compounds of formula (XV) where q is 2 and $R^3$ and $R^4$ are hydrogen may be prepared using procedures similar to those described in S. Huang, J. Nelson, D. Weller, *Synthetic Communications*, Vol 19, No 20, 3485-96 (1989).

Compounds of formula (XV) where q is 1 and $R^3$ and $R^4$ together with the interconnecting atoms form a cyclopropane ring, may be prepared using procedures similar to those described in 1. Sagnard, N. Sasaki, A. Chiaroni, C. Riche, P. Potier, *Tetrahedron Letters*, 36, 3149-3152 (1995).

Compounds of formula (Ie), i.e. compounds of general formula (I) where q is 2 and $R^3$ and $R^4$ are hydrogen, may be prepared according to Reaction Scheme 15, by reacting compounds of formula (XVI) with $PtO_2$ under a hydrogen atmosphere at elevated pressure (such as 4 atmos) in acetic acid as solvent at room temperature.

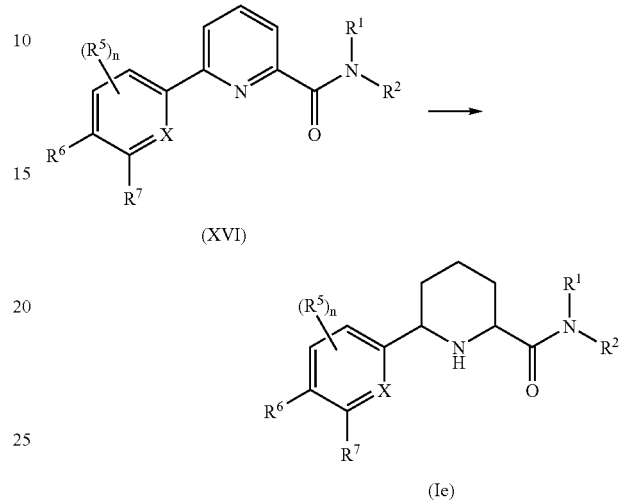

Compounds of formula (XVI) may be prepared according to Reaction Scheme 16 from compounds of formula (XVII) where R is a lower alkyl group. Typical reaction conditions are analogous to those described for Reaction Scheme 5. Alternatively, where $R^1$ and $R^2$ are both hydrogen, typical reaction conditions comprise reacting compounds of formula (XVII) with ammonia in methanol at a temperature ranging from room temperature to solvent reflux.

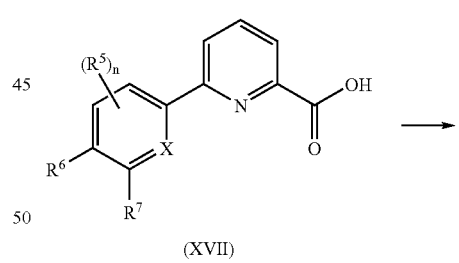

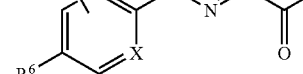

Compounds of formula (XVII) may be prepared according to Reaction Scheme 17 from compounds of formula (XVIII), where R is lower alkyl. Typical conditions are as described for Reaction Scheme 7.

Reaction Scheme 17

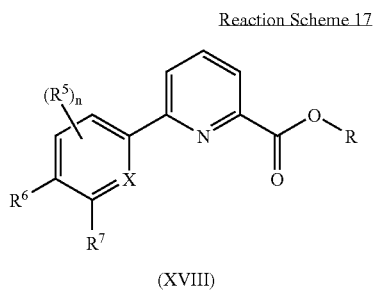

Compounds of formula (XVIII) may be prepared according to Reaction Scheme 18 from compounds of formula (XIX) and (XX). A typical procedure comprises reacting compounds of general formula (XIX) where Hal is Cl, Br or I with compounds of formula (XX) in the presence of a suitable palladium catalyst (such as Pd(PPh$_3$)$_4$). For examples of palladium catalyzed coupling protocols see Eiichi Negishi, Handbook of Organopalladium Chemistry for Organic Synthesis, John Wiley & Sons, 2002.

Reaction Scheme 18

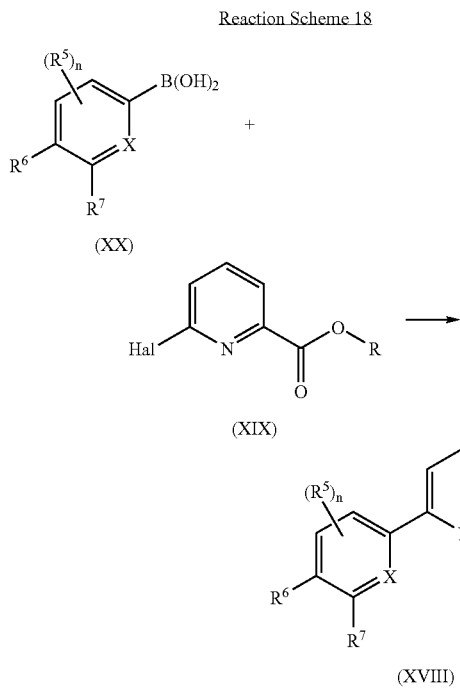

Compounds of general formula (XX) are either commercially available or may be prepared by procedures known to the skilled person.

Alternatively, hydrochloride salts of compounds of formula (Ih), i.e. compounds of formula (I) wherein $R^1$ and $R^2$ are hydrogen and $R^6$ or $R^7$ is —OCH$_2$R$^8$, may be prepared according to Reaction Scheme 19 by reacting compounds of formula (XXI) with hydrogen chloride solution in diethyl ether at low temperature (such as 0° C.).

Reaction Scheme 19

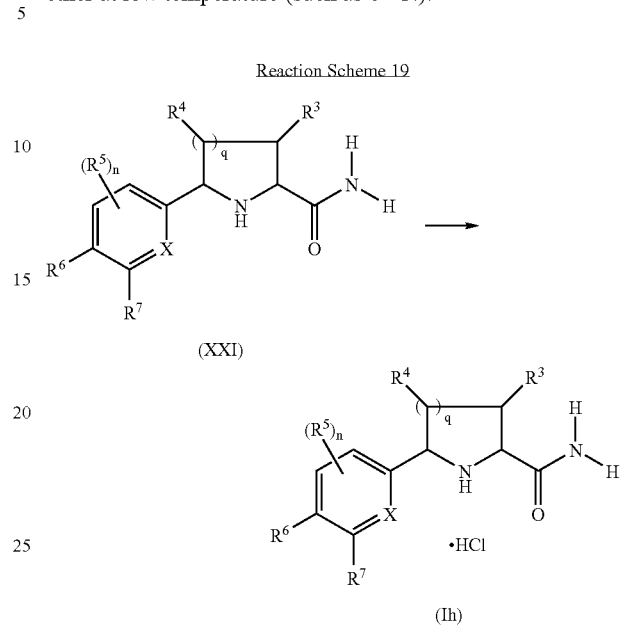

Compounds of formula (XXI) may be obtained according to Reaction Scheme 20 by treating compounds of formula (XXII), wherein R is a lower alkyl group, with a solution of NH$_3$ solution (for example a concentrated solution, such as 7N or 11.2 M solution) in an appropriate solvent (such as methanol) and at the appropriate temperature (for example room temperature).

Reaction Scheme 20

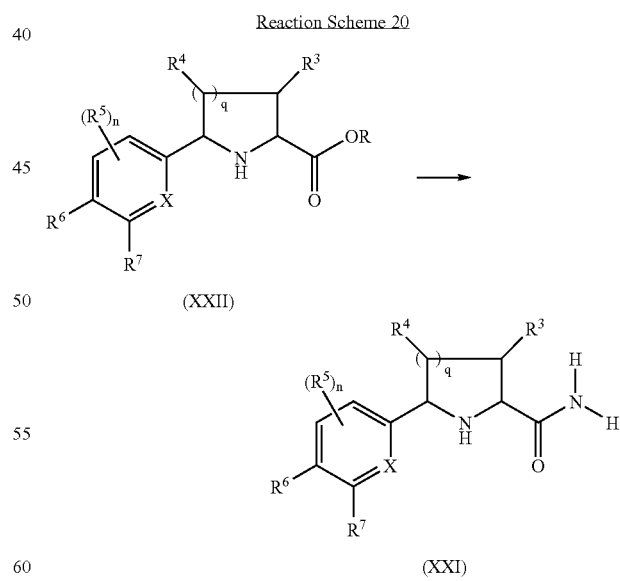

Compounds of formula (XXII) can be prepared according to Reaction Scheme 21 by reacting compounds of formula (XXIII) with Pt/C under an atmosphere of hydrogen at elevated pressure (such as 2 atm) in a suitable solvent (such as AcOEt) at room temperature.

Reaction Scheme 21

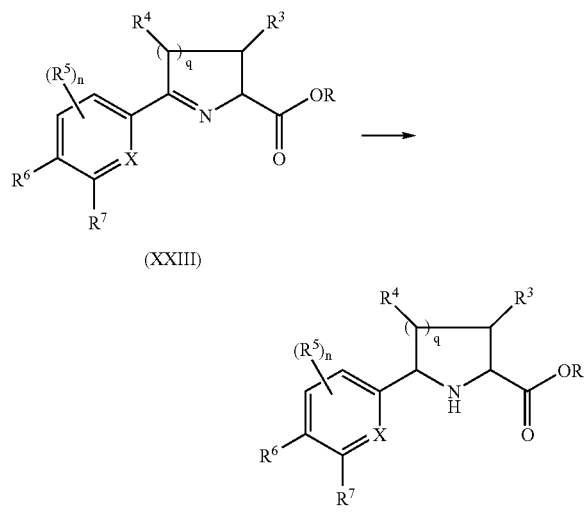

Compounds of formula (XXIII) may be prepared according to Reaction Scheme 22 by reacting compounds of formula (XXIV) with trifluoroacetic acid in a halogenated hydrocarbon solvent (such as DCM) at a temperature ranging from 0° C. to room temperature.

As an alternative compounds of formula (XXIII) with q=1 and R³=R⁴=H may be prepared from compounds of formula (XLIV) using a metal catalyst such as silver-(I)-triflate in dipolar aprotic solvents (such as N,N-dimethylformamide, tetrahydrofuran or acetonitrile) at temperatures ranging from 0 degrees to reflux. Compounds of formula (XLIV) are readily prepared by analogous procedures to that described in the literature (van Esseveldt et al, Journal of Organic Chemistry 2005, 70, 1791-1795 and references cited therein).

Reaction Scheme 22

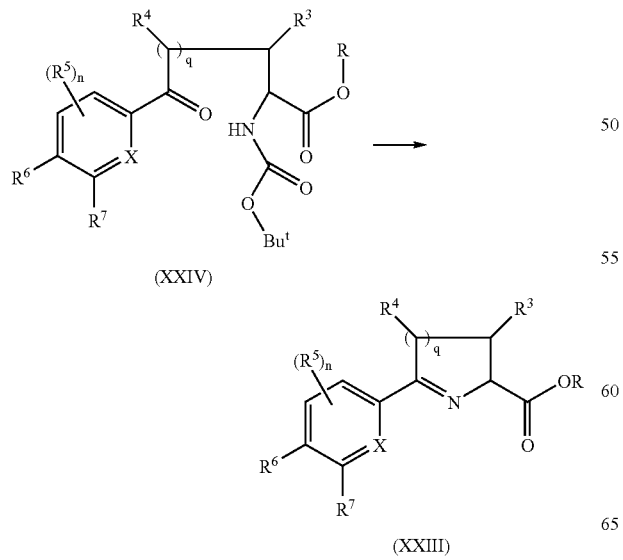

Compounds of formula (XXIV) may be obtained according to Reaction Scheme 23. Typical reaction conditions comprise reacting compounds of formula (XI) with a suitable metallated compound of formula (XXV) where Z is Cl, Br or I in a suitable solvent (such as diethyl ether or THF) at low temperature (such as −60° C.).

Reaction Scheme 23

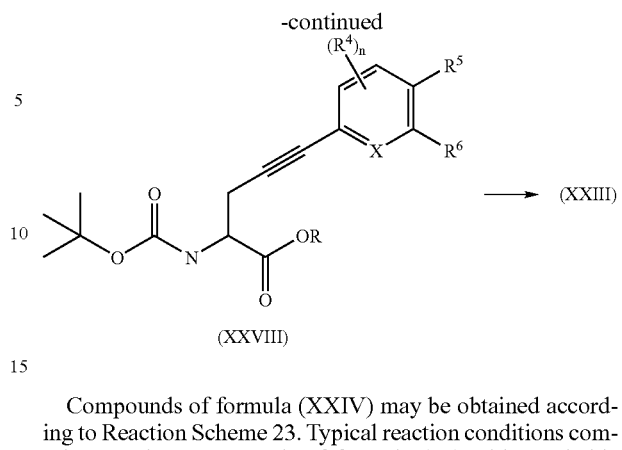

The compounds of general formula (XXV) may be generated according to Reaction Scheme 24 by reacting the appropriate compound of general formula (XXVI) with magnesium metal in THF. Typical reaction conditions comprise reaction at a temperature ranging from room temperature to 65° C., in a suitable solvent (such as ether or THF).

Reaction Scheme 24

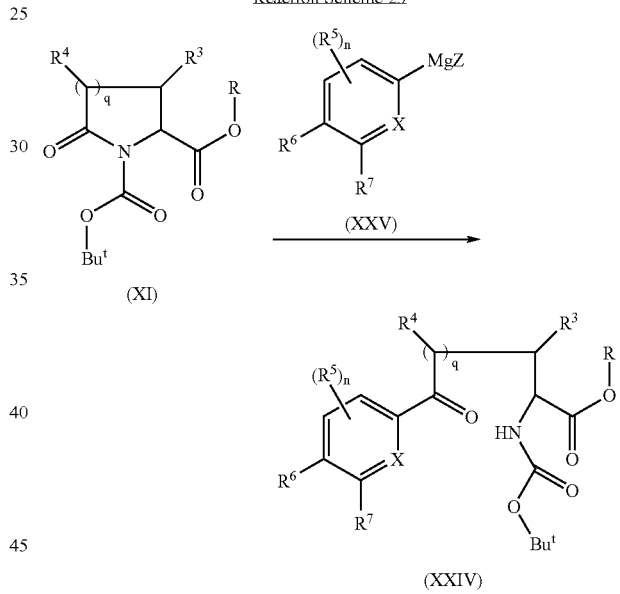

Compounds of general formula (XXVI), are either commercially available or may be synthesized following the procedures described in Reaction Scheme 25 by reacting compounds of formula (XIV) as above defined with the appropriate benzyl bromide (XXVII) in the presence of a suitable base (such as potassium carbonate) in a suitable solvent (such as acetone) at a temperature ranging from room temperature to reflux.

It will be appreciated that compounds of formula (XXVI) where $R^7$ is —$CH_2OR^8$, may be prepared by analogous methods starting from the hydroxy compound corresponding to a compound of formula (XIV).

Compounds of general formula (XIV) or (XXVII) are commercially available or may be prepared by procedures known to the skilled person.

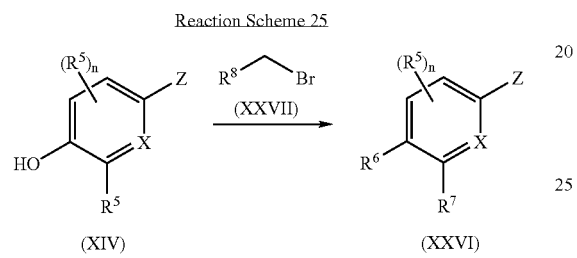

Compounds of general formula (XXIIa), that is a compound of formula (XII) wherein q=1 and $R^3$, $R^4$ are hydrogen, may be prepared according to Reaction Scheme 26 by treating compounds with general formula (XXVIII) with an excess (eg 2.5 eq) of acetyl chloride and methanol. Typical reaction conditions comprise reacting (XXVIII) in a suitable aprotic solvent (such as ethyl acetate) at room temperature.

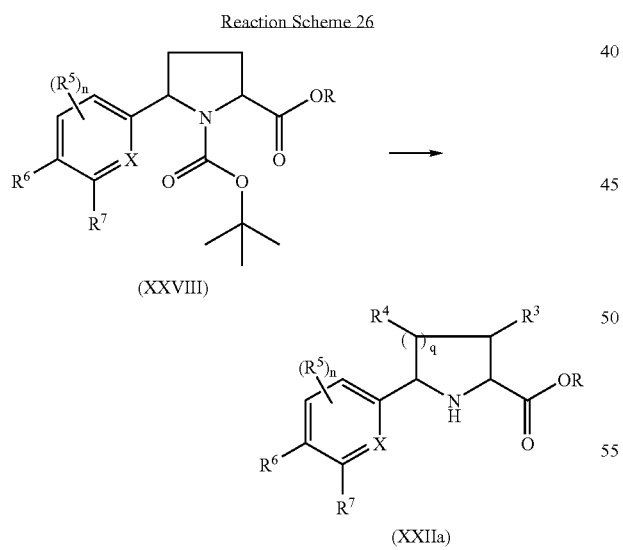

Compounds of general formula (XXVIIIa), that is a compound of formula (XXVIII) wherein $R^6$ is —$(CH_2)_2R^8$, may be prepared according to Reaction Scheme 27 by reacting compounds of general formula (XXIX) with palladium on charcoal under an atmosphere of hydrogen (1 atm) in a suitable alcoholic solvent (such as methanol). It will be appreciated that compounds of formula (XXVIIIa) where $R^7$ is —$(CH_2)_2R^8$ may be prepared by analogous methods from the respective —CH=CH—$R^8$ compound corresponding to compound (XXIX).

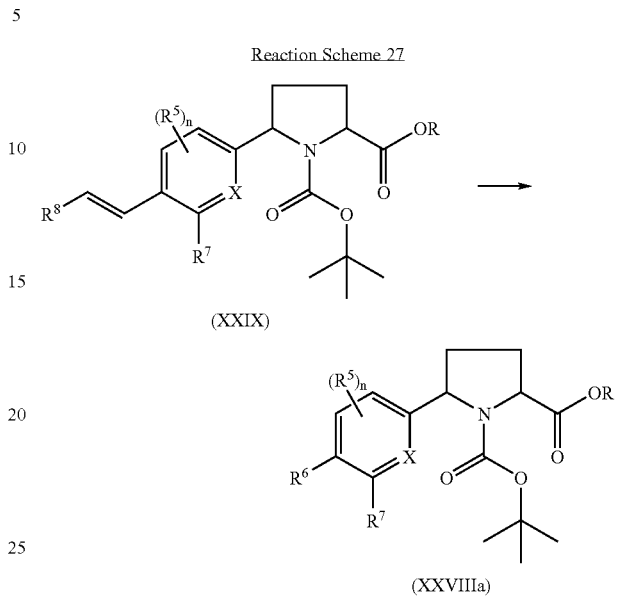

Compounds of general formula (XXIX) may be generated according to Reaction Scheme 28 by reacting compounds of general formula (XXX), whereas Y is a halogen (such as Br), with boronic acid derivatives of general formula (XXXI), with R' and R" being a $C_1$-$C_3$ alkyl group or BOR'OR" being a five or six membered saturated heterocycle (such as 4,4,5,5-tetramethyl-1,3,2-dioxaborolane), in the presence of a metal catalyst (such as Pd(PPh$_3$)$_4$) in a suitable solvent (such as dioxane) at elevated temperatures (such as 80° C.). Compounds of general formula (XXXI) are either commercially available or synthesized via methodologies widely known in the literature.

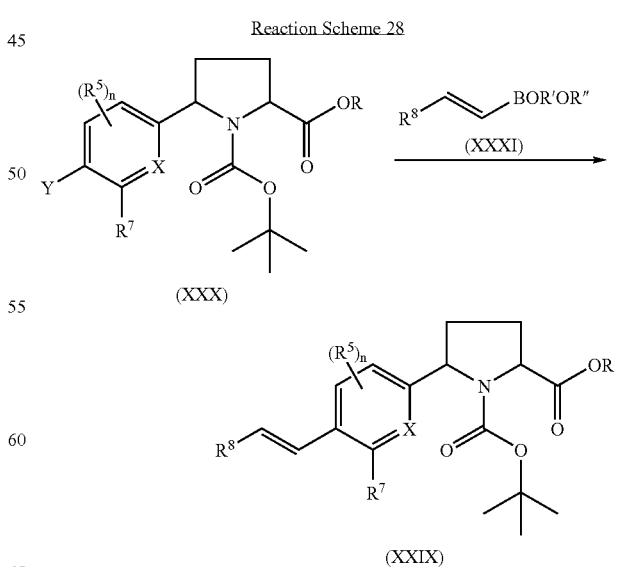

Compounds of general formula (XXX) may be generated according to Reaction Scheme 29. Typical reaction conditions comprise reacting compounds of general formula (XXXII) with a suitable reagent for introducing a BOC protecting group onto an amine (such as di-tert-butyl dicarbonate) in an aprotic solvent (such as THF or DCM) at room temperature.

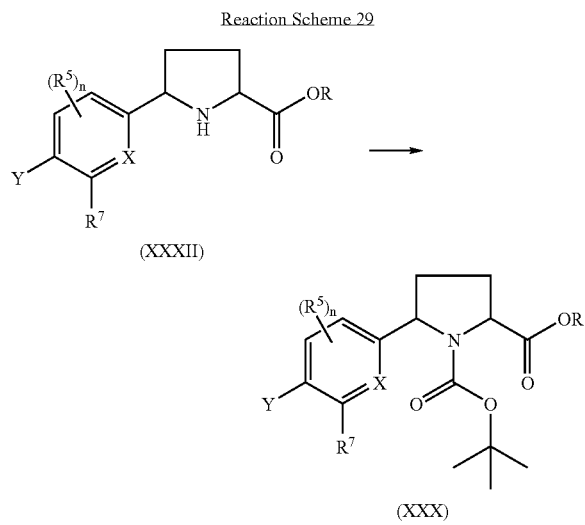

Compounds of general formula (XXXII) may be prepared according to Reaction Scheme 30 by reacting compounds of general formula (XXXIII) with platinum on carbon under an atmosphere of hydrogen (1 atm) in a suitable solvent (such as ethyl acetate) at room temperature.

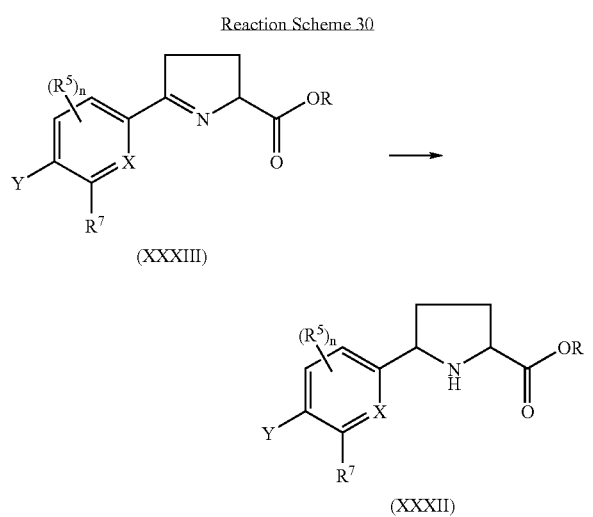

Compounds of general formula (XXXIII) may be generated according to Reaction Scheme 31 by reacting compounds of general formula (XXXIV) in the presence of a metal catalyst (such as silver-(I)-triflate) in a suitable solvent (such as DMF or acetonitrile) at temperatures ranging from room to reflux temperature.

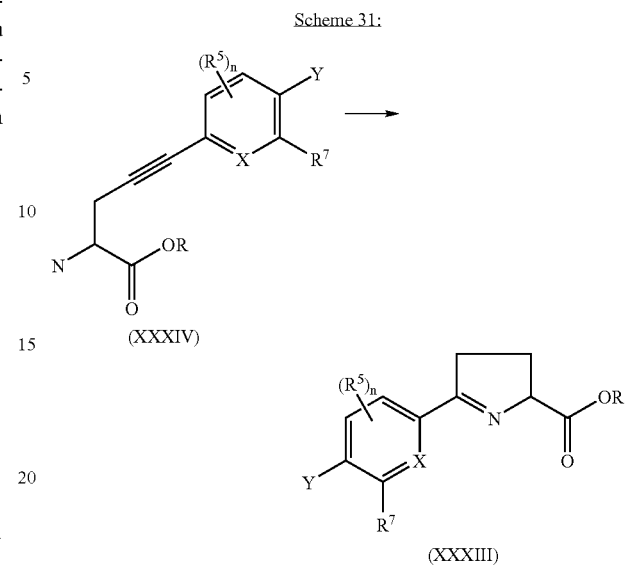

Compounds of general formula (XXXIV) may be generated according to Reaction Scheme 32 by reacting compounds of general formula (XXXV) under conditions which are widely know in the literature to remove the BOC protecting group (such as trifluoroacetic acid) in a suitable solvent (such as dichloromethane) at 0° C. to room temperature.

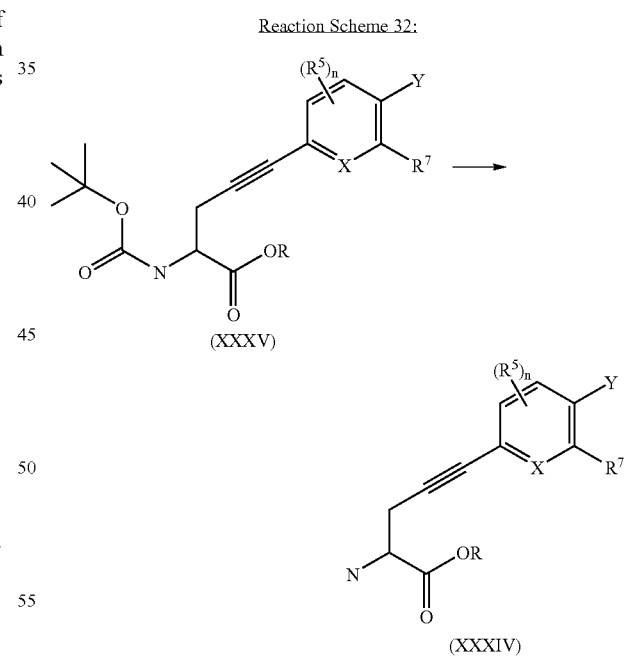

Compounds of general formula (XXXV) may be generated according to Reaction Scheme 33 reacting compounds of general formula (XXXVI) with compounds of general formula (XXXVII), whereas Z and Y represent suitable halogen combinations (such as I and Br respectively), in the presence of a palladium catalyst (such as $PdCl_2(PPh_3)_2$), copper-(I)-iodide, and suitable amine (such as diethylamine) in a polar aprotic solvent (such as diethylether) at room temperature.

Compounds of general formula (XXXVI) are either commercially available or may be synthesized by analogous methodologies widely known in the literature using commercially available starting materials (see B. van Esseveldt, Journal of Organic Chemistry 2005, 70, 1791-1795 and references cited herein). Compounds of general formula (XXXVII) are either commercially available or may be synthesized by analogous methodologies widely known in the literature.

Reaction Scheme 33

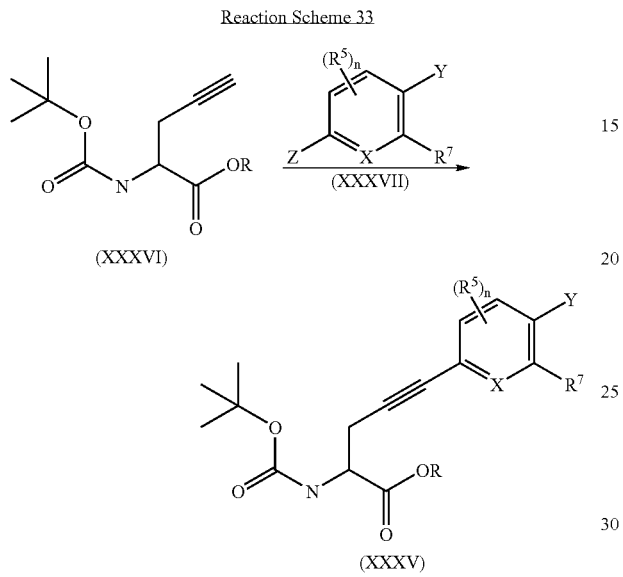

(XXXVI)

(XXXV)

Compounds of general formula (XXXVIII) may be generated according to Reaction Scheme 34 by reacting compounds of general formula (XXXIX) under a hydrogen atmosphere (1 atm) in the presence of palladium on carbon in an alcoholic solvent (such as methanol) at room temperature.

Reaction Scheme 34

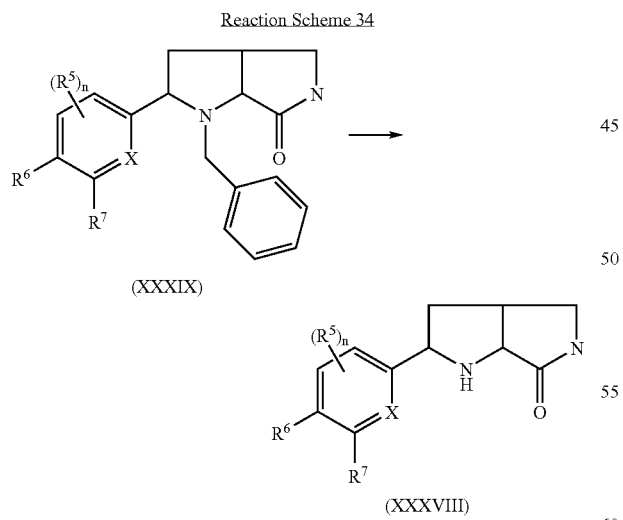

(XXXIX)

(XXXVIII)

Compounds of general formula (XXXIX) may be generated according to Reaction Scheme 35 by reacting compounds of general formula (XL) in the presence of oxygen, dimethylsulfoxide and a suitable base (such as potassium tert-butoxide) in a suitable solvent (such as tetrahydrofuran) at room temperature.

Reaction Scheme 35

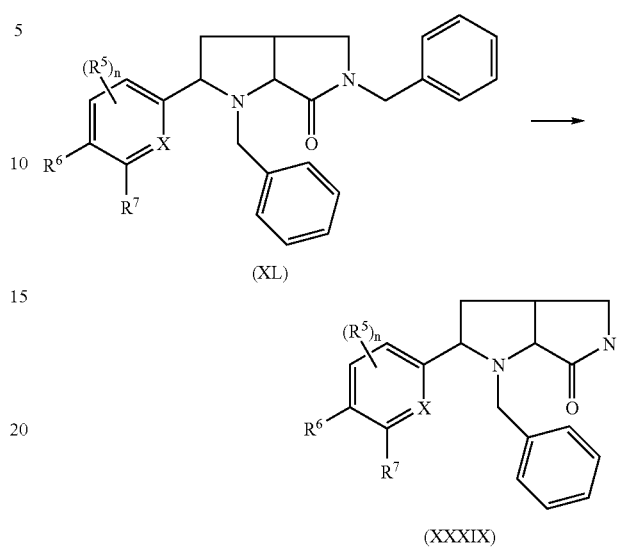

(XL)

(XXXIX)

Compounds of general formula (XL) may be generated according to Reaction Scheme 36 by reacting compound (XLI) with compounds of general formula (XLII), wherein Z is CHO, in the presence of a suitable base (such as DIPEA) in a suitable solvent (such as toluene) at elevated temperatures (such as 120° C.). Compounds of general formula (XLII) with Z being CHO may be generated via an analogous procedure to that described hereinabove (scheme 25) using the appropriate starting material.

Reaction Scheme 36:

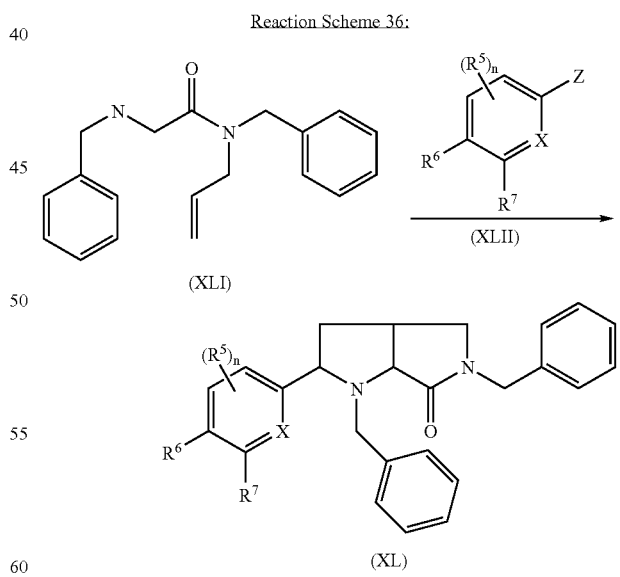

(XLI)

(XLII)

(XL)

Compound (XLI) may be generated according to Reaction Scheme 37 by treating compound (XLIII), under conditions well known in the literature to remove a BOC protecting group (such as trifluoroacetic acid in dichloromethane) at room temperature.

Reaction Scheme 37

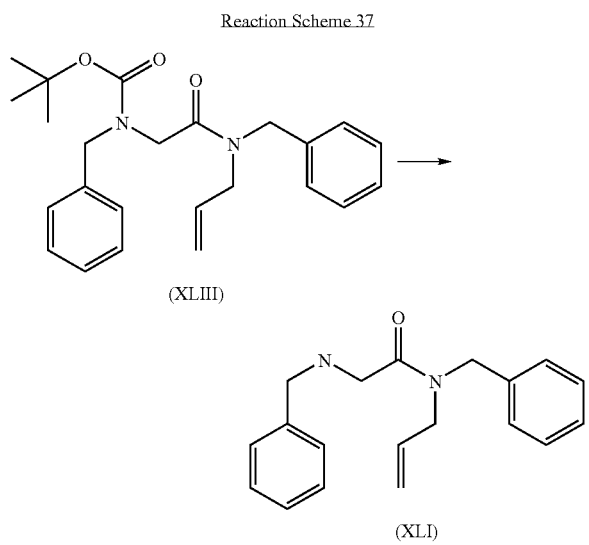

(XLIII)

(XLI)

Compound (XLIII) may be generated according to Reaction Scheme 38 by reacting compound (XLIV), readily available via procedures known in the literature (e.g. see D. J. Aitken, J. Chem. Soc. Perkin Trans. 1, 1997, 1681), and N-(phenylmethyl)-2-propen-1-amine (commercially available or prepared via procedures widely known in the literature) using an appropriate coupling agent (such as HATU or TBTU) and a suitable base (such as DIPEA) in an aprotic solvent (such as DMF) at room temperature.

Reaction Scheme 38

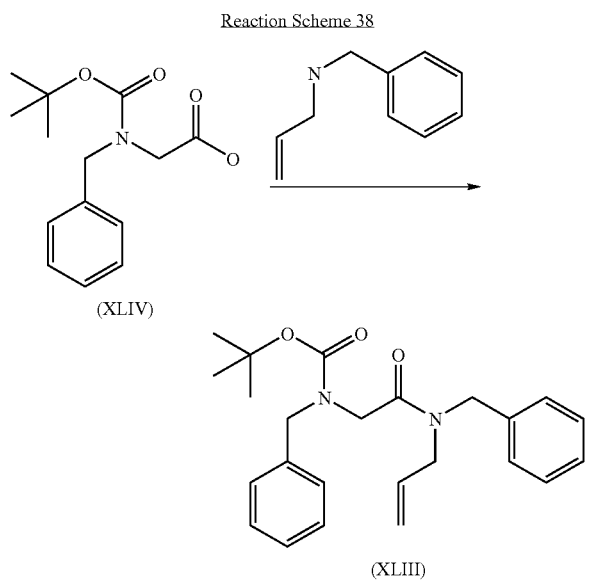

(XLIV)

(XLIII)

Alternatively, compounds of formula (IIc), i.e. compounds of formula (II) wherein $R^6$ is $—OCHR^8R^9$, can be prepared according to Reaction Scheme 39 by reacting compounds of formula (III) with a compound of formula $HOCHR^8R^9$ under Mitsunobu conditions (Hughes, D. L. The Mitsunobu Reaction, Org. React. 1992, 42, 335-656). Typical reaction conditions comprise reaction in the presence of $PPh_3$ and DIAD in a suitable solvent (such as THF) at low temperature. It will be appreciated that compounds of formula (IIc) where $R^7$ is $—OCHR^8R^9$, can be prepared by analogous methods starting from the hydroxy compound corresponding to compounds of formula (III). Compounds of formula $HOCHR^8R^9$ are either commercially available or can be synthesized via methodologies widely known in the literature.

Reaction Scheme 39

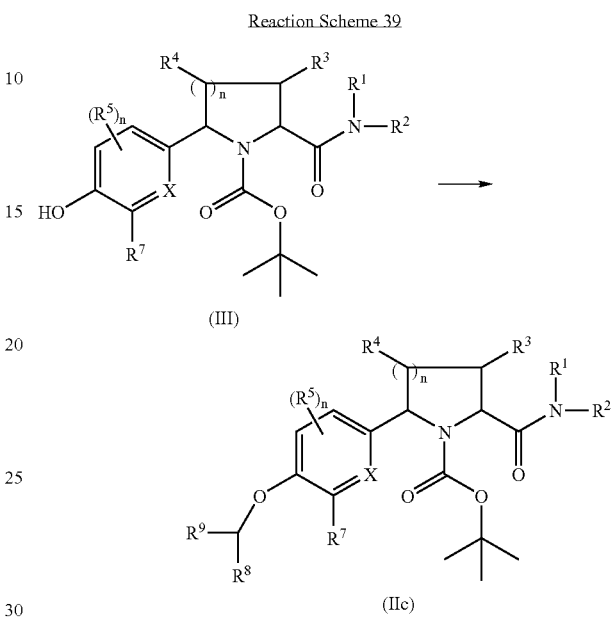

(III)

(IIc)

As discussed hereinabove, it is believed that compounds of the invention may be useful for the treatment of diseases and conditions mediated by modulation of voltage-gated sodium channels.

Therefore, according to a further aspect, the invention provides a compound of the invention for use as a medicament, preferably a human medicament.

According to a further aspect the invention provides the use of a compound of the invention in the manufacture of a medicament for treating or preventing a disease or condition mediated by modulation of voltage-gated sodium channels.

Without wishing to be bound by theory, diseases or conditions that may be mediated by modulation of voltage-gated sodium channels are selected from the list consisting of [the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10)]:

i) Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

ii) Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

iii) Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

iv) Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-induced Anxiety Disorder, Alcohol-Induced Sexual Dysfunction, Alcohol-induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-induced Anxiety Disorder, Caffeine-induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-induced Anxiety Disorder and Phencyclidine-Related Disorder Not Otherwise Specified (292.9); Sedative-, Hypnotic, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

v) Enhancement of cognition including the treatment of cognition impairment in other diseases such as schizophrenia, bipolar disorder, depression, other psychiatric disorders and psychotic conditions associated with cognitive impairment, e.g. Alzheimer's disease:

vi) Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome:

vi) Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50):

vii) Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

viii) Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

ix) Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9): and x) Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

xi) Impulse control disorder" including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

In another embodiment, diseases or conditions that may be mediated by modulation of voltage gated sodium channels are depression or mood disorders In another embodiment, diseases or conditions that may be mediated by modulation of voltage gated sodium channels are substance related disorders.

In a further embodiment, diseases or conditions that may be mediated by modulation of voltage gated sodium channels are Bipolar Disorders (including Bipolar I Disorder, Bipolar II Disorder (i.e. Recurrent Major Depressive Episodes with Hypomanic Episodes) (296.89), Cyclothymic Disorder (301.13) or Bipolar Disorder Not Otherwise Specified (296.80)).

In a still further embodiment, diseases or conditions that may be mediated by modulation of voltage gated sodium channels are Nicotine-Related Disorders such as Nicotine Dependence (305.1), Nicotine Withdrawal (292.0) or Nicotine-Related Disorder Not Otherwise Specified (292.9).

In an embodiment, compounds of the invention may be useful as analgesics. For example they may be useful in the treatment of chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

Compounds of the invention may be useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of the invention may also be useful in the amelioration of inflammatory disorders, for example in the treatment of skin conditions (e.g. sunburn, burns, eczema, dermatitis, psoriasis); ophthalmic diseases; lung disorders (e.g. asthma, bronchitis, emphysema, allergic rhinitis, non-allergic rhinitis, cough, respiratory distress syndrome, pigeon fancier's disease, farmer's lung, chronic obstructive pulmonary disease, (COPD); gastrointestinal tract disorders (e.g. Crohn's disease, ulcerative colitis, coeliac disease, regional ileitis, irritable bowel syndrome, inflammatory bowel disease, gastroesophageal reflux disease); other conditions with an inflammatory component such as migraine, multiple sclerosis, myocardial ischemia.

Compounds of the invention may also be useful in the treatment and/or prevention of disorders treatable and/or preventable with anti-convulsive agents, such as epilepsy including post-traumatic epilepsy, obsessive compulsive disorders (OCD), sleep disorders (including circadian rhythm disorders, insomnia & narcolepsy), tics (e.g. Giles de la Tourette's syndrome), ataxias, muscular rigidity (spasticity), and temporomandibular joint dysfunction.

Compounds of the invention may also be useful in the treatment of bladder hyperrelexia following bladder inflammation.

Compounds of the invention may also be useful in the treatment of neurodegenerative diseases and neurodegeneration such as dementia, particularly degenerative dementia (including senile dementia, Alzheimer's disease, Pick's disease, Huntington's chorea, Parkinson's disease and Creutzfeldt-Jakob disease, motor neuron disease); The compounds may also be useful for the treatment of amyotrophic lateral sclerosis (ALS) and neuroinflamation.

Compounds of the invention may also be useful in neuroprotection and in the treatment of neurodegeneration following stroke, cardiac arrest, pulmonary bypass, traumatic brain injury, spinal cord injury or the like.

Compounds of the invention may also be useful in the treatment of tinnitus, and as local anaesthetics.

The compounds of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. The compounds of the present invention may be used in combination with other antithrombotic drugs such as thrombin inhibitors, thromboxane receptor antagonists, prostacyclin mimetics, phosphodiesterase inhibitors, fibrinogen antagonists, thrombolytic drugs such as tissue plaminogen activator and streptokinase, non-steroidal anti-inflammatory drugs such as aspirin, and the like.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with antidepressants to treat or prevent depression and mood disorders.

The compounds of the invention may be used in combination with the following agents to treat or prevent bipolar disease: i) mood stabilisers; ii) antipsychotics; and iii) antidepressants.

The compounds of the invention may be used in combination with the following agents to treat or prevent anxiety disorders: i) anxiolytics; and ii) antidepressants.

The compounds of the invention may be used in combination with the following agents to improve nicotine withdrawal and reduce nicotine craving: i) nicotine replacement therapy for example a sublingual formulation of nicotine beta-cyclodextrin and nicotine patches; and ii) bupropion.

The compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

The compounds of the invention may be used in combination with the following agents to improve opiate withdrawal and reduce opiate craving: i) opioid mu receptor agonist/opioid kappa receptor antagonist for example buprenorphine; ii) opioid receptor antagonists for example naltrexone; and iii) vasodilatory antihypertensives for example Iofexidine.

The compounds of the invention may be used in combination with the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; v) other sedative-hypnotics for example chloral hydrate and chlormethiazole.

The compounds of the invention may be used in combination with the following agents to treat anorexia: i) appetite stimulants for example cyproheptidine; ii) antidepressants; iii) antipsychotics; iv) zinc; and v) premenstral agents for example pyridoxine and progesterones.

The compounds of the invention may be used in combination with the following agents to treat or prevent bulimia: i)

antidepressants; ii) opioid receptor antagonists; iii) antiemetics for example ondansetron; iv) testosterone receptor antagonists for example flutamide; v) mood stabilisers; vi) zinc; and vii) premenstral agents.

The compounds of the invention may be used in combination with the following agents to treat or prevent autism: i) antipsychotics; ii) antidepressants; iii) anxiolytics; and iv) stimulants for example methylphenidate, amphetamine formulations and pemoline.

The compounds of the invention may be used in combination with the following agents to treat or prevent ADHD: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

The compounds of the invention may be used in combination with the following agents to treat personality disorders: i) antipsychotics; ii) antidepressants; iii) mood stabilisers; and iv) anxiolytics.

The compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

The compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

It will be appreciated that references herein to "treatment" extend to prophylaxis, prevention of recurrence and suppression or amelioration of symptoms (whether mild, moderate or severe) as well as the treatment of established conditions.

The compound of the invention may be administered as the raw chemical but the active ingredient is preferably presented as a pharmaceutical formulation.

According to a further aspect, the invention provides a pharmaceutical composition comprising a compound of the invention, in association with one or more pharmaceutically acceptable carrier(s), diluents(s) and/or excipient(s). The carrier, diluent and/or excipient must be "acceptable" in the sense of being compatible with the other ingredients of the composition and not deleterious to the recipient thereof.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any route, and include those in a form adapted for oral, topical or parenteral administration to mammals including humans.

The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter-sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, for example from 10-60% by weight, of the active material, depending on the method of administration. Where the compositions comprise dosage units, each unit will for example contain from 5-1000 mg of the active ingredient. The dosage as employed for adult human treatment may range from 10 to 3000 mg per day depending on the route and frequency of administration. For oral administration a typical dose may be in the range of 50 to 1500 mg per day, for example 120 to 800 mg per day.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests.

All publications, including, but not limited to, patents and patent applications cited in this specification, are herein incorporated by reference as if each individual publication were specifically and individually indicated to be incorporated by reference herein as though fully set forth.

It will be appreciated that the invention includes the following further aspects. The embodiments described for the first aspect similarly apply to these further aspects. The diseases and conditions described above extend, where appropriate, to these further aspects:

i) A compound of the invention for use in treating or preventing a disease or condition mediated by modulation of voltage-gated sodium channels.

ii) A method of treatment or prevention of a disease or condition mediated by modulation of voltage-gated sodium channels in a mammal comprising administering an effective amount of a compound of the invention.

iii) Use of a compound of the invention in the manufacture of a medicament to treat or prevent a disease or condition mediated by modulation of voltage-gated sodium channels.

iv) Use of a compound of the invention to treat or prevent a disease or condition mediated by modulation of voltage-gated sodium channels.

EXAMPLES

The invention is illustrated by the Examples described below.

In the procedures that follow, after each starting material, reference to a Description or Example by number is typically provided. This is provided merely for assistance to the skilled chemist. The starting material may not necessarily have been prepared from the batch referred to.

The compounds described in the Examples described hereinafter have all been prepared as a first step from stereochemically pure methyl 5-oxo-L-prolinate or ethyl 5-oxo-D-prolinate, for example 99% ee. The stereochemistry of the compounds of the Descriptions and Examples have been assigned on the assumption that the pure configuration of 5-oxo-prolinate is maintained throughout any subsequent reaction conditions.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

The absolute configuration of the stereocenter at the 2-position as shown below the has been assigned on the basis of NOE $^1$H NMR experiments, by determining the relative stereochemistry of this stereocenter with respect to the one at the 5-position.

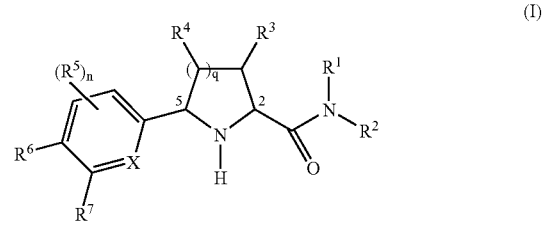

(I)

Compounds are named using ACD/Name PRO6.02 chemical naming software (Advanced Chemistry Development Inc., Toronto, Ontario, M5H2L3, Canada).

Proton Magnetic Resonance (NMR) spectra are typically recorded either on Varian instruments at 300, 400, 500 or 600 MHz, or on a Bruker instrument at 300 or 400 MHz. Chemical shifts are reported in ppm (δ) using the residual solvent line as internal standard. Splitting patterns are designed as s, singlet; d, doublet; t, triplet; q, quartet; m, multiplet; b, broad. The NMR spectra were recorded at a temperature ranging from 25 to 90° C. When more than one conformer was detected the chemical shifts for the most abundant one is reported.

HPLC analysis indicated by $R_t$(HPLC): x min, was performed on an Agilent 1100 series instrument using a Luna 3u C18(2) 100 A (50×2.0 mm) column (mobile phase: 100% [water+0.05% TFA] to 95% [acetonitrile+0.05% TFA] in 8 min, flux=1 ml/min, detection wavelength 220 nm.

Mass spectra (MS) are typically taken on a 4 II triple quadrupole Mass Spectrometer (Micromass UK) or on a Agilent MSD 1100 Mass Spectrometer, operating in ES (+) and ES (−) ionization mode or on a Agilent LC/MSD 1100 Mass Spectrometer, operating in ES (+) and ES (−) ionization mode coupled with HPLC instrument Agilent 1100 Series [LC/MS–ES (+): analysis performed on a Supelcosil ABZ+Plus (33×4.6 mm, 3 µm) (mobile phase: 100% (water+0.1% HCO$_2$H] for 1 min, then from 100% [water+0.1% HCO$_2$H] to 5% [water+0.1% HCO$_2$H] and 95% [CH$_3$CN] in 5 min, finally under these conditions for 2 min; T=40° C.; flux=1 mL/min; LC/MS–ES (−): analysis performed on a Supelcosil ABZ+Plus (33×4.6 mm, 3 µm) (mobile phase: 100% [water+0.05% NH$_3$] for 1 min, then from 100% [water+0.05% NH$_3$ to 5% [water+0.05% NH$_3$] and 95% [CH$_3$CN] in 5 min, finally under these conditions for 2 min; T=40° C.; flux=1 mL/min]. In the mass spectra only one peak in the molecular ion cluster is reported.

Total ion current (TIC) and DAD UV chromatographic traces together with MS and UV spectra associated with the peaks are typically taken also on a UPLC/MS Acquity™ system equipped with 2996 PDA detector and coupled to a Waters Micromass ZQ™ mass spectrometer operating in positive or negative electrospray ionisation mode. [LC/MS-ES (+/−): analyses performed using an Acquity™ UPLC BEH C18 column (50×21 mm, 1.7 μm particle size), column temperature 40° C. (mobile phase: A-water+0.1% HCOOH/B-MeCN+0.075% HCOOH, Flow rate: 1.0 mL/min, Gradient: t=0 min 3% B, t=0.05 min 6% B, t=0.57 min 70% B, t=1.4 min 99% B, t=1.45 min 3% B)]. The usage of this methodology is indicated by "UPLC" in the analytic characterization of the described compounds.

The optical rotation was measured on a JASCO DIP-360 digital polarimeter (λ=589 nm, T=20° C., c=1 in MeOH).

For reactions involving microwave irradiation, a Personal Chemistry Emrys™ Optimizer was used.

Flash silica gel chromatography was carried out on silica gel 230-400 mesh (supplied by Merck AG Darmstadt, Germany) or over Varian Mega Be—Si pre-packed cartridges or over pre-packed Biotage silica cartridges.

SPE-SCX cartridges are ion exchange solid phase extraction columns by supplied by Varian. The eluent used with SPE-SCX cartridges is methanol followed by 2N ammonia solution in methanol.

In a number of preparation purification was performed using either Biotage manual flash chromatography (Flash+) or automatic flash chromatography (Horizon) systems. All these instruments work with Biotage Silica cartridge.

SPE-Si cartridges are silica solid phase extraction columns supplied by Varian.

It will be recognised that spectra and diffraction data will vary slightly according to various factors such as the temperature, concentration and instrumentation used. The skilled person will recognise that XRPD peak positions are affected by differences in sample height. The peak positions quoted herein are thus subject to a variation of +/−0.15 degrees 2-theta.

X-Ray Powder Diffraction

X Ray Powder Diffraction (XRPD) analysis was performed on Bruker D5005, using Sol-X detector. The acquisition conditions were: radiation: Cu Kα, generator tension: 40 kV, generator current: 50 mA, start angle: 2.0° 2θ, end angle: 45.0° 2θ, step size: 0.02° 2θ, time per step: 1 seconds. The sample was prepared on zero background sample holder.

Differential Scanning Calorimetry (DSC): It should be recognized that the endotherm peak as measured is dependent under a number of factors including the machine employed, the rate of heating, the calibration standard, humidity and the purity of the sample used.

Melting points reported in the experimentals are estimated on the basis of the onset of endotherm peaks registered during DSC analysis.

The following table lists the used abbreviations:
BOC$_2$O bis(1,1-dimethylethyl)dicarbonate
DCM—dichloromethane
DIAD—diisopropyl diazodicarboxylate
DIPEA—diisopropylethylamine
DMAP—dimethylaminopyridine
DMF—dimethylformamide
O-(7-azabenzotriazol-1-yl)-N,N,N',N'-tetramethyluronium
HATU—hexafluorophosphate
O-(benzotriazol-1-yl)-N,N,N'N'-tetramethyluronium
TBTU—tetrafluoroborate
TFA—trifluoroacetic acid
TEA—triethylamine
THF—tetrahydrofuran
TMEDA—N,N,N',N'-tetramethylethylenediamine
MTBE methyl-t-butyl ether
Et$_2$O diethyl ether
AcOEt ethyl acetate Description 1: Ethyl 6-bromo-2-pyridinecarboxylate (D1)

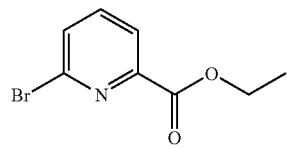

6-Bromo-2-pyridinecarboxylic acid (925 mg, 4.95 mmol) (Aldrich) was dissolved in hydrochloric acid/ethanol (1.25 M, 20 ml) and stirred under reflux for 3 h. Then the solvent was evaporated under reduced pressure. The remaining residue was taken up with DCM and washed with saturated aqueous NaHCO$_3$ solution. Evaporation of the solvent afforded the title compound (1.045 g, 92%). The material was used in the following step without any further purification; $^1$H-NMR (300 MHz, CDCl$_3$) δ (ppm): 8.1-8.0 (m, 1H), 7.8-7.5 (m, 2H), 4.4 (q, 2H), 1.4 (t, 3H).

Description 2: Ethyl 6-(4-hydroxyphenyl)-2-pyridinecarboxylate (D2)

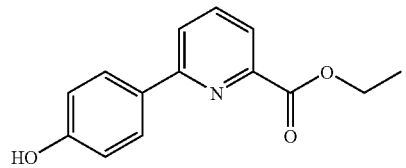

To a solution of ethyl 6-bromo-2-pyridinecarboxylate (D1, 460 mg, 2.0 mmol) in dioxane (4 ml) were added 4-hydroxyphenyl boronic acid (414 mg, 3.0 mmol), Pd(PPh$_3$)$_4$ (450 mg, 0.4 mmol) and potassium carbonate (420 mg, 4.0 mmol) dissolved in water (2 ml). The reaction mixture was heated in a microwave synthesizer for 15 min at 150° C. The reaction mixture was diluted with ethyl acetate (150 ml) and washed with saturated aqueous ammonium chloride (40 ml). The resulting crude material was purified by chromatography on silica gel using ethyl acetate/cyclohexanes (1:1) to afford the title compound (340 mg, 72%); $^1$H-NMR (300 MHz, CDCl$_3$) δ (ppm): 8.05 (d, 2H), 8.0 (m, 1H), 7.80 (d, 2H), 7.05 (d, 2H), 6.80 (bt, 1H), 4.50 (q, 2H), 1.45 (t, 3H).

Description 3: Ethyl 6-(4-{[(3-fluorophenyl)methyl]oxy}phenyl)-2-pyridinecarboxylate (D3)

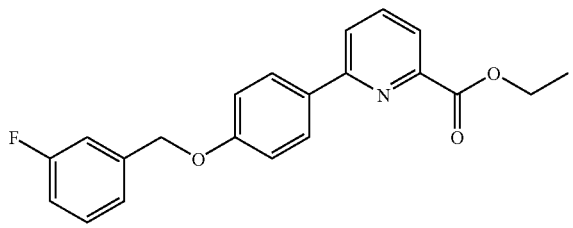

A solution of ethyl 6-(4-hydroxyphenyl)-2-pyridinecarboxylate (D2, 100 mg, 0.41 mmol), 1-(bromomethyl)-3-fluorobenzene (117 mg, 0.62 mmol) and potassium carbonate (138 mg, 1.0 mmol) was stirred at 60° C. for 4 h. Then the solvent was evaporated under reduced pressure and the resulting crude material was purified by chromatography on silica gel using ethyl acetate/cyclohexanes (1:1) to afford the title compound (110 mg, 76%); MS: (ES/+) m/z: 352 [MH$^+$], C21H18FNO3 requires 351; $^1$H-NMR (300 MHz, CDCl$_3$) δ (ppm): 8.05 (d, 2H), 8.0 (m, 1H), 7.80 (d, 2H), 7.35 (m, 1H), 7.20 (m, 2H), 7.05 (d, 2H), 7.00 (m, 1H), 5.15 (s, 2H), 4.50 (q, 2H), 1.45 (t, 3H).

Description 4: 6-(4-{[(3-Fluorophenyl)methyl]oxy}phenyl)-2-pyridinecarboxamide (D4)

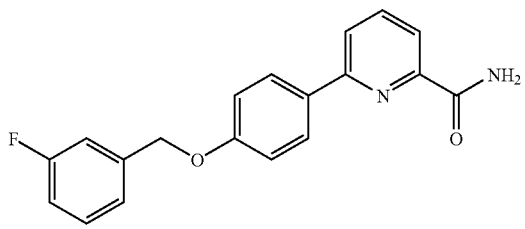

A solution of ethyl 6-(4-{[(3-fluorophenyl)methyl]oxy}phenyl)-2-pyridinecarboxylate (D3, 110 mg, 0.30 mmol) in MeOH/NH$_3$ (7M, 5 ml) was stirred at 60° C. in a sealed tube for 6 h. The solvent was then evaporated under reduced pressure to afford the title compound (95 mg); MS: (ES/+) m/z: 323 [MH$^+$], C19H15FNO3 requires 322; $^1$H-NMR (300 MHz, DMSO) δ (ppm): 8.25 (bs, 2H), 8.20 (d, 1H), 8.05 (d, 1H), 7.95 (t, 1H), 7.85 (d, 1H), 7.65 (bs, 1H), 7.40 (t, 1H), 7.30 (d, 2H), 7.15 (t, 1H), 7.10 (d, 2H), 5.20 (s, 2H).

Description 5: 1-(1,1-Dimethylethyl) 2-methyl (2S)-5-oxo-1,2-pyrrolidinedicarboxylate (D5)

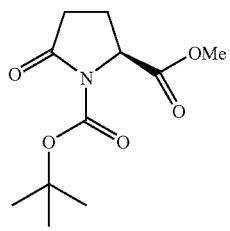

To a solution of commercially available (Aldrich) methyl 5-oxo-L-prolinate (20 g, 140 mmol) in DCM (200 ml) were added triethylamine (19.6 ml, 140 mmol), 4-(dimethylamino)pyridine (17.2 g, 140 mmol) and finally, dropwise, a solution of BOC$_2$O (61 g, 280 mmol) in DCM (100 ml). The resulting red mixture was stirred at room temperature for 2 hours. Then the solvent was removed in vacuo and the crude material was purified by chromatography on silica gel eluting with cyclohexane/ethyl acetate (7:3 to 4:6) to afford (after trituration in hexane/diethylether 1:1) the title compound as a white solid (32.4 g, 96%); R$_f$ (cyclohexanes:ethyl acetate=65:35): 0.21; $^1$H NMR (300 MHz, CDCl$_3$) δ (ppm): 4.62 (dd, 1H), 3.78 (s, 3H), 2.68-2.58 (m, 1H), 2.52-2.45 (m, 1H), 2.37-2.27 (m, 1H), 2.08-1.97 (m, 1H), 1.48 (s, 9H).

Description 6: Methyl (2S)-2-({[(1,1-dimethylethyl)oxy]carbonyl}amino)-5-oxo-5-{4-[(phenylmethyl)oxy]phenyl}pentanoate (D6)

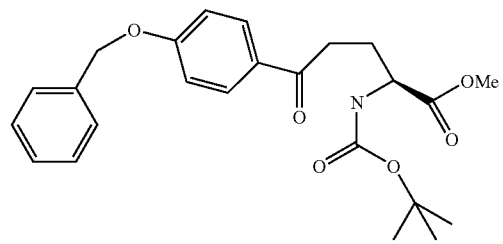

To a solution of commercially available (Aldrich) 1-bromo-4-[(phenylmethyl)oxy]benzene (390 mg, 1.48 mmol) in dry THF (2 ml) at −78° C. under nitrogen atmosphere was added dropwise n-butyllithium 1.6M solution in hexanes (0.88 ml, 1.4 mmol). The resulting suspension was stirred at −78° C. for 40 minutes and then it was added dropwise to a solution of 1-(1,1-dimethylethyl) 2-methyl (2S)-5-oxo-1,2-pyrrolidinedicarboxylate (D5, 300 mg, 1.23 mmol) in dry THF (2.4 ml) previously cooled to −78° C. The mixture was stirred at −78° C. for 40 minutes and at −40° C. for 1 h, then it was quenched at −40° C. with a saturated ammonium chloride aqueous solution. The mixture was diluted with water and extracted with ethyl acetate. The organic phase was then washed with brine, dried over Na$_2$SO$_4$, and evaporated under reduced pressure to give the crude material, which was purified by chromatography on silica gel eluting with cyclohexane/ethyl acetate (95:5), thus affording the title compound as a white solid (170 mg, 32%); R$_f$ (cyclohexane:ethyl acetate=8:2): 0.30; $^1$HNMR (300 MHz, CDCl$_3$) δ (ppm): 7.95 (d, 2H), 7.50-7.33 (m, 5H), 7.03 (d, 2H), 5.20 (bs, 1H), 5.15 (s, 2H), 4.45-4.35 (m, 1H), 3.78 (s, 3H), 3.15-2.95 (m, 2H), 2.36-2.26 (m, 1H), 2.16-2.02 (m, 1H), 1.45 (s, 9H).

Description 7: Methyl (2S)-5-{4-[(phenylmethyl)oxy]phenyl}-3,4-dihydro-2H-pyrrole-2-carboxylate (D7)

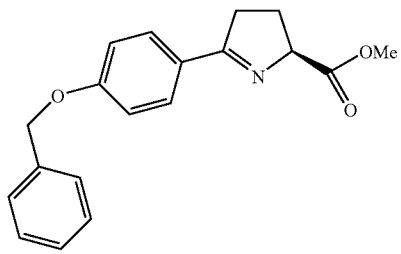

To a solution of methyl (2S)-2-({[(1,1-dimethylethyl)oxy]carbonyl}amino)-5-oxo-5-{4-[(phenylmethyl)oxy]phenyl}pentanoate (D6, 323 mg, 0.75 mmol) in dry DCM (4 ml) at 0° C. under nitrogen atmosphere was added trifluoroacetic acid (1 ml) dropwise. The resulting pale pink solution was allowed to warm to room temperature over 1 hour, then it was evaporated under vacuum, affording the title compound (291 mg, 0.94 mmol, 91%) as a greenish oil which was used in the next step without any further purification; $R_t$ (HPLC): 3.69 min; MS: (ES/+) m/z: 310 [MH$^+$], C19H19NO3 requires 309.

Description 8: Methyl (5R)-5-{4-[(phenylmethyl)oxy]phenyl}-L-prolinate (D8)

Description 9: Methyl (5S)-5-{4-[(phenylmethyl)oxy]phenyl}-L-prolinate (D9)

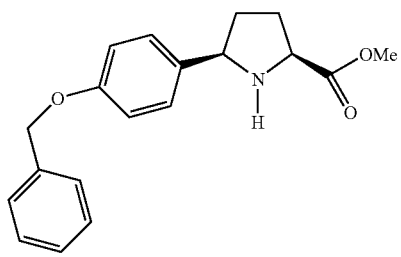

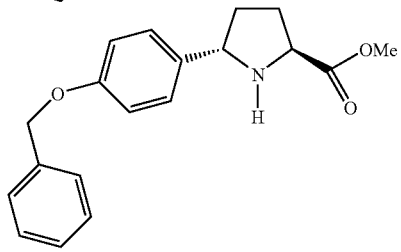

To a solution of methyl (2S)-5-{4-[(phenylmethyl)oxy]phenyl}-3,4-dihydro-2H-pyrrole-2-carboxylate (D7, 13.7 g, 32.4 mmol) in MeOH (200 ml) was added PtO$_2$ (240 mg) and the mixture was stirred under hydrogen atmosphere (2 atm) for 6 hours. Then the catalyst was filtered off and the solvent removed under reduced pressure to give a red oil which was dissolved in ethyl acetate and washed with NaHCO$_3$ solution. The resulting crude material was purified by chromatography on silica gel eluting with cyclohexane/ethyl acetate (9:1 to 8:2) to afford the title compounds:

D8: (4.15 g, 13.3 mmol, 41%); Rt (HPLC): 3.80 min; Rf (cyclohexane:ethyl acetate=7:3): 0.18; MS: (ES/+) m/z: 312 [MH$^+$], C19H21NO3 requires 311; $^1$H NMR (300 MHz, CDCl$_3$) δ (ppm): 7.40 (d, 2H); 7.35 (t, 2H); 7.33 (d, 2H); 7.29 (t, 1H); 6.93 (d, 2H); 5.03 (s, 2H); 4.23 (dd, 1H); 4.00 (dd, 1H); 3.71-3.79 (m, 3H); 2.18-2.30 (m, 1H); 2.09-2.18 (m, 2H); 1.67-1.78 (m, 1H); NOE between the proton at C2 and the proton at C5 could be observed.

D9: (0.6 g, 1.9 mmol, 6%): Rt (HPLC): 3.73 min; Rf (cyclohexane:ethyl acetate=7:3): 0.32; MS: (ES/+) m/z: 312 [MH$^+$]. C19H21NO3 requires 311; $^1$HNMR (300 MHz, CDCl$_3$) δ (ppm): 7.40 (d, 2H); 7.35 (t, 2H); 7.29 (d, 2H); 7.28 (t, 1H); 6.91 (d, 2H); 4.97-5.07 (m, 2H); 4.29 (dd, 1H); 4.09 (dd, 1H); 3.71-3.75 (m, 3H); 2.29-2.42 (m, 1H); 2.09-2.20 (m, 1H); 1.90-2.02 (m, 1H); 1.69-1.82 (m, 1H); NOE between the proton at C2 and the proton at C5 was not observed.

Description 10: (5R)-5-{4-[(Phenylmethyl)oxy]phenyl}-L-proline (D10)

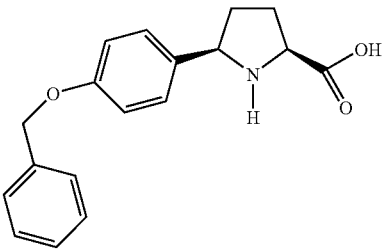

To a solution of methyl (5R)-5-{4-[(phenylmethyl)oxy]phenyl}-L-prolinate (D8, 120 mg, 0.38 mmol) in THF (2.3 ml) was added LiOH monohydrate (26 mg, 0.61 mmol) dissolved in water (1.1 ml) followed by methanol (1.1 ml). The resulting solution was stirred at room temperature for 3 hours (hydrolysis being monitored by HPLC). When hydrolysis was complete, the organic solvent was evaporated under reduced pressure (maintaining the temperature at 38° C.) to give a crude aqueous residue containing the title compound; $R_t$ (HPLC)=3.63 min; MS: (ES/+) m/z: 298 [MH$^+$], C18H19NO3 requires 297).

Description 11: (5R)-1-{[(1,1-Dimethylethyl)oxy]carbonyl}-5-{4-[(phenylmethyl)oxy]-phenyl}-L-proline (D11)

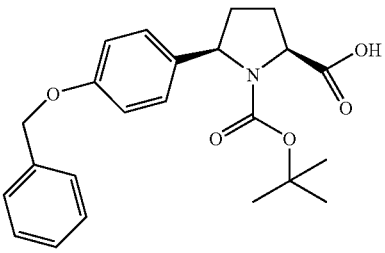

The crude reaction mixture from Description 10 was treated with BOC$_2$O (168 mg, 0.77 mmol) dissolved in THF (1.1 ml). The reaction mixture was stirred at room temperature for 3.5 hours. Then the organic solvent was evaporated and the basic aqueous solution was treated at 0° C. with aqueous 1N HCl down to pH=3, the acidic aqueous solution was extracted with ethyl acetate (2×10 ml). The organic phase was dried over $Na_2SO_4$ and evaporated under reduced pressure to give a solid, which was triturated in n-hexanes (3×6 ml) to give the title compound as a white powder (137 mg); $R_t$ (HPLC): 5.81 min; $R_f$(cyclohexane:ethyl acetate=1:1): 0.34; MS: (ES/+) m/z: 420 [M+Na$^+$] C23H27NO5 requires 397; MS: (ES/−) m/z: 396 [M−H] C23H27NO5 requires 397; $^1$HNMR (300 MHz, CDCl$_3$) δ (ppm): 7.5-7.3 (m, 5H), 7.10 (bm, 2H), 6.90 (d, 2H), 5.08 (s, 2H), 4.65 (bm, 1H), 4.50 (bm, 1H), 2.58 (bm, 1H), 2.31 (bm, 1H), 2.11-1.90 (m, 2H), 1.16 (s, 9H).

Description 12: 1,1-Dimethylethyl (2S,5R)-2-(aminocarbonyl)-5-{4-[(phenylmethyl)oxy]phenyl}-1-pyrrolidinecarboxylate (D12)

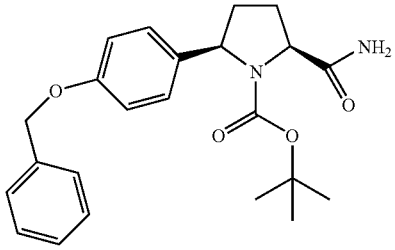

To a solution of (5R)-1-{[(1,1-dimethylethyl)oxy]carbonyl}-5-{4-[(phenylmethyl)oxy]phenyl}-L-proline (D11, 1.44 g, 3.62 mmol) in dry DMF (20 ml) were added DIPEA (1.26 ml, 7.24 mmol), then TBTU (1.23 g, 3.98 mmol) and after 20 minutes, 1,1,1,3,3,3-hexamethyldisilazane (1.15 ml, 5.43 mmol). The reaction mixture was stirred at room temperature for 2 h, then it was treated with aqueous 5% NaHCO$_3$ solution (30 ml) and stirred for further 30 minutes. The resulting mixture was diluted with water and extracted with ethyl acetate. The organic phase was then washed twice with brine/ice, dried over Na$_2$SO$_4$ and evaporated to give a colourless oil. This crude material was purified by chromatography on silica gel eluting with cyclohexane/ethyl acetate (7:3 to 5:5) to afford the title compound (1.25 g, 87%); $R_t$ (HPLC): 5.51 min; $R_f$(cyclohexane:ethyl acetate=1:1): 0.29. MS: (ES/+) m/z: 419 [M+Na$^+$]; C23H28N2O4 requires 396.

Description 13: 1,1-Dimethylethyl (2S,5R)-2-(aminocarbonyl)-5-(4-hydroxyphenyl)-1-pyrrolidinecarboxylate (D13)

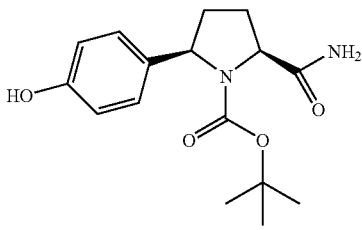

To a solution of 1,1-dimethylethyl (2S,5R)-2-(aminocarbonyl)-5-{4-[(phenylmethyl)oxy]phenyl}-1-pyrrolidinecarboxylate (D12, 1.2 g, 3.02 mmol) in methanol (25 ml) was added Pd/C 10% wt (210 mg) and the mixture was stirred under a hydrogen atmosphere (1 atm) for 6 hours. The catalyst was filtered off and the solvent removed under reduced pressure to give the title compound as a white solid (870 mg, 94%); $R_t$(HPLC): 3.61 min; $R_f$(cyclohexane:ethyl acetate=1:1): 0.18; MS: (ES/+) m/z: 329 [M+Na$^+$]. C16H22N2O4 requires 306; $^1$H NMR (300 MHz, d$_6$-DMSO) δ ppm: 9.15 (bs, 1H); 7.40 (bm, 2H); 7.30 (s, 1H); 6.90 (s, 1H); 6.65 (d, 2H); 4.50-4.80 (m, 1H); 4.05-4.28 (m, 1H); 2.07-2.24 (m, 1H); 1.95-2.07 (m, 1H); 1.60-1.89 (m, 2H); 1.00-1.45 (m, 9H).

Description 14: 1,1-Dimethylethyl (2S,5R)-2-(aminocarbonyl)-5-(4-{[(2-fluorophenyl)methyl]oxy}phenyl)-1-pyrrolidinecarboxylate (D14)

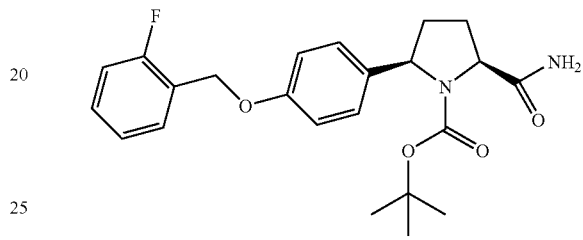

To a solution of 1,1-dimethylethyl (2S,5R)-2-(aminocarbonyl)-5-(4-hydroxyphenyl)-1-pyrrolidinecarboxylate (D13, 45 mg, 0.146 mmol) and potassium carbonate (30 mg, 0.217 mmol) in acetonitrile (2 ml) was added 1-(bromomethyl)-2-fluorobenzene (30 μl, 0.220 mmol). The mixture was stirred overnight at room temperature. Then ethyl acetate and water were added. The organic phase was then washed with brine, dried (Na$_2$SO$_4$), filtered and evaporated. The crude material was purified by chromatography on silica gel using cyclohexane/ethyl acetate (7:3 to 6:4) to afford the title compound (51 mg, 85%); $R_t$(HPLC): 5.56 min; $R_f$(cyclohexane:ethyl acetate=1:1): 0.28; $^1$H-NMR (300 MHz, CDCl$_3$) δ (ppm): 7.56-7.48 (m, 1H); 7.37-7.28 (m, 1H), 7.24-7.06 (m, 5H); 6.93 (d, 2H); 5.45-5.37 (br. s, 1H); 5.15 (s, 2H); 4.73-4.60 (m, 1H); 4.53-4.45 (m, 1H); 2.58-2.48 (m, 1H); 2.34-2.25 (m, 1H); 2.09-1.93 (m, 2H); 1.28-1.13 (br. s, 9H).

The following compounds of formula (IIc) were prepared using a similar procedure to that described in Description 14 starting from 1,1-dimethylethyl (2S,5R)-2-(aminocarbonyl)-5-(4-hydroxyphenyl)-1-pyrrolidinecarboxylate (D13) and using the appropriate benzylbromide.

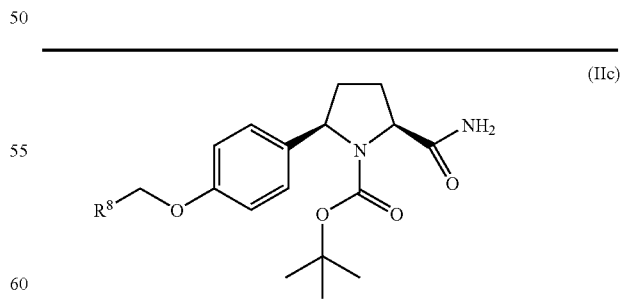

(IIc)

| No. | $R^8$ | Characterization |
|---|---|---|
| D15 | 3-fluorophenyl | $R_f$(cyclohexane:ethyl acetate = 1:1): 0.28, $R_t$ (HPLC): 5.62 min. MS: (ES/+) 437 m/z: [M + Na$^+$]. C23H27FN2O4 requires 414; $^1$H-NMR (300 MHz, CDCl$_3$) |

-continued (IIc)

| No. | R⁸ | Characterization |
|---|---|---|
| | | δ (ppm): 7.42-7.28 (m, 2H), 7.25-7.12 (m, 4H); 7.02 (dt, 1H); 6.90 (d, 2H); 5.45-5.37 (br. s, 1H); 5.08 (s, 2H); 4.75-4.60 (m, 1H); 4.53-4.45 (m, 1H); 2.58-2.48 (m, 1H); 2.34-2.25 (m, 1H); 2.09-1.90 (m, 2H); 1.30-1.12 (br. s, 9H). |
| D16 | 3-cyanophenyl | R$_f$ (cyclohexanes:ethyl acetate = 1:1): 0.25, MS: (ES/+) 444 m/z: [M + Na⁺]. C24H27N3O4 requires 421; ¹H-NMR (300 MHz, CDCl₃) δ (ppm): 7.9 (s, 1H), 7.8 (d, 2H), 7.7-7.4 (m, 3H), 7.3 (s, 1H), 6.9 (m, 3H), 5.2 (s, 2H), 4.8-4.5 (m, 1H), 2.2 (m, 1H), 2.0 (m, 2H), 1.9-1.5 (m, 3H), 1.4-1.0 (m, 8H). |
| D17 | 4-fluorophenyl | R$_f$ (cyclohexanes:ethyl acetate = 1:1): 0.29, MS: (ES/+) 437 m/z: [M + Na⁺]. C23H27FN2O4 requires 414. |
| D18 | 2-cyanophenyl | R$_f$ (cyclohexanes:ethyl acetate = 1:1): 0.25, MS: (ES/+) 444 m/z: [M + Na⁺]. C24H27N3O4 requires 421. |
| D19 | 4-cyanophenyl | R$_f$ (cyclohexanes:ethyl acetate = 1:1): 0.25, MS: (ES/+) 444 m/z: [M + Na⁺]. C24H27N3O4 requires 421. |
| D20 | 2-(trifluoromethoxy)-phenyl | R$_f$ (cyclohexanes:ethyl acetate = 1:1): 0.29, MS: (ES/+) 503 m/z: [M + Na⁺]. C24H27F3N2O5 requires 480. |

Description 21: 1,1-Dimethylethyl (2S,5R)-2-(aminocarbonyl)-5-(4-{[(1R)-1-phenylethyl]oxy}phenyl)-1-pyrrolidinecarboxylate (D21)

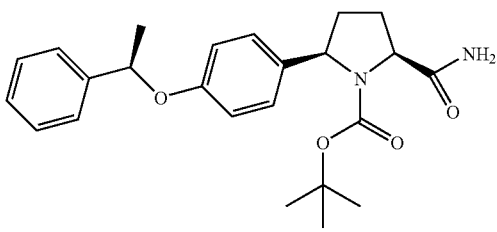

Polystyrene supported PPh₃ (100 mg, 1.5 mmol) and DIAD (30 mg, 1.5 mmol) were added to a solution of 1,1-dimethylethyl (2S,5R)-2-(aminocarbonyl)-5-(4-hydroxyphenyl)-1-pyrrolidinecarboxylate (D13, 30 mg, 0.10 mmol) in dry THF (1 ml) at 0° C. After 15 min (1R)-1-phenylethanol (24.4 mg, 0.2 mmol) was added and the reaction mixture was stirred at 0° C. for 2 h. The resin was filtered off and the solvent was evaporated. The crude material was purified by chromatography on silica gel using cyclohexanes/ethyl acetate (8:2) to afford the title compound (20 mg, 48%); R$_t$ (HPLC): 5.70 min, ¹H-NMR (400 MHz, DMSO-d₆) δ (ppm): 1.31 (s, 9H); 1.53 (d, 3H); 1.65-1.78 (m, 1H); 1.79-1.92 (m, 1H); 1.93-2.03 (m, 1H); 2.07-2.21 (m, 1H); 4.50 (br. s, 1H); 4.70 (br. s., 1H); 5.41-5.50 (m, 1H); 6.78 (d, 2H); 6.91 (s, 1H); 7.23 (br. s., 1H); 7.31 (br. s., 2H); 7.39 (br. s., 4H); 7.44 (br. s., 1H).

Description 22: 1,1-Dimethylethyl (2S,5R)-2-(aminocarbonyl)-5-{4-[(4 fluorophenyl)oxy]-phenyl}-1-pyrrolidinecarboxylate (D22)

This compound was prepared in two batches under different conditions (Conditions A and B). In a closed vial 1,1-dimethylethyl (2S,5R)-2-(aminocarbonyl)-5-(4-hydroxyphenyl)-1-pyrrolidinecarboxylate (D13, 19 mg, 0.062 mmol), copper-(II)-acetate (11 mg, 0.062 mmol), (4-fluorophenyl)boronic acid (17 mg, 0.124 mmol) and molecular sieves were suspended in DCM. Then either pyridine (Condition A, 24.5 mg, 0.31 mmol) or triethylamine (Condition B, 31.3 mg, 0.31 mmol) was added and the reaction was shaken at room temperature for 24 h. The crude reaction products from Conditions A and B were combined, filtered and evaporated. The crude residue was purified by chromatography on silica gel using cyclohexanes/ethyl acetate (7:3) to afford the title compound (28 mg, 56%); R$_t$ (HPLC): 5.61 min; MS: (ES/+) m/z: 423 [M+Na⁺], C22H25N2O4 requires 400; ¹H NMR (400 MHz, DMSO-d₆) δ ppm: 1.08 (s, 9H); 1.73-1.84 (m, 1H); 1.86-1.96 (m, 1H); 2.00-2.11 (m, 1H); 2.17-2.27 (m, 1H); 4.56-4.73 (m, 1H); 4.74-4.86 (m, 1H); 6.92 (br. s., 2H); 6.95 (br. s., 1H); 7.02 (br. s., 2H); 7.21 (t, 2H); 7.38 (s, 1H); 7.64 (br. s., 2H).

The following compounds of formula (IId) were prepared using a similar procedure to that described in Description 22 starting from 1,1-dimethylethyl (2S,5R)-2-(aminocarbonyl)-5-(4-hydroxyphenyl)-1-pyrrolidinecarboxylate (D13) and using the appropriate boronic acid under Condition A.

(IId)

| No. | R⁸ | Characterization |
|---|---|---|
| D23 | 4-cyanophenyl | R$_t$ (HPLC) 5.29 min; ¹H-NMR (400 MHz, DMSO-d₆) δ ppm: 1.10 (s, 9H); 1.79 (br. s., 1H); 1.93 (br. s., 1H); 2.03-2.13 (m, 1H); 2.19-2.30 (m, 1H); 4.62-4.77 (m, 1H); 4.81-4.92 (m, 1H); 6.97 (br. s., 1H); 7.06 (br. s., 4H); 7.41 (s, 1H); 7.74 (br. s., 2H); 7.83 (d, 2H). |

-continued

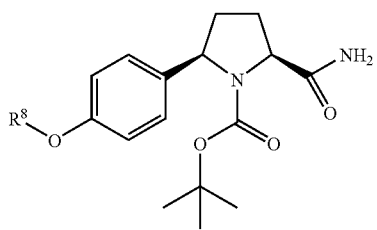

(IId)

| No. | R⁸ | Characterization |
|---|---|---|
| D24 | phenyl | R$_t$ (HPLC) 5.51 min; MS: (ES/+) 405 m/z: [M + Na⁺]. C22H26N2O4 requires 382. ¹H-NMR (400 MHz, CHCl3-d) δ (ppm): 1.24 (s, 9H); 1.59-1.81 (m, 2H); 1.97 (br. s., 1H); 2.25-2.39 (m, 1H); 4.59-4.76 (m, 1H); 5.34-5.45 (m, 1H); 6.93-7.03 (m, 3H); 7.17-7.38 (m, 8H). |
| D25 | 3-fluorophenyl | MS: (ES/+) 423 m/z: [M + Na⁺]. C22H25FN2O4 requires 400. |

Description 26: 1,1-Dimethylethyl (2S,5R)-2-(aminocarbonyl)-5-{4-[(2-cyanophenyl)oxy]phenyl}-1-pyrrolidinecarboxylate (D26)

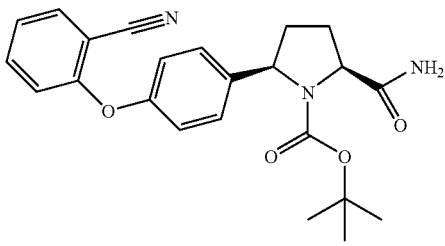

A solution of 1,1-dimethylethyl (2S,5R)-2-(aminocarbonyl)-5-(4-hydroxyphenyl)-1-pyrrolidinecarboxylate (D13, 50 mg, 0.163 mmol), 2-fluorobenzonitrile (40 mg, 0.326 mmol) and K₂CO₃ (34 mg, 0.245 mmol) in DMF (1 ml) was heated under microwave irradiation for 30 min at 120° C. Then water and ethyl acetate were added to the mixture. The organic layer was washed with ice cold brine. The solution was dried over Na₂SO₄ and the solvent removed under reduced pressure. The crude material was purified by chromatography on silica gel using cyclohexanes/ethyl acetate (75:25) to afford the title compound (50 mg, 75%); R$_f$(cyclohexanes:ethyl acetate=1:1): 0.10; R$_t$ (HPLC) 5.17 min.; MS: (ES/+) m/z: 430 [M+Na⁺], C23H25N3O4 requires 407.

Description 27: (5S)-5-{4-[(Phenylmethyl)oxy]phenyl}-L-proline (D27)

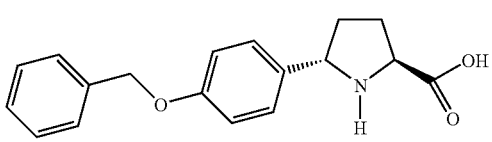

The title compound was synthesized following a similar procedure as set out earlier in Description 10 starting from methyl (5S)-5-{4-[(phenylmethyl)oxy]phenyl}-L-prolinate (D9, 600 mg, 1.92 mmol); Rt (HPLC): 3.66 min; MS: (ES/−) m/z: 296 [M−H]; MS: (ES/+) m/z: 298 [M+H], C18H19NO3 requires 297.

Description 28: (5S)-1-{[(1,1-Dimethylethyl)oxy]carbonyl}-5-{4-[(phenylmethyl)oxy]phenyl}-L-proline (D28)

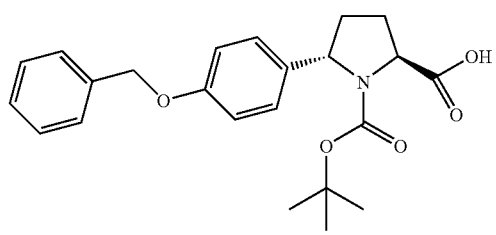

The title compound was synthesized (695 mg, 90% over two steps) a similar procedure as set out earlier in Description 11 starting from ((5S)-5-{4-[(phenylmethyl)oxy]phenyl}-L-proline (D27). The crude material may be used without any further purification in the next step; R$_t$ (HPLC): 5.72 min; MS: (ES/−) m/z: 396 [M−H]; MS: (ES/+) m/z: 420 [M+Na⁺], C23H27NO5 requires 397, ¹H NMR (400 MHz, DMSO-d6) δ (ppm): 12.70-12.42 (br. s, 1H); 7.47-7.42 (m, 2H); 7.42-7.35 (m, 2H); 7.35-7.29 (m, 1H); 7.13-7.07 (m, 2H); 6.98-6.92 (m, 2H); 5.08 and 5.06 (s,s, 2H); 4.96-4.91 and 4.86-4.81 (m, m, 1H); 4.44-4.40 and 4.39-4.34 (m, m, 1H); 2.36-2.13 (m, 2H); 1.90-1.80 (m, 1H); 1.69-1.57 (m, 1H); 1.33 and 1.09 (s,s, 9H).

Description 29: 1,1-Dimethylethyl (2S,5S)-2-(aminocarbonyl)-5-{(4-[(phenylmethyl)oxy]phenyl}-1-pyrrolidinecarboxylate (D29)

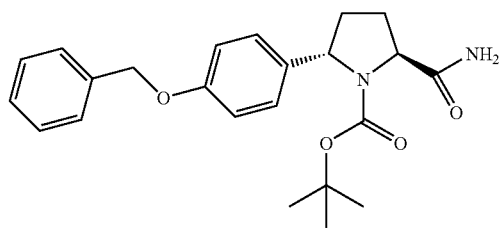

The title compound was synthesized (600 mg, 87%) following a similar procedure as set out earlier in Description 12 starting from (5S)-1-{[(1,1-dimethylethyl)oxy]carbonyl}-5-{4-[(phenylmethyl)oxy]phenyl}-L-proline (D28, 690 mg, crude material); R$_t$ (HPLC): 5.23 min; MS: (ES/+) m/z: 419 [M+Na⁺], C23H28N2O4 requires 396.

Description 30: 1,1-Dimethylethyl (2S,5S)-2-(aminocarbonyl)-5-(4-hydroxyphenyl)-1-pyrrolidinecarboxylate (D30)

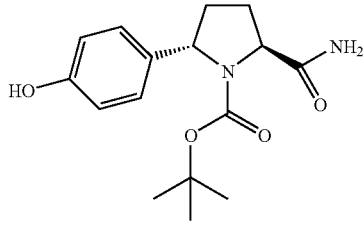

The title compound was synthesized (400 mg, 94%) following a similar procedure as set out earlier in Description 13 starting from 1,1-dimethylethyl (2S,5S)-2-(aminocarbonyl)-5-{4-[(phenylmethyl)oxy]phenyl}-1-pyrrolidinecarboxylate (D29, 550 mg, 1.38 mmol); Rt (HPLC): 3.14 min; MS: (ES/+) m/z: 329 [M+Na$^+$], C16H22N2O4 requires 306; $^1$H NMR (400 MHz, DMSO-d6) δ (ppm): 9.21 (br. s, 1H); 7.40-7.30 (br. s, 1H); 6.96-6.90 (m, 2H); 6.90-6.84 (br. s, 1H); 6.71-6.64 (m, 2H); 4.90 and 4.80 (d, d, 1H); 4.32 and 4.25 (d, d, 1H); 2.37-2.02 (m, 2H); 1.78-1.70 (m, 1H); 1.61-1.46 (m, 1H); 1.32 and 1.09 (s,s, 9H).

Description 31: 1,1-Dimethylethyl (2S,5S)-2-(aminocarbonyl)-5-(4-{[(2-fluorophenyl)methyl]oxy}phenyl)-1-pyrrolidinecarboxylate (D31)

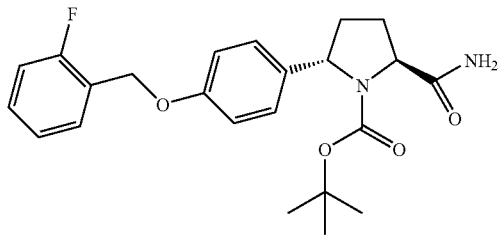

1-(Bromomethyl)-2-fluorobenzene (30 µl, 0.244 mmol) was added to a solution of 1,1-dimethylethyl (2S,5S)-2-(aminocarbonyl)-5-(4-hydroxyphenyl)-1-pyrrolidinecarboxylate (D30, 50 mg, 0.163 mmol) and potassium carbonate (34 mg, 0.244 mmol) in acetonitrile (0.5 ml). The mixture was stirred overnight at room temperature. Then ethyl acetate (20 mL) and water (10 mL) were added. The organic phase was dried over Na$_2$SO$_4$, filtered and evaporated under reduced pressure. The crude material was purified by chromatography on silica gel using cyclohexane/ethyl acetate (7:3 to 6:4) to afford the title compound (65 mg, 97%); R$_f$ (cyclohexane:ethyl acetate=7:3): 0.19; MS: (ES/+) m/z: 437 [M+Na$^+$], C23H27FN2O4 requires 414; R$_t$ (HPLC): 5.28 min; $^1$H NMR (400 MHz, DMSO-d$_6$) δ (ppm): 7.54-7.44 (m, 1H), 7.40-7.27 (m, 2H), 7.24-7.11 (m, 2H), 7.06-6.98 (m, 2H), 6.96-6.79 (m, 3H), 5.10-5.00 (m, 2H), 4.91 and 4.81 (d, d, 1H), 4.29 and 4.24 (d, d, 1H), 2.35-2.18 (m, 1H), 2.17-1.97 (m, 1H), 1.78-1.62 (m, 1H), 1.58-1.43 (m, 1H), 1.28 and 1.03 (s, s, 9H).

Description 32: 1-(1,1-Dimethylethyl) 2-ethyl (2R)-5-oxo-1,2-pyrrolidinedicarboxylate (D32)

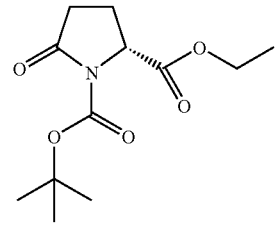

The title compound was synthesized (14 g, 71%) following a similar procedure as set out earlier in Description 5 starting from commercially available ethyl 5-oxo-D-prolinate (12 g, 75.6 mmol); R$_f$ (cyclohexane:ethyl acetate=7:3): 0.25; R$_t$ (HPLC) 3.94 min; $^1$H NMR (400 MHz, DMSO-d6) δ (ppm): 4.61 (dd, 1H); 4.25 (q, 2H); 2.58-2.69 (m, 1H); 2.44-2.55 (m, 1H); 2.26-2.38 (m, 1H); 2.00-2.08 (m, 1H); 1.50 (s, 9H); 1.31 (t, 3H).

Description 33: Ethyl (2R)-2-({[(1,1-dimethylethyl)oxy]carbonyl}amino)-5-oxo-5-{4-[(phenylmethyl)oxy]phenyl}pentanoate (D33)

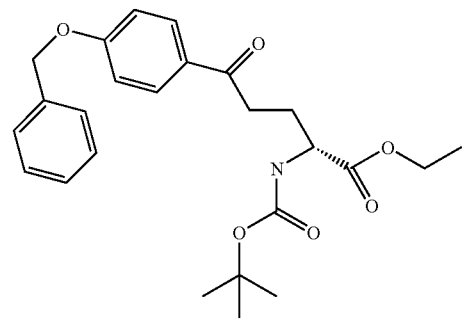

The title compound was synthesized (2.9 g, 16%) following a similar procedure as set out earlier in Description 6 starting from 1-(1,1-dimethylethyl) 2-ethyl (2R)-5-oxo-1,2-pyrrolidinedicarboxylate (D32, 10.5 g 40.8 mmol) and 4-iodophenyl phenylmethyl ether (13.34 g, 43 mmol); Rt (HPLC): 6.37 min; MS: (ES/+) 464 m/z: [M+Na$^+$], C25H31NO6 requires 441; $^1$H NMR (400 MHz, DMSO-d6) δ (ppm): 7.92 (d, 2H); 7.29-7.45 (m, 5H); 6.99 (d, 2H); 5.18 (bs, 1H); 5.12 (s, 2H); 4.29-4.4 (bm, 1H); 4.20 (q, 2H); 2.94-3.16 (m, 2H); 2.22-2.33 (m, 1H); 2.00-2.15 (m, 1H); 1.39 (s, 9H); 1.28 (t, 3H).

Description 34: Ethyl (2R)-5-{4-[(phenylmethyl)oxy]phenyl}-3,4-dihydro-2H-pyrrole-2-carboxylate (D34)

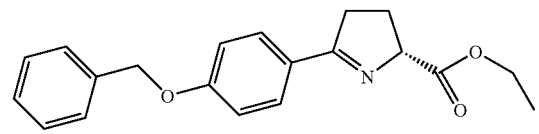

The title compound was synthesized following a similar procedure as set out earlier in Description 7 starting from ethyl (2R)-2-({[(1,1-dimethylethyl)oxy]carbonyl}amino)-5-oxo-5-{4-[(phenylmethyl)oxy]phenyl}pentanoate (D33, 2.9 g, 6.57 mmol). The crude material may be used without any further purification in the next step; $R_t$ (HPLC): 3.80 min; MS: (ES/+) 324 m/z: [MH+], C20H21NO3 requires 323.

Description 35: Ethyl (5S)-5-{4-[(phenylmethyl)oxy]phenyl}-D-prolinate (D35)

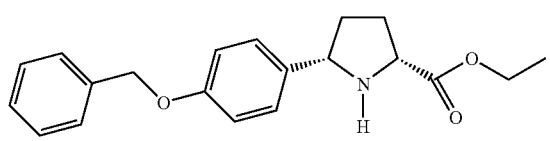

The title compound was synthesized (1.84 g, 86% over two steps) following a similar procedure as set out earlier in Description 8 using the crude material obtained from Description 34; Rt (HPLC): 4.03 min; MS: (ES/+) 326 m/z: [MH+], C20H23NO3 requires 325; $^1$H NMR (500 MHz, CHCl3-d) δ (ppm): 7.30-7.47 (m, 7H), 6.96 (d, 2H), 5.06 (s, 2H), 4.23 (q, 2H), 4.15 (dd, 1H), 3.90 (dd, 1H), 2.17-2.28 (m, 1H), 2.07-2.17 (m, 2H), 1.61-1.76 (m, 1H), 1.31 (t, 3H).

Description 36: (5S)-5-{4-[(Phenylmethyl)oxy]phenyl}-D-proline (D36)

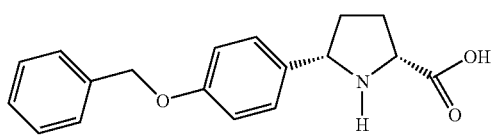

The title compound was synthesized following a similar procedure as set out earlier in Description 10 starting from ethyl (5S)-5-{4-[(phenylmethyl)oxy]phenyl}-D-prolinate (D35, 340 mg, 1.045 mmol); $R^t$ (HPLC): 3.62 min; MS: (ES/+) 298 m/z: [MH+], C18H19NO3 requires 297.

Description 37: (5S)-1-{[(1,1-Dimethylethyl)oxy]carbonyl}-5-{4-[(phenylmethyl)oxy]phenyl}-D-proline (D37)

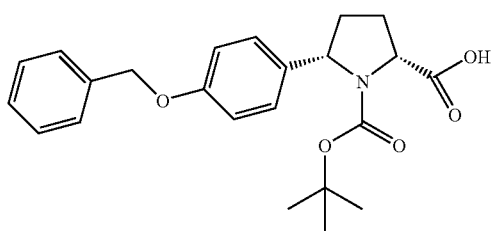

The title compound was synthesized (440 mg, quant. over two steps) following a similar procedure as set out earlier in Description 11 starting from (5S)-5-{4-[(phenylmethyl)oxy]phenyl}-D-proline (D36); Rt (HPLC): 5.77 min; MS: (ES/+) 420 m/z: [M+Na+], C23H27NO5 requires 397; $^1$H-NMR (500 MHz, DMSO-$d_6$) δ (ppm): 12.55 (br.s., 1H); 6.65-6.78 (m, 7H); 6.95 (d, 2H); 5.10 (s, 2H); 4.60-4.84 (m, 1H); 4.23 (m, 1H); 2.10-2.30 (m, 2H); 1.63-1.95 (m, 2H); 1.05-1.39 (m, 9H).

Description 38: 1,1-Dimethylethyl (2R,5S)-2-(aminocarbonyl)-5-{4-[(phenylmethyl)oxy]phenyl}-1-pyrrolidinecarboxylate (D38)

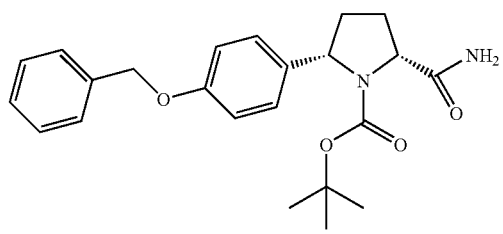

The title compound was synthesized (250 mg, 56%) following a similar procedure as set out earlier in Description 12 starting from (5S)-1-{[(1,1-dimethylethyl)oxy]carbonyl}-5-{4-[(phenylmethyl)oxy]phenyl}-D-proline (D37, 440 mg, 1.11 mmol); Rt (HPLC): 5.52 min; MS: (ES/+) 419 m/z: [M+Na+], C23H28N2O4 requires 396.

Description 39: 1,1-Dimethylethyl (2R,5S)-2-(aminocarbonyl)-5-(4-hydroxyphenyl)-1-pyrrolidinecarboxylate (D39)

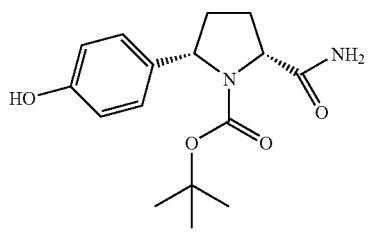

The title compound was synthesized (135 mg, quant.) following a similar procedure as set out earlier in Description 13 starting from 1,1-dimethylethyl (2R,5S)-2-(aminocarbonyl)-5-{4-[(phenylmethyl)oxy]phenyl}-1-pyrrolidinecarboxylate (D38, 175 mg, 0.44 mmol); Rt (HPLC): 3.63 min; MS: (ES/+) m/z: 329 [M+Na+]. C16H22N2O4 requires 306; $^1$H NMR (300 MHz, $d_6$-DMSO) δ (ppm): 9.15 (bs, 1H); 7.40 (bm, 2H); 7.30 (s, 1H); 6.90 (s, 1H); 6.65 (d, 2H); 4.50-4.80 (m, 1H); 4.05-4.28 (m, 1H); 2.07-2.24 (m, 1H); 1.95-2.07 (m, 1H); 1.60-1.89 (m, 2H); 1.00-1.45 (m, 9H).

Description 40: 1,1-Dimethylethyl (2R,5S)-2-(aminocarbonyl)-5-(4-{[(2-fluorophenyl)methyl]oxy}phenyl)-1-pyrrolidinecarboxylate (D40)

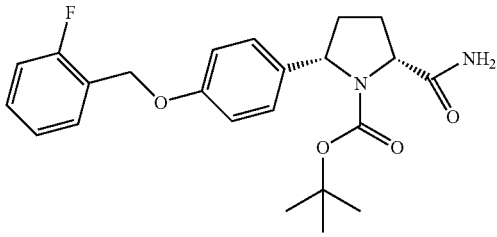

The title compound was synthesized (145 mg, 79%) following a similar procedure as set out earlier in Description 14 starting from 1,1-dimethylethyl (2R,5S)-2-(aminocarbonyl)-5-(4-hydroxyphenyl)-1-pyrrolidine carboxylate (D39, 130 mg, 0.44 mmol) and 1-(bromomethyl)-2-fluorobenzene (166 mg, 0.88 mmol); Rt (HPLC) 5.55; MS: (ES/+) 437 m/z: [M+Na$^+$], C23H27FN2O4 requires 414; $^1$H NMR (300 MHz, DMSO-d$_6$) δ (ppm): 7.48-7.63 (m, 3H); 4.30-4.45 (m, 2H); 4.18-4.29 (m, 2H); 6.90-7.06 (m, 3H); 5.10 (s, 2H); 4.56-4.82 (m, 1H); 4.10-4.18 (m, 1H); 2.12-2.26 (m, 1H); 1.98-2.12 (m, 1H); 1.60-1.95 (m, 2H); 0.98-1.42 (m, 9H).

Description 41: 4-Bromo-3-fluorophenyl (2-fluorophenyl)methyl ether (D41)

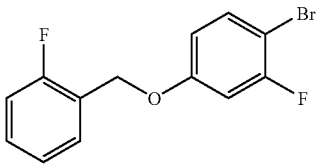

A solution of 4-bromo-3-fluorophenol (5 g, 25 mmol), 2-fluorobenzylbromide (4.94 g, 26 mmol) and potassium carbonate (5.39 g, 39 mmol) was stirred at room temperature for 6 h. The solvent was evaporated, the residue taken up in water and extracted with ethyl acetate. The combined organic layers were dried over Na$_2$SO$_4$, filtered and evaporated under reduced pressure, affording the title compound (8.11 g) as a white solid; R$_t$ (HPLC) 6.31 min.

Description 42: Methyl (2S)-2-({[(1,1-dimethylethyl)oxy]carbonyl}amino)-5-(2-fluoro-4-{[(2-fluorophenyl)methyl]oxy}phenyl)-5-oxopentanoate (D42)

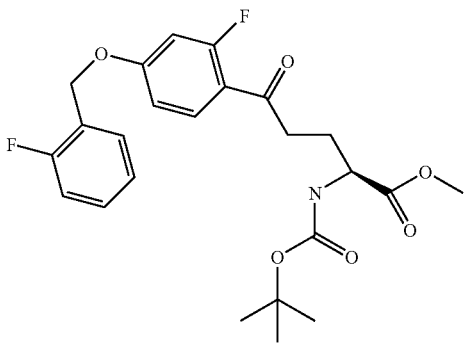

To a solution of 4-bromo-3-fluorophenyl (2-fluorophenyl) methyl ether (D41, 500 mg, 1.67 mmol) and TMEDA (178 mg, 1.53 mmol) in dry THF (7 ml) at −78° C. under nitrogen atmosphere was added n-butyllithium 1.6M solution in hexanes (1 ml, 1.6 mmol) dropwise. The resulting suspension was stirred at −78° C. for 15 minutes and then it was added dropwise to a solution of 1-(1,1-dimethylethyl) 2-methyl (2S)-5-oxo-1,2-pyrrolidinedicarboxylate (D5, 338 mg, 1.39 mmol) in dry THF (2 ml). The mixture was stirred at −78° C. for 1 h, then it was quenched with a saturated ammonium chloride aqueous solution. The phases were separated and the organic layer was washed with brine, dried over Na$_2$SO$_4$, filtered, and evaporated under reduced pressure. The resulting residue was purified by chromatography on silica gel eluting with cyclohexane/ethylacetate (9:1 to 85:15) affording the title compound as a white solid (254 mg, 39%); $^1$H NMR (300 MHz, CDCl$_3$-d) δ (ppm): 8.00-7.80 (m, 1H); 7.53-7.42 (m, 1H); 7.42-7.25 (m, 1H); 7.23-7.05 (m, 2H); 6.90-6.80 (m, 1H); 6.75-6.65 (m, 1H); 5.18 (s, 2H); 4.50-4.30 (m, 1H); 3.71 (s, 3H); 3.18-2.85 (m, 2H); 2.40-2.20 (m, 1H); 2.15-1.90 (m, 1H); 1.40 (s, 9H).

Description 43: Methyl (2S)-5-(2-fluoro-4-{[(2-fluorophenyl)methyl]oxy}phenyl)-3,4-dihydro-2H-pyrrole-2-carboxylate (D43)

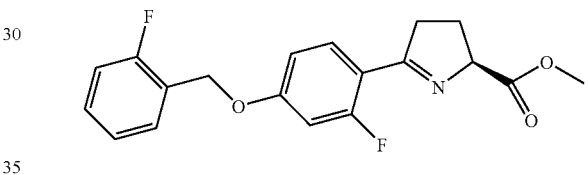

The title compound was synthesized following Description 7 from methyl (2S)-2-({[(1,1-dimethylethyl)oxy]carbonyl}amino)-5-(2-fluoro-4-{[(2-fluorophenyl)methyl]oxy}phenyl)-5-oxopentanoate (D42, 250 mg, 0.54 mmol). The crude material was used in the next step without any further purification; R$_t$ (HPLC): 3.84 min; MS: (ES/+) 346 m/z: [MH$^+$]. C19H17F2NO3 requires 345.

Description 44: Methyl (5R)-5-(2-fluoro-4-{[(2-fluorophenyl)methyl]oxy}phenyl)-L-prolinate (D44)

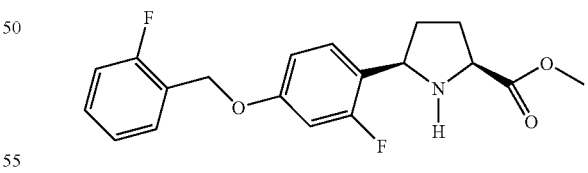

The title compound was synthesized (150 mg, 80% over 2 steps) following Description 8 from methyl (2S)-5-(2-fluoro-4-{[(2-fluorophenyl)methyl]oxy}phenyl)-3,4-dihydro-2H-pyrrole-2-carboxylate (D43, as crude material from description 43). In addition, to the procedure of Description 8, a further SCX cartridge purification was performed; R$^t$ (HPLC): 3.91 min; $^1$H NMR (500 MHz, CDCl$_3$-d) δ (ppm): 7.45-7.58 (m, 2H); 7.27-7.38 (m, 1H); 7.15 (t, 1H); 7.08 (t, 1H); 6.79 (d, 1H); 6.70 (d, 1H); 5.10 (s, 2H); 4.47 (dd, 1H); 3.96 (dd, 1H); 3.78 (s, 3H); 2.17-2.28 (m, 2H); 2.05-2.16 (m, 1H); 1.70-1.80 (m, 1H).

Description 45: (5R)-5-(2-Fluoro-4-{[(2-fluorophenyl)methyl]oxy}phenyl)-L-proline (D45)

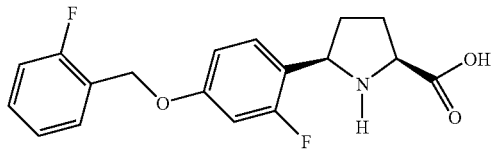

The title compound was synthesized following Description 10 from methyl (5R)-5-(2-fluoro-4-{[(2-fluorophenyl)methyl]oxy}phenyl)-L-prolinate (D44, 150 mg, 0.43 mmol); $R_t$ (HPLC): 3.76 min; MS: (ES/−) m/z: 332 [M−H], $C_{18}H_{17}F_2NO_3$ requires 333.

Description 46: (5R)-1-{[(1,1-Dimethylethyl)oxy]carbonyl}-5-(2-fluoro-4-{[(2-fluorophenyl)methyl]oxy}phenyl)-L-proline (D46)

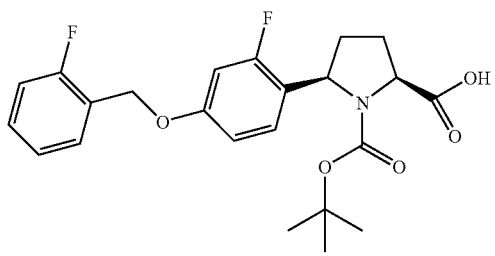

The title compound was synthesized (260 mg, quant.) following Description 11 from (5R)-5-(2-fluoro-4-{[(2-fluorophenyl)methyl]oxy}phenyl)-L-proline (D45). The crude material may be used without further purification in the next step; $R_t$ (HPLC): 6.04 min; MS: (ES/−) m/z: 432 [M−H]; MS: (ES/+) m/z: 456 [M+Na⁺], $C_{23}H_{25}F_2NO_5$ requires 433.

Description 47: 1,1-dimethylethyl (2S,5R)-2-(aminocarbonyl)-5-(2-fluoro-4-{[(2-fluorophenyl)methyl]oxy}phenyl)-1-pyrrolidinecarboxylate (D47)

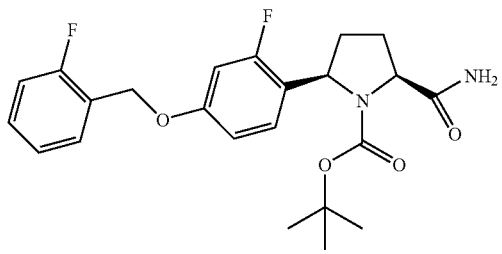

The title compound was synthesized (130 mg, 70% over three steps) following Description 12 from (5R)-1-{[(1,1-dimethylethyl)oxy]carbonyl}-5-(2-fluoro-4-{[(2-fluorophenyl)methyl]oxy}phenyl)-L-proline (D46, 260 mg crude material, max. 0.43 mmol); $R_t$ (HPLC): 5.73 min; MS: (ES/+) m/z: 455 [M+Na⁺], $C_{23}H_{26}F_2N_2O_4$ requires 432.

Description 48: 3-bromophenyl phenylmethyl ether (D48)

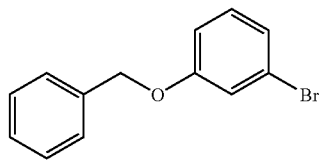

The title compound was synthesized (4.8 g, quant.) following Description 41 from 3-bromophenol (3 g, 17.3 mmol) and benzylbromide (2.1 ml); $R_t$ (HPLC): 6.42 min.

Description 49: Methyl (2S)-2-({[(1,1-dimethylethyl)oxy]carbonyl}amino)-5-oxo-5-{3-[(Phenylmethyl)oxy]phenyl}pentanoate (D49)

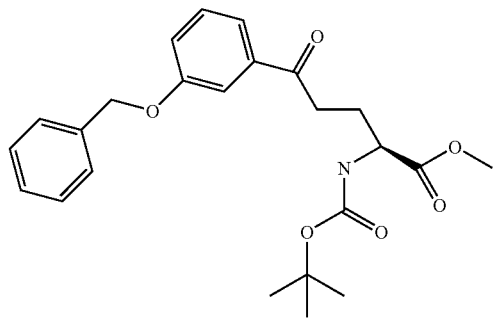

The title compound was synthesized (420 mg, 6%) following Description 6 from 1-(1,1-dimethylethyl) 2-methyl (2S)-5-oxo-1,2-pyrrolidinedicarboxylate (D5, 3.69 g, 15.2 mmol) and 3-bromophenyl phenylmethyl ether (D48); $R_t$ (HPLC): 6.2 min.

Description 50: Methyl (2S)-5-{3-[(phenylmethyl)oxy]phenyl}-3,4-dihydro-2H-pyrrole-2-carboxylate (D50)

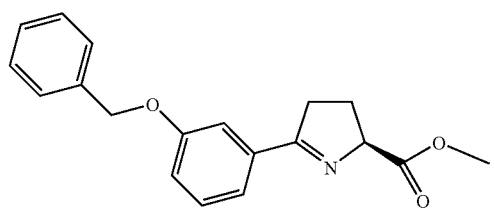

The title compound was synthesized (666 mg) following Description 7 from methyl (2S)-2-({[(1,1-dimethylethyl)oxy]carbonyl}amino)-5-oxo-5-{3-[(phenylmethyl)oxy]phenyl}pentanoate (D49, 420 mg, 1 mmol). The crude material may be used in the next step without further purification; $R_t$ (HPLC): 3.99 min.

Description 51: Methyl (5R)-5-{3-[(phenylmethyl)oxy]phenyl}-L-prolinate (D51)

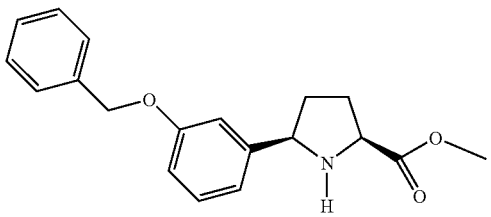

The title compound was synthesized (270 mg, 87%) following Description 8 from methyl (2S)-5-{3-[(phenylmethyl)oxy]phenyl}-3,4-dihydro-2H-pyrrole-2-carboxylate (D50, crude material from description 50, 666 mg); $R_t$ (HPLC): 3.70 min; MS: (ES/+) m/z: 312 [MH$^+$], C19H21NO3 requires 311; $^1$H NMR (400 MHz, CHCl3-d) δ (ppm): 7.41 (d, 2H); 7.35 (t, 2H); 7.26-7.32 (m, 1H); 7.19-7.25 (m, 1H); 7.09 (t, 1H); 7.00 (d, 1H); 6.84 (dd, 1H); 5.04 (s, 2H); 4.17 (dd, 1H); 3.94 (dd, 1H); 3.74 (s, 3H); 2.01-2.24 (m, 3H); 1.63-1.75 (m, 1H).

Description 52: 1-(1,1-dimethylethyl) 2-methyl (2S,5R)-5-{3-[(phenylmethyl)oxy]phenyl}-1,2-pyrrolidinedicarboxylate (D52)

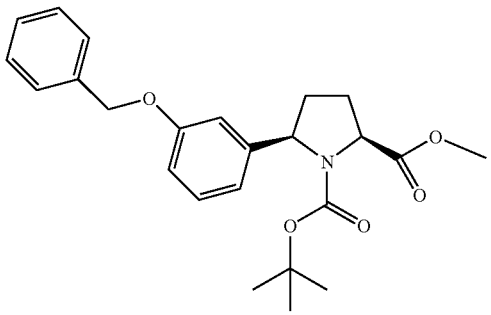

The title compound was synthesized (2.69, quant.) following Description 11 from methyl-(5R)-5-{3-[(phenylmethyl)oxy]phenyl}-L-prolinate (D51, 1.66 g, 5.33 mmol). The crude material was used in the next step without further purification; $R_t$ (HPLC): 6.54 min.

Description 53: (5R)-1-{[(1,1-dimethylethyl)oxy]carbonyl}-5-{3-[(phenylmethyl)oxy]phenyl}-L-proline (D53)

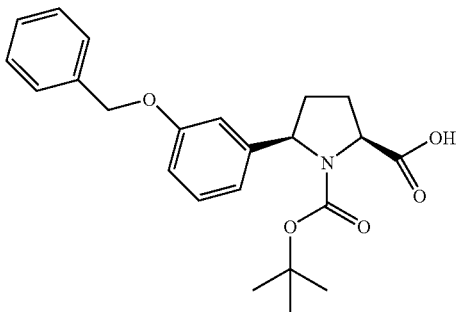

The title compound was synthesized (400 mg, 99%) following Description 11 from 1-(1,1-dimethylethyl) 2-methyl (2S,5R)-5-{3-[(phenylmethyl)oxy]phenyl}-1,2-pyrrolidinedicarboxylate (D52, 600 mg, crude material); $R_t$ (HPLC): 5.81 min.

Description 54: 1,1-dimethylethyl (2S,5R)-2-(aminocarbonyl)-5-{3-[(phenylmethyl)oxy]phenyl}-1-pyrrolidinecarboxylate (D54)

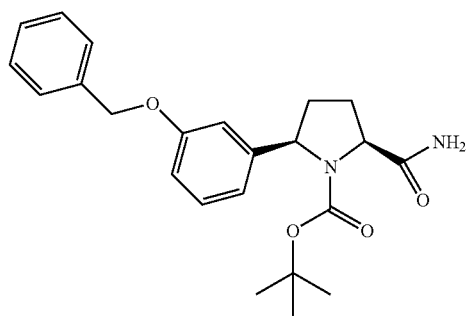

The title compound was synthesized (430 mg, quant.) following Description 12 from (5R)-1-{[(1,1-dimethylethyl)oxy]carbonyl}-5-{3-[(phenylmethyl)oxy]phenyl}-L-proline (D53, 430 mg, 1.08 mmol); $R_t$ (HPLC): 5.54 min; MS: (ES/+) m/z: 419 [M+Na$^+$], C23H28N2O4 requires 396.

Description 55: 1-[(4-bromophenoxy)methyl]-2-fluorobenzene (D55)

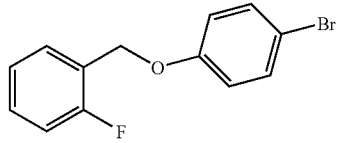

Procedure 1: To a solution of 4-bromophenol (502.08 g) dissolved in acetone (7322 mL) was added K$_2$CO$_3$ (570 g) and then benzylbromide (523 g). The mixture was heated under reflux for 2 hrs. The reaction mixture was then cooled at 25° C., filtered and the filter cake was washed with MTBE (1046 mL). The combined filtrate was concentrated to 1000 mL and MTBE (4184 mL) were added. The mixture was washed with an aqueous 1M NaOH solution (1464 mL), then with brine (1300 mL) and the organic phase was concentrated to dryness. THF (1300 mL) was added and the solvent was removed under reduced pressure to afford the title compound (902.1 g); $^1$H NMR (400 MHz, DMSO-d6) δ (ppm): 7.54 (td, 1H); 7.46 (d, 2H); 7.42 (m, 1H); 7.23 (m, 2H); 7.01 (d, 2H); 5.13 (s, 2H).

D55 was also obtained as follows:

Procedure 2: A stirred mixture of 4-bromophenol (19.22 g, 111 mmol), orthofluorobenzyl bromide (20 g, 105.8 mmol) and potassium carbonate (21.9 g, 158.4 mmol) in acetone (280 ml) was heated at reflux for 6 hours. The reaction mixture was cooled to room temperature and filtered, washing the solid with TBME (40 ml). The combined filtrate and washings were concentrated under vacuum to a final volume of about 40 ml. The resulting solution was diluted with TBME (160 ml) and washed with 1M sodium hydroxide and brine, then concentrated under vacuum to an oil which slowly solidified to give the title compound (28.9 g).

¹H NMR (300 MHz, CHCl3-d). δ (ppm): 5.10 (s, 2H), 6.86 (m, 2H), 7.10 (m, 1H), 7.17 (m, 1H), 7.29 (m, 1H), 7.35 (m, 2H), 7.38 (m, 1H).

Description 56: Methyl (2S)-2-[(tert-butoxycarbonyl)amino]-5-{4-[(2-fluorobenzyl)oxy]phenyl}-5-oxopentanoate (D56)

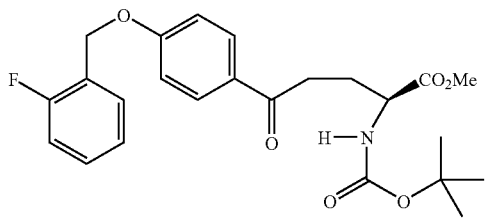

Procedure 1: To a stirred suspension of magnesium metal (90 g) in dry THF (600 mL) under a nitrogen atmosphere at room temperature was added iodine (0.3 g). The mixture was heated to an internal temperature of 64+/−2° C. A solution of 1-[(4-bromophenoxy)methyl]-2-fluorobenzene (D55) (693 g) in THF (1500 mL) was added in two batches. Firstly 45 mL was added. Secondly, the remaining solution (1455 mL) was added dropwise. After addition, the reaction was heated at reflux for 1 h. The reaction mixture was cooled to room temperature. This reaction mixture was then added slowly to a solution of commercially available 1-tert-butyl 2-methyl (2S)-5-oxopyrrolidine-1,2-dicarboxylate (300 g) in THF (1500 mL) cooled to −60° C., maintaining the internal temperature below −60° C. The addition was completed in 2 hours. The reaction mixture was stirred for a further 15 minutes after addition. Isopropyl alcohol (300 mL) was then added dropwise whilst maintaining the temperature below −60° C. A mixture of aqueous saturated ammonium chloride solution/aqueous saturated sodium chloride solution (2/1; 900 mL) was added whilst maintaining the temperature at −50° C. Water (600 mL) was added to dissolve the yellow precipitate. The organic phase was separated and was washed with aqueous 13% NaCl solution (600 mL). The organic phase was concentrated to dryness. EtOAc (1500 mL) was then added and the solution was evaporated under reduced pressure to remove water. The residue was purified by chromatography on silica gel eluting with cyclohexane/ethyl acetate (90:10 to 8:2) to afford the title compound (287 g); ¹H NMR (600 MHz, DMSO-d6) δ (ppm): 7.93 (d, 2H); 7.57 (td, 1H); 7.44 (m, 1H); 7.27 (m, 3H); 7.14 (d, 2H); 5.24 (s, 2H); 4.04 (m, 1H); 3.61 (s, 3H); 3.03 (m, 2H); 1.94 (m, 2H); 1.38 (s, 9H).

D56 was also obtained as follows:
Procedure 2: To a mixture of magnesium turnings (12.79 g. 533 mol), a trace of iodine and 1,2-dibromoethane in THF (86 .ml) at 70-75° C., a solution of (4-bromophenyl (2-fluorophenyl)methyl ether) (D55, 100 g, 355.6 mmol) in THF (216.25 ml) was added over about 2 hours. The mixture was heated for a further 2 hours at 70-75° C. then cooled to room temperature to give a solution of the Grignard reagent. A solution of 1-(1,1-dimethylethyl) 2-methyl (2S)-5-oxo-1,2-pyrrolidinedicarboxylate (43.25 g, 177.8 mmol) in THF (216.25 ml) was cooled to −60° C. and the solution of the Grignard reagent was added over 1 hour, then the mixture was stirred for 3 hours at −60° C. Isopropanol (43.25 ml) was added dropwise, followed by saturated aqueous ammonium chloride (86.5 ml) and brine (43.25 ml), then the mixture warmed to room temperature. Water (173 ml) and 50% acetic acid (50 ml) to pH 6-7, followed by ethyl acetate (129.7 ml). The layers were separated and the aqueous extracted with ethyl acetate (2×129.7 ml). The combined organic layers were washed with brine then concentrated under vacuum. The residue was stirred with hexane (216.2 ml), then the solid was filtered and washed with hexane. To the resulting solid, isopropanol (432.5 ml) was added and the mixture stirred at 45° C. for 15 minutes, then cooled to 5-10° C. and stirred for 2 hours. The solid was filtered, washed with isopropanol and dried to give the title compound as a solid.

1H NMR (300 MHz, CHCl3-d): δ (ppm): 1.42 (s, 9H); 2.04 (m, 1H); 2.28 (m, 1H); 3.03 (m, 2H); 3.74 (s, 3H); 4.37 (m, 1H); 5.19 (b, 1H); 5.20 (s, 2H); 7.02 (d, 2H); 7.11 (t, 1H); 7.17 (t, 1H); 7.33 (m, 1H); 7.48 (t, 1H); 7.94 (d, 2H).

Description 57: methyl (2S)-5-{4-[(2-fluorobenzyl)oxy]phenyl}-3,4-dihydro-2H-pyrrole-2-carboxylate (D57)

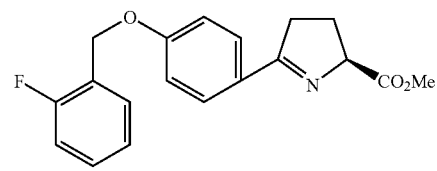

Procedure 1: To a solution of methyl (2S)-2-({[(1,1-dimethylethyl)oxy]carbonyl}amino)-5-(4-{[(2-fluorophenyl)methyl]oxy}phenyl)-5-oxopentanoate (D56) (243 g) in dry DCM (2430 mL) at 0° C. was added TFA (461 mL) dropwise. The mixture was allowed to warm to room temperature and stirred for 3 hrs. Solvent and the excess TFA were removed under vacuum and the resulting dark oil was stripped with EtOAc (2×1215 mL) and left overnight under a high vacuum. The title compound (392 g) was obtained as a red oil and used in the following step without any further purification; ¹H NMR (400 MHz, DMSO-d6) δ (ppm): 8.16 (m, 2H); 7.60 (td, 1H); 7.46 (m, 1H); 7.34 (m, 2H); 7.27 (m, 2H); 5.32 (s, 2H); 5.25 (m, 1H); 3.77 (s, 3H); 3.57 (m, 2H); 2.60 (m, 1H); 2.34 (m, 1H).

D57 was also obtained as follows:
Procedure 2: A solution of methyl (2S)-2-({[(1,1-dimethylethyl)oxy]carbonyl}amino)-5-(4-{[(2-fluorophenyl)methyl]oxy}phenyl)-5-oxopentanoate (D56, 46 g, 103 mmol) in DCM (437 ml) was treated dropwise with trifluoroacetic acid (87.4 ml) at 0-5° C., then warmed to room temperature and stirred for 3 hours. The solution was cooled to 0-5° C. and sodium hydroxide solution added to a final pH of about 7. The aqueous layer was separated and extracted with DCM (13 ml), then the combined organic layers were washed with water, dried over sodium sulphate, then concentrated under vacuum to give the title compound as a solid (33.3 g).

¹H NMR (300 MHz, CHCl3-d): δ (ppm): 2.35 (m, 2H); 2.95 (m, 1H); 3.12 (m, 1H); 3.78 (s, 3H); 4.89 (dd, 1H); 5.18 (s, 2H); 7.00 (d, 2H); 7.10 (m, 1H); 7.16 (m, 1H); 7.29 (m, 1H); 7.5 (t, 1H); 7.85 (d, 2H).

Description 58: Methyl (5R)-5-{4-[(2-fluorobenzyl)oxy]phenyl}-L-prolinate (D58)

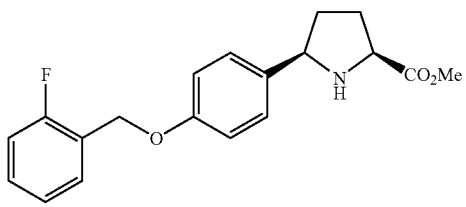

Procedure 1: Methyl (2S)-5-{4-[(2-fluorobenzyl)oxy]phenyl}-3,4-dihydro-2H-pyrrole-2-carboxylate (D57) (392 g) was dissolved in EtOAc (3160 mL) in a hydrogenation reactor. 5% platinum on carbon (Engelhard code 44379, moisture content ca. 50%, 15.8 g) was added, the reactor filled with hydrogen gas to a pressure of 2 atm and the reaction mixture was stirred for approximately 1.5 hours. The reactor was depressurised and the spent catalyst filtered through Celite, washing through with EtOAc (2×500 mL, then further 200 mL). Aqueous saturated NaHCO$_3$ solution (600 mL) was added to the filtrate, followed by aqueous 13% w/w Na$_2$CO$_3$ solution (up to pH=9, 1000 mL). The mixture was stirred for 10 minutes and phases were then allowed to separate. The aqueous phase was removed and then the organic layer was washed once with brine (600 mL). The resulting solution was concentrated to dryness and the residue was purified by flash chromatography eluting with cyclohexane/ethyl acetate (1:1) to afford the title compound (133 g); $^1$H NMR (600 MHz, DMSO-d6) δ (ppm): 7.55 (dt, 1H); 7.41 (m, 1H); 7.34 (m, 2H); 7.23 (m, 2H); 6.97 (m, 2H); 5.12 (s, 2H); 4.09 (dd, 1H); 3.83 (dd, 1H); 3.66 (s, 3H); 2.97 (bs, 1H); 2.04 (m, 2H); 1.94 (m, 1H); 1.52 (m, 1H).

D58 was also prepared as follows:

Procedure 2: A solution of methyl (2S)-5-(4-{[(2-fluorophenyl)methyl]oxy}phenyl)-3,4-dihydro-2H-pyrrole-2-carboxylate (D57, 34 g, 103.5 mmol) in ethyl acetate (272 ml) was placed in an autoclave and treated with trifluoroacetic acid (7.2 ml). 5% Platinum on carbon catalyst (1.7 g) was transferred as a slurry with ethyl acetate (68 ml) and the reaction was stirred at room temperature under 50 psi hydrogen pressure for 5 hours. The mixture was filtered through Hyflo, washing with ethyl acetate (272 ml), then the filtrate was washed with aq sodium carbonate solution and brine, dried over sodium sulphate, then concentrated under vacuum, and the residue dried to give the title compound as a crude oil (also containing some of the anti isomer), $^1$H NMR (300 MHz, CHCl3-d): δ (ppm): 1.7 (m, 1H); 2.18 (m, 4H); 3.75 (s, 3H); 3.91 (m, 1H); 4.15 (m, 1H); 5.13 (s, 2H); 6.96 (d, 2H); 7.07 (m, 1H); 7.15 (m, 1H); 7.30 (m, 1H); 7.38 (d, 2H); 7.5 (t, 1H).

Description 59: 4-bromo-1-{[(2-fluorophenyl)methyl]oxy}-2-(methyloxy)benzene (D59)

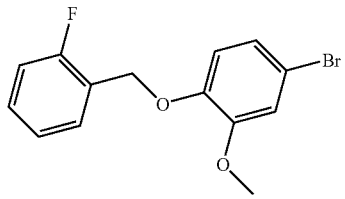

A suspension of 4-bromo-2-(methyloxy)phenol (3.0 g, 14.78 mmol), potassium carbonate (2.99 g, 22.17 mmol) and 2-fluorobenzylbromide (1.78 ml, 14.78 mmol) in acetonitrile (20 ml) was stirred at room temperature overnight. Diethylether was added. The organic phase was then washed was washed with water and 1M NaOH, dried (Na$_2$SO$_4$), filtered and evaporated to afford the title compound (4.388 g, quant.). R$_t$ (HPLC): 6.25 min; $^1$H-NMR (400 MHz, DMSO-d6) δ (ppm): 7.5 (m, 1H), 7.4 (m, 1H), 7.2 (m, 2H), 7.1 (s, 1H), 7.0 (m, 2H), 5.1 (s, 2H), 3.7 (s, 3H).

Description 60: Methyl (2S)-2-({[(1,1-dimethylethyl)oxy]carbonyl}amino)-5-[4-{[(2-fluorophenyl)methyl]oxy}-3-(methyloxy)phenyl]-5-oxopentanoate (D60)

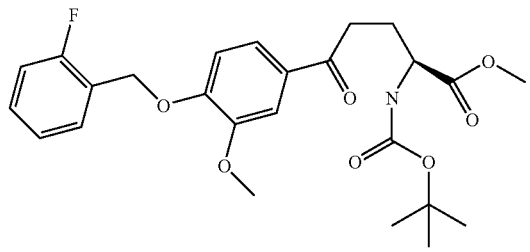

1,2-Dibromethane (106 uL, 232 mg, 1.233 mmol) was added to a suspension of magnesium (300 mg, 12.33 mmol) in dry THF (3 mL). Then a solution of 4-bromo-1-{[(2-fluorophenyl)methyl]oxy}-2-(methyloxy)benzene (D59, 2.40 g, 8.22 mmol), prepared with analogous procedure to that described hereinabove, in dry THF (17 ml) was added dropwise. The mixture was heated under reflux for 1.5 h. The grignard formation was followed via HPLC (Rt(HPLC, 1-fluoro-2-({[2-(methyloxy)phenyl]oxy}methyl)benzene): 5.59 min, Rt (HPLC, D59): 6.24 min). When the reaction stopped, additional 1,2-dibromethane (0.1 eq) was added. After the grignard formation was complete, the mixture was added dropwise to a solution 1-(1,1-dimethylethyl) 2-methyl (2S)-5-oxo-1,2-pyrrolidinedicarboxylate (D5, 1 g, 4.11 mmol) in dry THF (20 ml) at −65° C. Stirring at −65° C. was continued for 3.5 h. Then isopropanol and diethylether were added, the organic layer was washed with aqueous ammonium chloride solution, dried (Na$_2$SO$_4$) and evaporated. The residue was purified with flash chromatography using a cyclohexanes/ethyl acetate (40% to 100%) gradient to afford the title compound (900 mg, 46%). MS: (ES/+) m/z: 376 [M-BOC$^+$], C25H30FNO7 requires 475; UPLC: 0.84 min, m/z: 476 [MH+], $^1$H NMR (400 MHz, DMSO-d6) δ (ppm): 7.6 (m, 2H), 7.4 (m, 2H), 7.3-7.2 (m, 4H), 5.2 (s, 2H), 4.1 (m, 1H), 3.8 (s, 3H), 3.6 (s, 3H), 3.2-3.0 (m, 2H), 2.1-2.0 (m, 1H), 1.9 (m, 1H), 1.4 (s, 9H).

Description 61: Ethyl (2R)-5-{(4-[(phenylmethyl)oxy]phenyl}-3,4-dihydro-2H-pyrrole-2-carboxylate (D61)

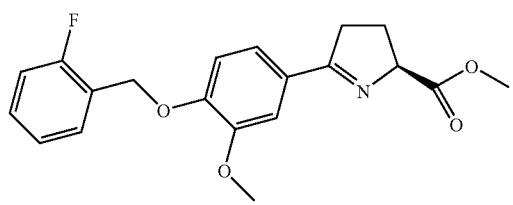

The title compound was synthesized following Description 7 from methyl (2S)-2-({[(1,1-dimethylethyl)oxy]carbonyl}amino)-5-[4-{[(2-fluorophenyl)methyl]oxy}-3-(methyloxy)phenyl]-5-oxopentanoate (D60, 900 mg, 1.892 mmol). The crude material (1.6 g) was used without further purification in the next step. UPLC: Rt=0.60 min, MS: (ES/+) 358 m/z: [MH⁺], C20H20FNO4 requires 357.

Description 62: Methyl (5R)-5-[4-{[(2-fluorophenyl)methyl]oxy}-3-(methyloxy)phenyl]-L-prolinate (D62)

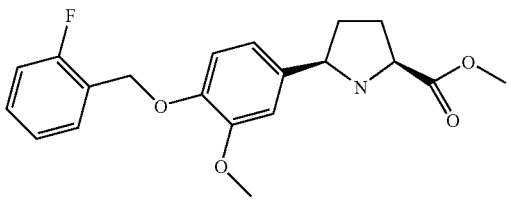

The title compound was synthesized following Description 58 from ethyl (2R)-5-{4-[(phenylmethyl)oxy]phenyl}-3,4-dihydro-2H-pyrrole-2-carboxylate (D61, 1.6 g). The crude material was purified via SCX cartridge to afford the title compound (D62, 605 mg). UPLC: Rt=0.56 min, MS: (ES/+) m/z: 360 [MH⁺], C20H22FNO4 requires 359; $^1$H NMR (400 MHz, DMSO-d6) δ (ppm): 7.5 (m, 1H), 7.4 (m, 1H), 7.2 (m, 2H), 7.1 (s, 1H), 7.0 (m, 1H), 6.9 (m, 1H), 5.1 (s, 2H), 4.1 (m, 1H), 3.8 (m, 1H), 3.7 (s, 3H), 3.6 (s, 3H), 3.0 (bs, 1H), 2.1 (m, 2H), 1.9 (m, 1H), 1.5 (m, 1H).

Description 63: N-[(2-Fluorophenyl)methyl]-4-iodoaniline (D63)

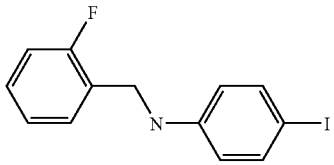

A solution of 4-iodoaniline (1 g, 4.5 mmol), 2-fluorobenzaldehyde (0.48 ml, 0.566 g, 4.5 mmol) and triacetoxyborohydride (1.9 g, 9.0 mmol) in 1,2-dichloroethane (20 ml) was stirred for 4 days at room temperature. After addition of water the mixture was extracted with DCM. The combined organic layers were dried (Na₂SO₄), filtered and evaporated to give the title compound (1.612 g, quant.). The crude material was used without further purification. MS: (ES/+) m/z: 328 [MH⁺], C13H11FIN requires 327; $^1$H NMR (400 MHz, DMSO-d6) δ (ppm): 7.4-7.1 (m, 6H), 6.4 (d, 2H), 4.3 (m, 1H), 2.5 (m, 2H).

Description 64: Methyl (2S)-2-({[(1,1-dimethylethyl)oxy]carbonyl}amino)-4-pentynoate (D64)

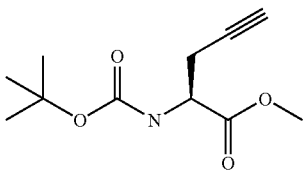

Thionylchloride (16 ml, 26 g, 221 mmol) was added dropwise to a cooled (0° C.) solution of (2S)-2-amino-4-pentynoic acid (5.0 g, 44.18 mmol, commercially) in methanol (dry, 100 ml). After stirring the mixture at room temperature for 5.5 hrs the solvent was evaporated and the residue was taken up in 1,4-dioxane (100 ml) and aqueous saturated NaHCO₃ solution (50 ml). Then BOC₂O (10.1 g, 46.4 mmol) was added and the mixture was stirred overnight at room temperature. Ethyl acetate and aqueous NaHCO₃ solution were added. The separated organic layer was washed with bicarbonate solution, dried (Na₂SO₄), filtrated and evaporated. The resulting crude material was purified by chromatography on silica gel using ethyl acetate/cyclohexanes (1:100 to 3:7) to afford the title compound (7.35 g, 73%); MS: (ES/+) m/z: 250 [MNa]+, C11H17NO4 requires 227. $^1$H-NMR (400 MHz, DMSO-d6) δ (ppm): 7.3 (d, 1H), 4.1 (m, 1H), 2.9 (s, 1H), 2.6-2.5 (m, 2H), 1.4 (s, 9H).

Description 65: Methyl (2S)-2-({[(1,1-dimethylethyl)oxy]carbonyl}amino)-5-(4-{[(2-fluorophenyl)methyl]amino}phenyl)-4-pentynoate (D65)

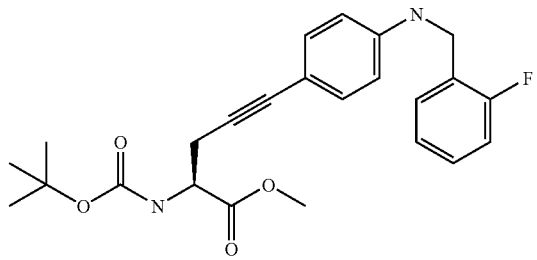

To a stirred solution of methyl (2S)-2-({[(1,1-dimethylethyl)oxy]carbonyl}amino)-4-pentynoate (D64, 365 mg, 1.60 mmol), prepared with analogous procedure to that described hereinabove, N-[(2-fluorophenyl)methyl]-4-iodoaniline (D63, 630 mg, 1.92 mmol) and diethylamine (0.82 ml, 585 mg, 8 mmol) was added CuI (30 mg, 0.08 mmol) and PdCl₂(PPh₃)₂ (56 mg, 0.08 mmol). After stirring at room temperature for 5 h ethyl acetate was added and the solution was extracted with sat. ammonium chloride solution. The organic layer was dried (Na₂SO₄), filtered and evaporated. The resulting crude material was purified by flash chromatography using a cyclohexanes, ethyl acetate gradient (5%40%) on silica gel to afford the title compound (192 mg, 28%); UPLC: 0.88 min, MS: (ES/+) m/z: 427 [MH]+, C24H27FN2O4 requires 426.

Description 66: Methyl (2S)-2-amino-5-(4-{[(2-fluorophenyl)methyl]amino}phenyl)-4-pentynoate (D66)

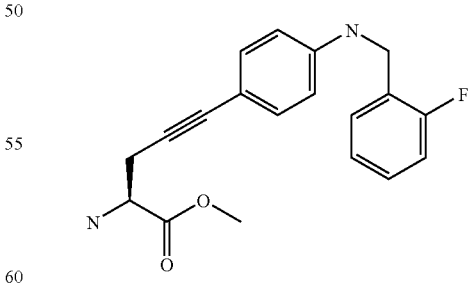

A solution of methyl (2S)-2-({[(1,1-dimethylethyl)oxy]carbonyl}amino)-5-(4-{[(2-fluorophenyl)methyl]amino}phenyl)-4-pentynoate (D65, 192 mg, 0.450 mmol) in DCM containing 5% TFA (10.5 ml) was stirred at room temperature for 4.5 h. Then 28% NH₃ in water was added and the mixture was extracted with DCM. The combined organic layers were dried (Na₂SO₄), filtered and evaporated to afford the title compound (132 mg). The crude product was used unpurified in the next step. UPLC: 0.56 min, MS: (ES/+) m/z: 327 [MH]+, C19H19FN2O2 requires 326.

Description 67: Methyl (2S)-5-(4-{[(2-fluorophenyl)methyl]amino}phenyl)-3,4-dihydro-2H-pyrrole-2-carboxylate (D67)

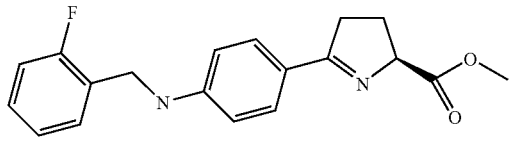

A solution of methyl (2S)-2-amino-5-(4-{[(2-fluorophenyl)methyl]amino}phenyl)-4-pentynoate (D66, 132 mg) and silver triflate (11 mg, 0.045 mmol) was stirred at room temperature 6.5 h. Then silica gel was added and the solvent evaporated. The residue was purified using flash chromatography eluting with a cyclohexanes:ethyl acetate gradient (12%-100%) to afford the title compound (39 mg, 26%). MS: (ES/+) m/z: 327 [MH]+, C19H19FN2O2 requires 326.

Description 68: Methyl (5R)-5-(4-{[(2-fluorophenyl)methyl]amino}phenyl)-L-prolinate (D68)

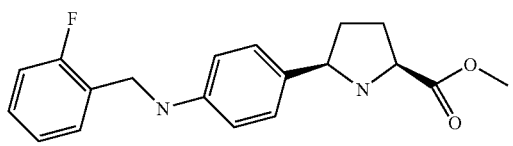

A solution of methyl (2S)-5-(4-{[(2-fluorophenyl)methyl]amino}phenyl)-3,4-dihydro-2H-pyrrole-2-carboxylate (D67, 39 mg, 0.119 mmol) and Pt 5% on carbon in ethyl acetate (10 ml) was stirred under 1 atm of hydrogen for 4.5 h, filtrated over celite and evaporated to afford the title compound (36 mg, 92%). MS: (ES/+) m/z: 329 [MH]+, —C19H21FN2O2 requires 328.

Description 69: 5-bromo-2-{[(2-fluorophenyl)methyl]oxy}benzonitrile (D69)

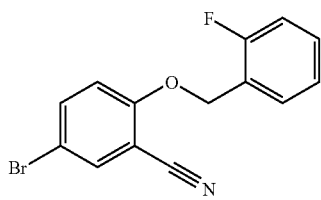

A solution of 5-bromo-2-hydroxybenzonitrile (3.31 g, 16.71 mmol), synthesized as described in *J. Org. Chem.* 1997, 13, 4504-4506, 2-fluorobenzylbromide (commercially available, 2.02 ml, 3.16 g, 16.71 mmol) and potassium carbonate (3.46 g, 25.06 mmol) was stirred overnight at room temperature. Then diethylether was added and the solution was washed with water, 1M NaOH and brine. The organic layer was dried (Na₂SO₄), filtered and evaporated to afford the title compound (4.74 g, 92%). ¹H-NMR (400 MHz, DMSO-d6) δ (ppm): 8.0 (M, 1H), 7.9 (m, 1H), 7.6 (m, 1H), 7.5-7.3 (m, 2H), 7.2 (m, 2H), 5.3 (s, 2H).

Description 70: methyl (2S)-5-(3-cyano-4-{[(2-fluorophenyl)methyl]oxy}phenyl)-2-({[(1,1-dimethylethyl)oxy]carbonyl}amino)-4-pentynoate (D70)

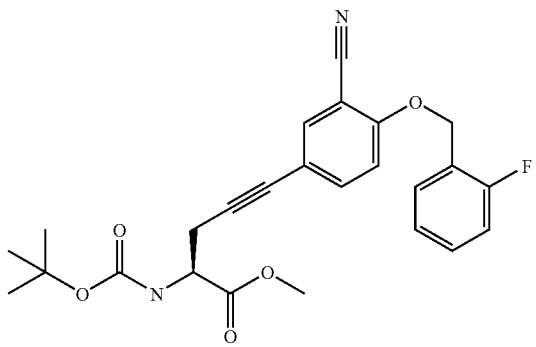

The title compound (65 mg, 32%) was synthesized in an analogous way to that described in Description 65 from 5-bromo-2-{[(2-fluorophenyl)methyl]oxy}benzonitrile (D69, 161 mg, 0.53 mmol). UPLC: Rt=0.86 min, MS: (ES/+) m/z: 453 [MH⁺], C25H25FN2O5 requires 452.

Description 71: methyl (2S)-2-amino-5-(3-cyano-4-{[(2-fluorophenyl)methyl]oxy}phenyl)-4-pentynoate (D71)

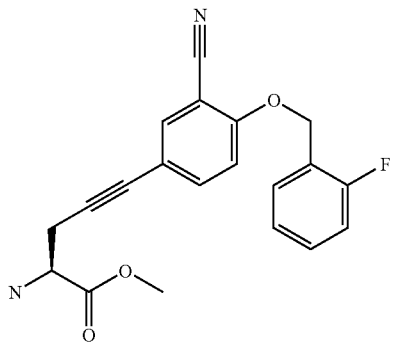

Acetyl chloride (225 ul, 248 mg, 3.16 mmol) was added dropwise to a solution of methyl (2S)-5-(3-cyano-4-{[(2-fluorophenyl)methyl]oxy}phenyl)-2-({[(1,1-dimethylethyl)oxy]carbonyl}amino)-4-pentynoate (D70, 286 mg, 0.631 mmol), prepared with analogous procedure to that described hereinabove, in dry ethyl acetate (10 ml) and dry methanol (2 ml). After stirring at room temperature overnight the solvent was evaporated, water (10 ml) and dioxin (10 ml) were added and the pH was adjusted to 10 using 28% NH₃ in water. The mixture was extracted with DCM. The combined organic layer was dried (Na₂SO₄), filtered and evaporated. The crude product was used in the next step. MS: (ES/+) m/z: 353 [MH⁺], C20H17FN2O3 requires 352.

Description 72: Methyl (2S)-5-(3-cyano-4-{[(2-fluorophenyl)methyl]oxy}phenyl)-3,4-dihydro-2H-pyrrole-2-carboxylate (D72)

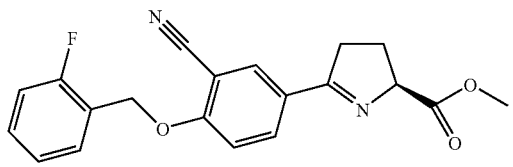

Methyl (2S)-5-(3-cyano-4-{[(2-fluorophenyl)methyl]oxy}phenyl)-3,4-dihydro-2H-pyrrole-2-carboxylate (D72, 70 mg) was prepared following the procedure described in description 67 using: methyl (2S)-2-amino-5-(3-cyano-4-{[(2-fluorophenyl)methyl]oxy}phenyl)-4-pentynoate (D71). UPLC: Rt=0.72 min, MS: (ES/+) m/z: 353 [MH$^+$], C20H17FN2O3 requires 352.

Description 73: Methyl (5R)-5-(3-cyano-4-{[(2-fluorophenyl)methyl]oxy}phenyl)-L-prolinate (D73)

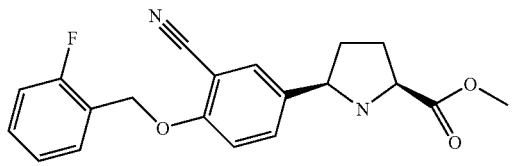

A suspension of methyl (2S)-5-(3-cyano-4-{[(2-fluorophenyl)methyl]oxy}phenyl)-3,4-dihydro-2H-pyrrole-2-carboxylate (D72, 70 mg, 0.198 mmol) and Pt (5% on carbon) in ethyl acetate (10 ml) was stirred at room temperature for 24 hrs. Filtration over celite and subsequent evaporation gave the title compound (64 mg, 91%). The obtained material was used unpurified in the next step. UPLC: Rt=0.55 min, MS: (ES/+) m/z: 355 [MH$^+$], C20H19FN2O3 requires 354.

Description D74: methyl (2S)-5-(4-bromophenyl)-2-({[(1,1-dimethylethyl)oxy]carbonyl}amino)-4-pentynoate (D74)

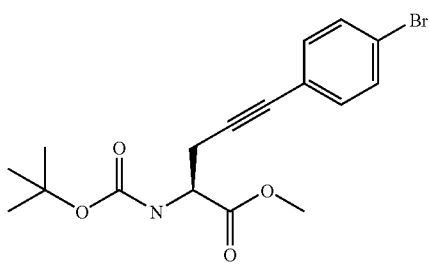

A solution of methyl (2S)-2-({[(1,1-dimethylethyl)oxy]carbonyl}amino)-4-pentynoate (D64, 1.020 g, 4.49 mmol), prepared by an analogous procedure to the one described hereinabove, 4-Iodo-bromobenzene (1.524 g, 5.38 mmol), diethylamine (2.28 ml, 1.62 g, 22.12 mmol), CuI (84 mg, 0.441 mmol) and Pd(PPh$_3$)$_2$Cl$_2$ (156 mg, 0.22 mmol) in diethyl ether (10 ml) was stirred at room temperature for 24 h.

Ethyl acetate was added and the organic layer was washed with aqueous ammonium chloride solution, dried (Na$_2$SO$_4$), filtered and evaporated under vacuum. The residue was purified via flash chromatography using a gradient of cyclohexanes and ethyl acetate (98:2 to 80:20) to afford the title compound (1.199 g, 69%). MS: (ES/+) m/z: 404, 406 [MH$^+$], C17H20BrNO4 requires 404. $^1$H-NMR (400 MHz, DMSO-d$_6$) δ (ppm): 7.56 (d, 1H), 7.45 (d, 1H), 7.32 (d, 1H), 4.30 (m, 1H), 3.67 (s, 3H), 2.82 (m, 2H), 1.40 and 1.38 (2xs, 9H).

Description D75: methyl (2S)-2-amino-5-(4-bromophenyl)-4-pentynoate (D75)

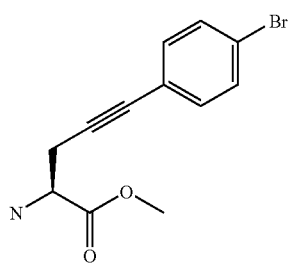

To a solution of methyl (2S)-5-(4-bromophenyl)-2-({[(1,1-dimethylethyl)oxy]carbonyl}amino)-4-pentynoate (D74, 1.199 g, 3.136 mmol) in dry EtOAc (18 ml) and dry methanol (2 ml) was added AcCl (1.14 ml, 1.25 g, 15.98 mmol). After solvent removal the residue was purified using a SCX cartridge affording the title compound (849 mg, 95%). UPLC: Rt 0.51 min, MS: (ES/+) m/z: 282, 284 [MH$^+$], C12H12BrNO2 requires 282.

Description D76: methyl (2S)-5-(4-bromophenyl)-3,4-dihydro-2H-pyrrole-2-carboxylate (D76)

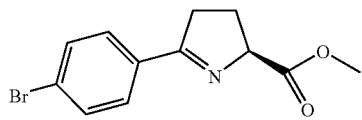

A solution of methyl (2S)-2-amino-5-(4-bromophenyl)-4-pentynoate (D75, 849 mg, 3.009 mmol) and silver-(I)-triflate in acetonitrile (30 ml) was stirred overnight at room temperature. Then brine was added and the product was extracted with dichloromethane. The combined organic layers were dried (Na$_2$SO$_4$), filtered and evaporated to afford the title compound (874 mg, 96%). UPLC: Rt 0.70 min; MS: (ES/+) m/z: 282, 284 [MH$^+$], C12H12BrNO2 requires 282.

Description D77: methyl (5R)-5-(4-bromophenyl)-L-prolinate (D77)

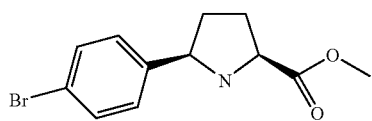

A solution of methyl (2S)-5-(4-bromophenyl)-3,4-dihydro-2H-pyrrole-2-carboxylate (D76, 799 mg, 2.83 mmol)

and Pt/C (50 mg) was stirred under hydrogen (1 atm) overnight. Then TFA (0.25 ml) was added and hydrogenation was continued for another 2 h. Then more Pt/C (100 mg) was added and the mixture was stirred for additional 9 h under hydrogen (1 atm). After that additional catalyst (100 mg) and TFA (0.25 ml) was added and stirring was continued for another 5 h under hydrogen atmosphere. Then additional catalyst was added (100 mg). After additional 4 h the reaction was finished and the solution was filtered over celite, evaporated and purified using a SCX cartridge to afford the title compound (641 mg, 79%). UPLC: Rt 0.47 min; MS: (ES/+) m/z: 284, 286 [MH+], C12H14BrNO2 requires 284.

Description D78: 1-(1,1-dimethylethyl) 2-methyl (2S,5R)-5-(4-bromophenyl)-1,2-pyrrolidinedicarboxylate (D78)

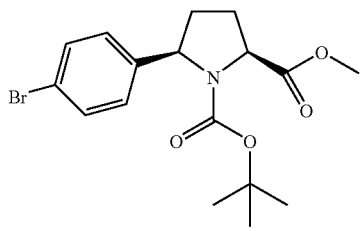

A solution of methyl (5R)-5-(4-bromophenyl)-L-prolinate (D77, 641 mg, 2.25 mmol) and di-tert-butyl dicarbonate (517 mg, 2.37 mmol) in dry DCM (10 ml) was stirred for 6.5 h at room temperature. The reaction was evaporated and purified via flash chromatography using a gradient of ethyl acetate/cyclohexanes (5:95 to 40:60) to afford the title compound (636 mg, 73%). UPLC: Rt 0.92 min; MS: (ES/+) m/z: 384, 386 [MH+], C17H22BrNO4 requires 384.

Description 79: 1-(1,1-dimethylethyl) 2-methyl (2S, 5R)-5-{4-[(E)-2-phenylethenyl]phenyl}-1,2-pyrrolidinedicarboxylate (D79)

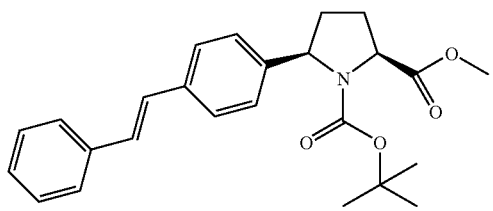

In a vial containing 1-(1,1-dimethylethyl) 2-methyl (2S, 5R)-5-(4-bromophenyl)-1,2-pyrrolidinedicarboxylate (D78, 100 mg, 0.26 mmol), sodium carbonate (138 mg, 1.30 mmol), 4,4,5,5-tetramethyl-2-[(E)-2-phenylethenyl]-1,3,2-dioxaborolane (90 mg, 0.39 mmol) and Pd(PPh3)4 (30 mg, 0.026 mmol) were added dioxane (2 ml) and water (1 ml). The mixture was stirred for 2 h at 80° C. After cooling, the mixture was extracted with ethyl acetate. The organic layer was filtered by phase separator tube and evaporated. The residue was purified by chromatography on silica gel using cyclohexane/ethyl acetate (1:0 to 9:1) to afford the title compound as a light yellow solid (90 mg, 85%). $R_t$ (HPLC): 7.02 min; MS: (ES/+) m/z: 308 (MH-Boc) C25H29NO4 requires 407.

Description 80: 1-(1,1-dimethylethyl) 2-methyl (2S, 5R)-5-[4-(2-phenylethyl)phenyl]-1,2-pyrrolidinedicarboxylate (D80)

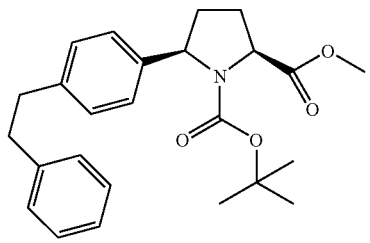

To a solution of 1-(1,1-dimethylethyl) 2-methyl (2S,5R)-5-{4-[(E)-2-phenylethenyl]phenyl}-1,2-pyrrolidinedicarboxylate (D79, 50 mg, 0.12 mmol) in methanol was added palladium (10 mg, 10 wt. % dry basis on activated carbon) and the mixture was stirred under hydrogen atmosphere (1 atm) for 4 h. A further addition of catalyst (20 mg) was required before the reaction was complete (as shown by HPLC). The catalyst was filtered off, the solvent removed under reduced pressure affording the title compound as a colourless oil (45 mg, 92%). $R_t$ (HPLC): 7.04 min; MS: (ES/+) m/z: 432 [M+Na] C25H31NO4 requires 409.

Description 81: (5R)-5-[4-(2-phenylethyl)phenyl]-L-prolinamide (D81)

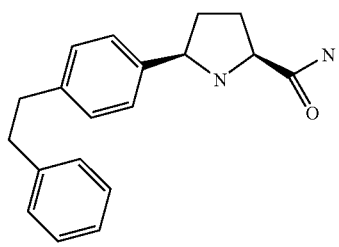

To a solution of 1-(1,1-dimethylethyl) 2-methyl (2S,5R)-5-[4-(2-phenylethyl)phenyl]-1,2-pyrrolidinedicarboxylate (D80, 43 mg, 0.1 mmol) in ethyl acetate (0.9 ml) and methanol (0.1 ml) at 0° C. was added AcCl (86 μl, 1.20 mmol) and the mixture was stirred for six hours from 0° C. to r.t. The solvent was removed under vacuum and the residue was filtered on scx cartridge and then dissolved in ammonia 7N solution in methanol. This solution was stirred for 18 h r.t. The solvent was evaporated to afford the title compound as a white solid (30 mg, quantitative). $R_t$ (HPLC): 3.84 min; MS: (ES/+) m/z: 295 [MH]+ C19H22N2O requires 294; ¹H NMR (400 MHz, CDCl₃) δ (ppm): 7.45-7.69 (br.s, 1H); 7.28-7.35 (m, 4H); 7.16-7.25 (m, 5H); 5.31-5.63 (br.s, 1H); 4.30-4.36 (m, 1H); 3.87-3.93 (m, 1H); 2.94 (s, 4H); 2.26-2.39 (m, 1H); 2.11-2.26 (m, 2H); 1.63-1.77 (m, 1H).

Description 82: 2-bromo-5-{[(2-fluorophenyl)methyl]oxy}pyridine (D82)

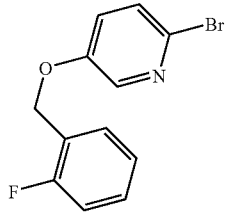

To a solution of 6-bromo-3-pyridinol (commercial source, 0.870 g, 5.0 mmol) in acetone (20 ml) were added potassium carbonate (1.04 g, 7.5 mmol) and 1-(bromomethyl)-2-fluorobenzene (Aldrich, 1.2 ml, 10.0 mmol) and the mixture was stirred for three hours at r.t. The solvent was evaporated and the residue was diluted with water and extracted with ethyl acetate. The organic layer was dried (Na$_2$SO$_4$), filtered and evaporated. The residue was purified by chromatography on silica gel using cyclohexane/ethyl acetate (1:0 to 98:2) to afford the title compound as a white solid (1.28 g, 90%). MS: (ES/+) m/z: 282, 284 [MH]+ C$_{12}$H$_9$BrFNO requires 281, 283; $^1$H NMR (400 MHz, CDCl$_3$) δ (ppm): 8.12-8.20 (m, 1H); 7.43-7.53 (m, 1H); 7.32-7.43 (m, 2H); 7.16-7.24 (m, 2H); 7.07-7.16 (m, 1H); 5.17 (s, 2H).

Description 83: methyl (2S)-2-({[(1,1-dimethylethyl)oxy]carbonyl}amino)-5-(5-{[(2-fluorophenyl)methyl]oxy}-2-pyridinyl)-4-Pentynoate (D83

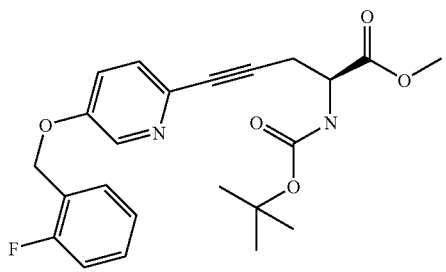

To a solution of 2-bromo-5-{[(2-fluorophenyl)methyl]oxy}pyridine (D82, 0.60 g, 2.13 mmol), methyl (2S)-2-({[(1,1-dimethylethyl)oxy]carbonyl}amino)-4-pentynoate (D64, 1.20 g, 5.30 mmol), synthesized with an analogous procedure to the one described hereinabove, and diethylamine (1.10 ml, 10.65 mmol) in diethyl ether (20 ml) were added copper iodide (0.042 g, 0.22 mmol) and PdCl$_2$(PPh$_3$)$_2$ (0.077 g, 0.11 mmol) and the mixture was stirred for three hours at room temperature. The reaction was quenched with a saturated solution of ammonium chloride diluted with water and extracted with diethyl ether. The organic layer was dried (Na$_2$SO$_4$) filtered and evaporated. The residue was purified by chromatography on silica gel using cyclohexane/ethyl acetate (9:1 to 8:2) to afford the title compound as a yellow solid (0.36 g, 40%). Rt (HPLC): 5.64 min; MS: (ES/+) m/z: 429 [MH]+ C23H25FN2O5 requires 428; $^1$H NMR (400 MHz, CDCl3) δ (ppm): 8.28-8.39 (m, 1H); 7.44-7.53 (m, 1H); 7.32-7.41 (m, 2H); 7.16-7.25 (m, 2H); 7.08-7.16 (m, 1H); 5.37-5.55 (m, 1H); 5.19 (s, 2H); 4.46-4.66 (m, 1H); 3.81 (s, 3H); 2.91-3.07 (m, 2H); 1.47 (s, 9H).

Description 84: Methyl (2S)-2-amino-5-(5-{[(2-fluorophenyl)methyl]oxy}-2-pyridinyl)-4-pentynoate (D84)

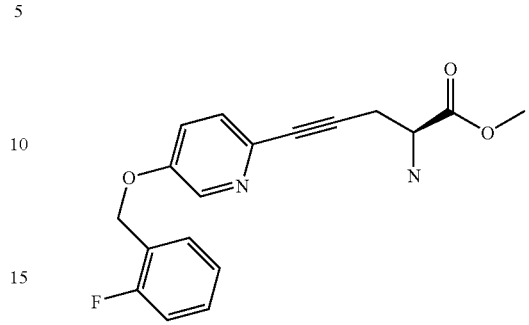

To a solution of methyl (2S)-2-({[(1,1-dimethylethyl)oxy]carbonyl}amino)-5-(5-{[(2-fluorophenyl)methyl]oxy}-2-pyridinyl)-4-pentynoate (D83, 0.439, 1.0 mmol), prepared by an analogous procedure to that described hereinabove, in ethyl acetate (4.5 ml) and methanol (0.5 ml) at 0° C. was added dropwise AcCl (0.5 ml, 7.0 mmol) and the mixture was stirred from 0° C. to r.t. for four hours. The solvent was removed under vacuum. The residue was diluted with a saturated solution of sodium bicarbonate and extracted with dichloromethane. The organic layer was dried, filtered and evaporated affording the title compound as yellow oil (0.30 g, 91%). Rt (HPLC): 3.60 min; MS: (ES/+) m/z: 329 [MH]+ C18H17FN2O3 requires 328; $^1$H NMR (400 MHz, CDCl3) δ (ppm): 8.30-8.36 (m1H); 7.45-7.51 (m, 1H); 7.31-7.40 (m, 2H); 7.16-7.24 (m, 2H); 7.07-7.16 (m, 1H); 5.19 (s, 2H); 3.75-3.81 (m, 1H); 3.79 (s, 3H); 2.80-2.99 (m, 2H).

Description 85: Methyl (2S)-5-(5-{[(2-fluorophenyl)methyl]oxy}-2-pyridinyl)-3,4-dihydro-2H-pyrrole-2-carboxylate (D85)

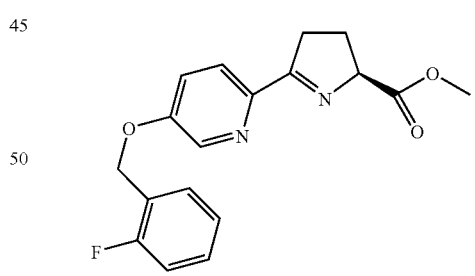

To a solution of methyl (2S)-2-amino-5-(5-{[(2-fluorophenyl)methyl]oxy}-2-pyridinyl)-4-pentynoate (D84, 300 mg, 0.91 mmol) in acetonitrile was added silver triflate (24 mg, 0.091 mmol) and the mixture was stirred for 60 hours at room temperature. The solvent was evaporated and the residue diluted with water and extracted with ethyl acetate. The organic layer was dried (Na$_2$SO$_4$), filtered and evaporated affording the title compound as a yellow solid (300 mg, quantitative). Rt (HPLC): 3.58 min; MS: (ES/+) m/z: 329 [MH]+ C18H17FN2O3 requires 328.

Description 86: Methyl (5R)-5-(5-{[(2-fluorophenyl)methyl]oxy}-2-pyridinyl)-L-prolinate (D86)

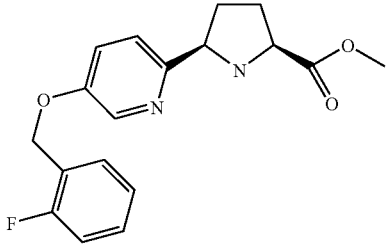

To a solution of methyl (2S)-5-(5-{[(2-fluorophenyl)methyl]oxy}-2-pyridinyl)-3,4-dihydro-2H-pyrrole-2-carboxylate (D85, 300 mg, 0.91 mmol) in ethyl acetate was added platinum on activated carbon (70 mg, 5 wt. % dry basis Degussa type F101 RAW) and the mixture was stirred under hydrogen atmosphere (P=1 atm) for 4 hours. After a further addiction of acetic acid (0.4 ml) and stirring for 12 hours the reaction wasn't complete. A further addiction of catalyst (70 mg) and trifluoroacetic acid was required before the reaction was complete. The catalyst was filtered off, the solvent removed under reduced pressure and the residue filtered on scx cartridge. The residue was purified by chromatography on silica gel using cyclohexane/ethyl acetate (7:3 to 6:4) to afford the title compound as a colourless oil (180 mg, 60%). $R_t$ (HPLC): 3.69 min; MS: (ES/+) m/z: 331 [MH]+ $C_{18}H_{19}FN_2O_3$ requires 330; $^1$H NMR (400 MHz, CDCl$_3$) δ (ppm): 8.27-8.43 (m, 1H); 7.45-7.56 (m, 1H); 7.38-7.44 (m, 1H); 7.31-7.38 (m, 1H); 7.24-7.31 (m, 1H); 7.15-7.23 (m, 1H); 7.08-7.15 (m, 1H); 5.18 (s, 2H); 4.32-4.41 (m, 1H); 3.98-4.05 (m, 1H); 3.79 (s, 3H); 2.19-2.31 (m, 2H); 2.04-2.13 (m, 1H); 1.77-1.90 (m, 1H).

Description 87: N-(phenylmethyl)-2-propen-1-amine (D87)

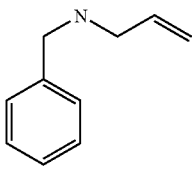

To a solution of benzylamine (5.7 ml, 52.2 mmol) and sodium iodide (38 mg, 0.25 mmol) in DMSO (30 ml) was added dropwise allyl bromide (2.2 ml, 25.4 mmol) at 0° C. under argon. After stirring for 3 h at room temperature the reaction was complete as shown by TLC (cyclohexanes:ethyl acetate 1:1). Then saturated aqueous sodium bicarbonate solution was added, the product was extracted with diethyl ether (100 ml) and the organic layer was washed with brine. The crude product was purified via flash chromatography to give the title compound (2.1 g, 57%) as a clear oil. $^1$H NMR (400 MHz, CDCl3) δ (ppm): 7.4-7.2 (m, 5H), 6.0-5.9 (m, 1H), 5.3-5.1 (m, 2H), 3.8 (s, 2H), 3.3 (d, 2H), 1.5 (bs, 1H).

Description 88: N-{[(1,1-dimethylethyl)oxy]carbonyl}-N-(phenylmethyl)glycine (D88)

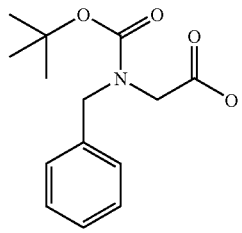

A solution of N-(phenylmethyl)glycine (990 mg, 6.0 mmol), triethylamine (1.58 ml, 12 mmol) and Boc$_2$O (1.44 g, 6.6 mmol) in water/THF (1:1, 30 ml) was stirred at room temperature for 1 h. THF was evaporated and 5% HCl was added until the pH=4. The product was extracted with ethyl acetate and evaporated. The residue was purified via flash chromatography to give the title compound (1.47 g, 92%).

Description 89: 1,1-dimethylethyl {2-oxo-2-[(phenylmethyl)(2-propen-1-yl)amino]ethyl}(phenylmethyl)carbamate (D89)

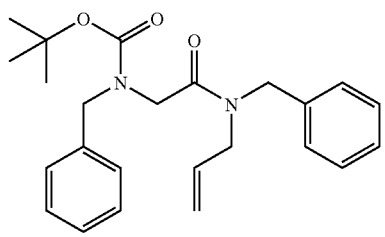

A solution of N-{[(1,1-dimethylethyl)oxy]carbonyl}-N-(phenylmethyl)glycine (D88, 1.06 g, 4.0 mmol), DIPEA (1.38 ml, 8.0 mmol) and TBTU (1.61 g, 5.0 mmol) in dry DMF (8 ml) was stirred at room temperature for 30 min. Then N-(phenylmethyl)-2-propen-1-amine (D87, 647 mg, 4.4 mmol) was added and stirring was continued for another 2 h. After reaction was completed, ethyl acetate was added and the organic layer was washed with water and brine. The residue was purified via flash chromatography to give the title compound (1.50 g, 95%). $^1$H NMR (400 MHz, CDCl3) δ (ppm): 7.4-7.2 (m, 10H), 5.8-5.5 (m, 1H), 5.2-5.0 (m, 2H), 4.7-4.3 (m, 4H), 4.1-3.7 (m, 4H), 1.5 (s, 9H); MS: (ES/+) m/z: 295 [M-BOC$^+$], $C_{24}H_{30}N_2O_3$ requires 394.

Description 90: $N^1,N^2$-bis(phenylmethyl)-$N^1$-2-propen-1-ylglycinamide (D90)

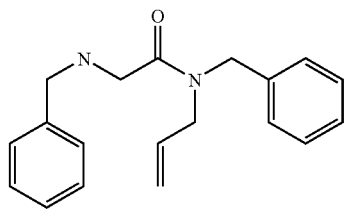

TFA (3 ml) was added dropwise to a solution of 1,1-dimethylethyl {2-oxo-2-[(phenylmethyl)(2-propen-1-yl)amino]ethyl}(phenylmethyl)carbamate (D89, 1.18 g, 3 mmol) in dry dichloromethane (12 ml) at 0° C. After stirring at room temperature for 3 h the solvent was evaporated and the residue purified via SCX cartridge to give the title compound (880 mg, quant.) as a clear oil. ¹H NMR (400 MHz, CDCl3) δ (ppm): 7.4-7.2 (m, 10H), 5.9-5.6 (m, 1H), 5.2-5.0 (m, 2H), 4.6, 4.4 (s, 2H), 4.1-3.7 (m, 4H), 3.5 (s, 2H), 2.4 (bs, 1H).

Description 91: 1-(Bromomethyl)-2-fluorobenzene (D91)

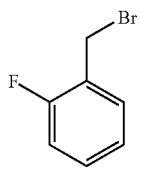

To a solution of (2-fluorophenyl)methanol (Aldrich, 10.0 g, 79.3 mmol) and triphenylphosphine (29.1 g, 111 mmol) in DCM was added CBr₄ (31.6 g, 95.2 mmol) in small portions at 0° C. The mixture was stirred for 2 h at room temperature. The solvent was evaporated and the residue purified via flash chromatography (cyclohexanes:ethyl acetate 95:5) to give the title compound (14 g, 93%). ¹H NMR (400 MHz, CDCl3) δ (ppm): 7.42 (t, 1H), 7.36-7.28 (m, 1H), 7.17-7.07 (m, 2H), 4.55 (s, 2H).

Description 92: 4-{[(2-Fluorophenyl)methyl]oxy}benzaldehyde (D92)

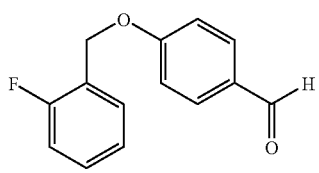

A suspension of 1-(bromomethyl)-2-fluorobenzene (D91, 11.5 g, 60.8 mmol), 4-hydroxybenzaldehyde (5.3 g, 43.3 mmol) and K₂CO₃ (12.0 g, 86.8 mmol) in acetone was divided in three equal parts and heated in a microwave apparatus at 80° C. for 40 min. The mixtures were diluted with water and extracted with ethyl acetate. The organic layer was dried (Na₂SO₄) and evaporated. The residue was purified via flash chromatography (cyclohexanes:ethyl acetate 95:5) to give the title compound (7.9 g, 79%). Rf (cyclohexanes:ethyl acetate 8:2): 0.38.

Description 93: rac-(2R,3aR,6aR)-2-(4-{[(2-Fluorophenyl)methyl]oxy}phenyl)-1,5-bis(phenylmethyl)hexahydropyrrolo[3,4-b]pyrrol-6(1H)-one (D93)

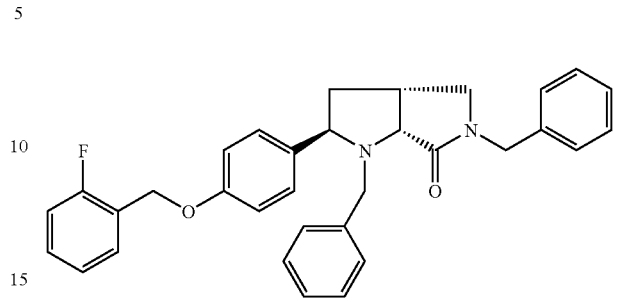

A solution of 4-{[(2-fluorophenyl)methyl]oxy}benzaldehyde (D92, 920 mg, 4.0 mmol), prepared by an analogous procedure to that described hereinabove, N¹,N²-bis(phenylmethyl)-N1-2-propen-1-ylglycinamide (D90, 588 mg, 2.0 mmol) and DIPEA (0.68 ml, 4.0 mmol) in dry toluene (8 ml) were stirred at 120° C. for 72 h. After the reaction was terminated, it was cooled to room temperature, diluted with ethyl acetate and washed with water and brine. The residue was purified via flash chromatography affording the title compound (503 mg, 50%) as a racemate. Rf (cyclohexanes:ethyl acetate 1:1): 0.57.

Description 94: rac-(2R,3aR,6aR)-2-(4-{([(2-Fluorophenyl)methyl]oxy}phenyl)-1-(phenylmethyl)hexahydropyrrolo[3,4-b]pyrrol-6(1H)-one (D94)

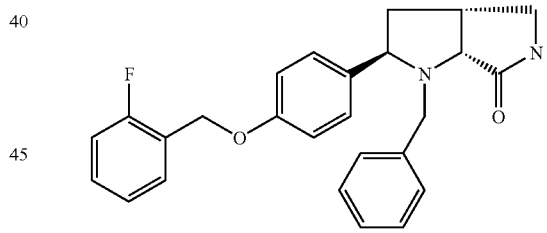

rac-(2R,3aR,6aR)-2-(4-{[(2-fluorophenyl)methyl]oxy}phenyl)-1,5-bis(phenylmethyl)-hexahydropyrrolo[3,4-b]pyrrol-6(1H)-one (D93, 503 mg, 1.0 mmol) was dissolved in DMSO (647 mg, 10.0 mmol) and the solution was stirred at room temperature. Then tBuOK (7.0 ml, solution 1M in THF) was added. Oxygen was then bubbled through the solution, via a gas dispersion tube for 30 min. Saturated ammonium chloride was added. The crude product was purified via flash chromatography to afford the title compound (60 mg, 20%). ¹H NMR (400 MHz, CHCl3-d) δ ppm 7.48 (t, 1H), 7.41 (d, 2H), 7.30 (d, 2H), 7.24 (t, 3H), 7.16 (dd, 1H), 7.13 (t, 1H), 7.05 (t, 1H), 6.95 (d, 2H), 5.48-5.59 (m, 1H), 5.09 (s, 2H), 4.21 (d, 1H), 3.76-3.85 (m, 1H), 3.71 (d, 1H), 3.45-3.54 (m, 2H), 3.09 (d, 1H), 2.88-2.97 (m, 1H), 2.08-2.21 (m, 1H), 1.96-2.07 (m, 1H).

Description 95, Description 96: 1,1-dimethylethyl (2S,5R)-2-[(dimethylamino)carbonyl]-5-(4-{[(2-fluorophenyl)methyl]oxy}phenyl)-1-pyrrolidinecarboxylate (D95) and 1,1-dimethylethyl (2R,5S)-2-(4-{[(2-fluorophenyl)methyl]oxy}phenyl)-5-[(methylamino)carbonyl]-1-pyrrolidinecarboxylate (D96)

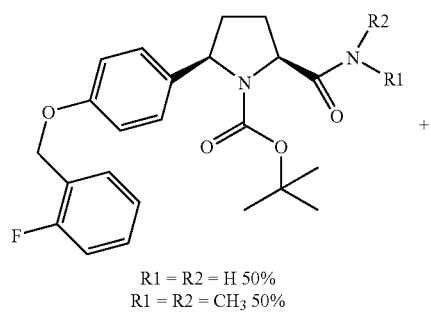

R1 = R2 = H 50%
R1 = R2 = CH₃ 50%

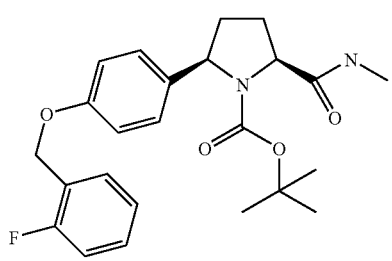

To a solution of 1,1-dimethylethyl (2S,5R)-2-(aminocarbonyl)-5-(4-{[(2-fluorophenyl)methyl]oxy}phenyl)-1-pyrrolidinecarboxylate (D14, 80 mg, 0.19 mmol), prepared using an analogous procedure to the one described hereinabove, in N,N-dimethylformamide at 0° C. was added sodium hydride (8.0 mg, 0.22 mmol, 60% dispersion in mineral oil) and the mixture was stirred for 10 min at the same temperature. Methyl iodide (18 μl, 0.29 mmol) was added and the mixture was stirred for one hour at room temperature. The reaction was quenched with water and extracted with ethyl acetate. The organic layer was washed with ice cold brine, dried (Na₂SO₄) and evaporated. The residue was purified by chromatography on silica gel. D96 (40 mg, 49%). $R_t$ (HPLC): 5.73 min; MS: (ES/+) m/z: 451 [M+Na] $C_{24}H_{29}FN_2O_4$ requires 428; ¹H NMR (400 MHz, DMSO-d₆) δ (ppm): 7.78-8.02 (br.s, 1H); 7.47-7.68 (m, 3H); 7.34-7.47 (m, 1H); 7.17-7.33 (m, 2H); 6.87-6.89 (m, 2H); 5.12 (s, 2H); 4.70-4.90 and 4.50-4.70 (m,m, 1H); 4.01-4.28 (m, 1H); 2.64 and 2.65 (s,s, 3H); 2.11-2.30 (m, 1H); 1.92-2.11 (m, 1H); 1.65-1.92 (m, 2H); 1.31 and 1.06 (s,s, 9H).

D95 (20 mg) as a mixture (1:1) of the dimethyl compound [(R₁=R₂=CH₃) $R_t$ (HPLC): 5.96 min; MS: (ES/+) m/z: 343 [MH-Boc] $C_{25}H_{31}FN_2O_4$ requires 442] and the starting material (R¹=R₂=H) [Rt (HPLC): 5.54 min; MS: (ES/+) m/z: 315 [MH-Boc] $C_{23}H_{27}FN_2O_4$ requires 414].

EXAMPLES

Example 1

Example 2

(2,6)-6-(4-{[(3-Fluorophenyl)methyl]oxy}phenyl)-2-piperidinecarboxamide (enantiomer 1, E1), (2,6)-6-(4-{[(3-Fluorophenyl)methyl]oxy}phenyl)-2-piperidinecarboxamide (enantiomer 2, E2)

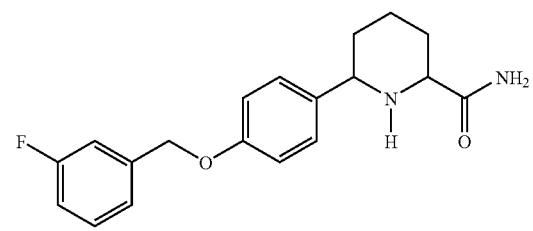

A solution of 6-(4-{[(3-fluorophenyl)methyl]oxy}phenyl)-2-pyridinecarboxamide (D4, 80 mg, 0.26 mmol) and PtO₂ (27 mg, 0.12 mmol) in acetic acid (20 ml) was stirred under a hydrogen atmosphere (4 atmos) for 16 h. The acetic acid was evaporated and the residue was taken up in DCM and washed with NaHCO₃ solution. The resulting crude material was purified by chromatography on silica gel to afford the title compound (40 mg, 46%) as a mixture of enantiomers and starting material (D4, 16 mg); MS: (ES/+) m/z: 329 [MH⁺], C19H21FN2O2 requires 328; ¹H NMR (500 MHz, DMSO-d6) δ (ppm): 7.39-7.46 (m, 1H), 7.31 (d, 2H), 7.26 (t, 2H), 7.14 (t, 1H), 7.05-7.11 (m, 1H), 6.88-6.98 (m, 3H), 5.02-5.17 (m, 2H), 3.53 (d, 1H), 3.11 (d, 1H), 2.28-2.38 (m, 1H), 1.82 (d, 2H), 1.64 (d, 1H), 1.39-1.53 (m, 1H), 1.16-1.30 (m, 2H).

The enantiomers were separated via chiral preparative HPLC using a chiralcel OD 10 um column (250×4.6 mm, mobile phase: A: n-hexane; B: ethanol, gradient: isocratic 30% B, flow rate: 0.8 ml/min, UV wavelength range: 200-400 nm). E1: $R_t$=11.99 min, 49.9% a/a; E2: $R^t$=14.95 min, 50.1% a/a).

Example 3

(5R)-5-{4-[(Phenylmethyl)oxy]phenyl}-L-prolinamide hydrochloride (E3)

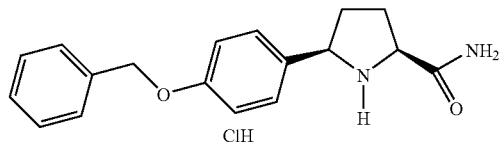

To a solution of 1,1-dimethylethyl (2S,5R)-2-(aminocarbonyl)-5-(4-[(phenylmethyl)oxy]phenyl)-1-pyrrolidinecarboxylate (D12, 45 mg, 0.113 mmol) in a mixture of ethyl acetate and methanol (9/1, 1 ml) was added acetyl chloride (20 μl, 0.282 mmol) at 0° C. The mixture was shaken for 1.5 h and slowly allowed to warm to room temperature. After 4 h under these conditions, additional acetyl chloride (20 μl, 0.654 mmol) was added. After evaporating the solvent, the residue was triturated with diethyl ether to afford the title compound as a white solid (25 mg, 66%); Rt (HPLC): 3.55 min; ¹H NMR (300 MHz, DMSO-d6) δ (ppm): 10.50 (bs, 1H); 8.15 (bs, 1H); 8.05 (s, 1H); 7.73 (s, 1H); 7.42-7.49 (m, 4H); 7.40 (t, 2H); 7.30-7.36 (m, 1H); 7.08 (d, 2H); 5.15 (s, 2H); 4.60 (dd, 1H); 4.30 (dd, 1H); 2.23-2.40 (m, 2H); 2.10-2.20 (m, 1H); 1.95-2.08 (m, 1H).

Example 4

(5R)-5-(4-{[(2-Fluorophenyl)methyl]oxy}phenyl)-L-prolinamide (E4)

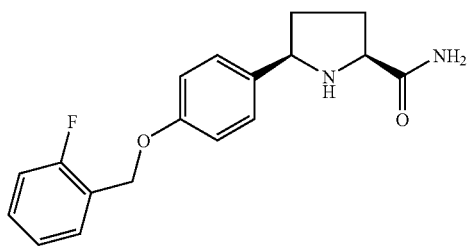

Procedure 1: A solution of methyl (5R)-5-(4-{[(2-fluorophenyl)methyl]oxy}phenyl)-L-prolinate (D58, 32.5 g, 98.6 mmol) in methanol (65 ml) was cooled to 0-10° C. A solution of ammonia in methanol (ca 11.2M) was added in four portions over 11 hours (175.4 ml, 43.8 ml, 43.8 ml. 43.8 ml) then the reaction stirred at 15-20° C. for 22 hours. Ammonia and methanol were removed under vacuum, then toluene (65 ml) was added and the mixture heated to 60-65° C. to give a solution, which was then concentrated under vacuum and the residue dried at 60° C. Toluene (130 ml) and methanol (0.32 ml) were added to the residue and the mixture heated to 70-75° C. The resulting solution was then cooled to 15-20° C. and stirred for 1 hour. The solid was filtered, washed with toluene and dried at 45-50° C. to give the title compound (21.8 g) as a solid.

¹H NMR (500 MHz, DMSO-d6) δ (ppm): 1.39 (m, 1H); 1.84 (m, 1H); 2.04 (m, 2H); 3.54 (m, 1H); 4.09 (m, 1H); 5.12 (s, 2H); 6.96 (d, 2H); 7.15 (m, 1H); 7.25 (m, 2H); 7.34 (d, 2H); 7.41 (m, 2H); 7.55 (t, 1H).

E4 was also prepared as follows:
Procedure 2: Methyl (5R)-5-{4-[(2-fluorobenzyl)oxy]phenyl}-L-prolinate (D58) (127 g) was dissolved in 7N NH₃ solution in MeOH (1016 mL) and the mixture was stirred at room temperature for 24 hrs. Further 7N NH₃ solution in MeOH (63 mL) was added and the mixture stirred for a further 15 hours. The solvent was removed under reduced pressure and MeOH (635 mL) was added. The solution was evaporated to dryness and the white solid obtained was left under high vacuum over the weekend. The white solid was suspended in a mixture of MTBE/Toluene 1:1 (254 mL) at 20° C. and stirred for 1 hr. The suspension was filtered and the solid washed with MTBE (254 mL). The white solid was dried at 40° C. overnight under vacuum affording 122.4 g of material. This material was resuspended in a mixture of MTBE/toluene 1:1 (245 mL) and stirred at room temperature for 1 hour. The mixture was filtered and the solid was washed with MTBE (245 mL). The white solid obtained was dried at 40° C. overnight under vacuum to give the title compound (1099). ¹H NMR (600 MHz, DMSO-d6) δ (ppm): 7.54 (td, 1H); 7.41 (m, 1H); 7.38 (m, 2H); 7.34 (d, 2H); 7.24 (m, 2H); 7.13 (bs, 1H); 6.96 (d, 2H); 5.12 (s, 2H); 4.09 (dd, 1H); 3.55 (dd, 1H); 3.24 (bs, 1H); 2.07 (m, 1H); 2.00 (m, 1H); 1.85 (m, 1H); 1.40 (m, 1H).

Example 5

(5R)-5-(4-{[(2-Fluorophenyl)methyl]oxy}phenyl)-L-prolinamide hydrochloride (E5)

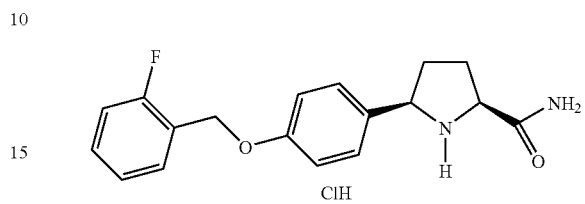

Procedure 1: To a solution of 1,1-dimethylethyl (2S,5R)-2-(aminocarbonyl)-5-(4-{[(2-fluorophenyl)methyl]oxy}phenyl)-1-pyrrolidinecarboxylate (D14, 51 mg, 0.123 mmol) in a mixture of ethyl acetate (0.9 ml) and methanol (1 ml) was added acetylchloride (28 μl, 2.5 eq) at 0° C. The mixture was shaken for 1.5 h and slowly allowed to warm to room temperature. After evaporating the solvent, the residue was triturated with diethyl ether to afford the title compound as a white solid (42 mg, quant.); Chiral HPLC: Column: chiralcel OD 10 um, 250×4.6 mm; Mobile phase: A: n-Hexane; B: Ethanol; Gradient: isocratic 30% B; Flow rate: 0.8 ml/min; UV wavelength range: 200-400 nm; Analysis time: 22 min; ret. time: 12.0 min. [α]$_D$=−30.5°. MS: (ES/+) m/z: 315 [MH⁺], C18H19FN2O2 requires 314; ¹H NMR (400 MHz, DMSO-d6) δ ppm 10.19 (br. s., 1H), 8.13 (br. s., 1H), 7.94 (s, 1H), 7.60-7.77 (m, 1H), 7.51 (dt, 1H), 7.43 (d, 2H), 7.34-7.41 (m, 1H), 7.23 (d, 1H), 7.18 (dd, 1H), 7.05 (d, 2H), 5.13 (s, 2H), 4.49-4.60 (m, 1H), 4.19-4.28 (m, 1H), 2.17-2.38 (m, 2H), 2.05-2.16 (m, 1H), 1.92-2.03 (m, 1H).

Example 5 was also prepared as follows:
Procedure 2: ((5R)-5-(4-{[(2-fluorophenyl)methyl]oxy}phenyl)-L-prolinamide) (E4, 109 g) was dissolved in DCM (654 mL) and Et₂O (654 mL) was added at room temperature. HCl 1N in Et₂O (380.4 mL) was added dropwise at room temperature. The suspension was cooled to 0° C. and stirred at this temperature for 1 hr. The solid was filtered, washed with Et₂O (2×327 mL) and dried at 40° C. under vacuum overnight to afford Form 1 crystals of the title compound (121.24 g). ¹H NMR (600 MHz, DMSO-d6) δ (ppm): 10.72 (bs, 1H); 8.10 (bs, 1H); 8.08 (s, 1H); 7.72 (s, 1H); 7.56 (td, 1H); 7.49 (d, 2H); 7.43 (qd, 1H); 7.25 (m, 2H); 7.10 (d, 2H); 5.17 (s, 2H); 4.61 (dd, 1H); 4.30 (dd, 1H); 2.32 (m, 2H); 2.16 (m, 1H); 2.02 (m, 1H).

Procedure 3: ((5R)-5-(4-{[(2-fluorophenyl)methyl]oxy}phenyl)-L-prolinamide) (E4, 10 g, 31.8 mmol) was dissolved in DCM (50 ml) and stirred with charcoal (1 g), then filtered, washing with DCM (30 ml). The residue was concentrated under vacuum, removing about 20 ml of DCM. Ether (60 ml) was added, followed by a solution of HCl in ether (0.84N, 40 ml), and the mixture was then stirred at 20-25° C. for 30 min, then cooled to 0-5° C. and stirred for 2 hours. The solid was filtered, washed with ether, then dried at room temperature to give Form 1 crystals of title compound (10.25 g). ¹H NMR (300 MHz, DMSO-d₆) δ (ppm): 2.04 (m, 1H); 2.18 (m, 1H); 2.32 (m, 2H); 4.34 (m, 1H); 4.64 (m, 1H); 5.18 (s, 2H); 7.10 (d, 2H); 7.25 (m, 2H); 7.40-7.60 (m, 4H); 7.77 (s, 1H); 8.24 (s, 1H); 11.03 (b, 1H).

Procedure 4: In a round bottom flask, a solution of ((5R)-5-(4-{[(2-fluorophenyl)methyl]oxy}phenyl)-L-prolinamide)

(E4, 1.4 g, 4.45 mmol) in ethylacetate (14 ml) and MeOH (2.5 ml) at 0° C. was treated with HCl 1M in diethylether (1.1 eq, 4.89 ml). The precipitation occurred quite soon and the mixture was stirred at 0° C. for 1 h. The mixture was then diluted with dry diethylether (10 ml) and then filtered on a Gooch filter (porosity 4, diameter 5 cm). The cake was washed on the filter with dry diethylether (2×20 ml) and the white solid thus obtained was transferred into a round bottom flask, dried under high vacuum at 40° C. for 2 h and then at room temperature for 18 hours. A white solid was obtained (1.51 g) of Form 1 crystals of the title compound.

Procedure 5: ((5R)-5-(4-{[(2-fluorophenyl)methyl]oxy}phenyl)-L-prolinamide) (E4, 25 g, 79.5 mmol) was dissolved in ethyl acetate (750 ml) and stirred with charcoal-(2.5 g), then filtered, washing with ethyl acetate (125 ml). To the filtrate and washings, a solution of HCl in ether (1N, 103 ml), was added over 30 minutes at 20-25° C. and the mixture was then stirred at 20-25° C. for 30 min, then cooled to 0-5° C. and stirred for 2 hours. The solid was filtered, washed with ethyl acetate (2×70 ml), then dried at room temperature to give Form 1 crystals of the title compound. (25.5 g).

Unique and discriminating peaks of Form 1 of the title compound of Example 5 have been identified and are illustrated in the table below:

| Position [° 2Th.] | d-spacing [Å] |
| --- | --- |
| 4.7 | 18.6 |
| 9.5 | 9.3 |
| 12.6 | 7.0 |
| 14.3 | 6.2 |
| 19.2 | 4.6 |
| 20.3 | 4.4 |
| 20.9 | 4.2 |
| 24.0 | 3.7 |
| 26.4 | 3.4 |

Melting point: 230° C.

The hydrochloride salt of the following compounds of formula (If) were prepared by a similar procedure to that used for Example 5, Procedure 1. For each compound, reference to a starting material is provided. This is provided merely for assistance to the skilled chemist. The starting material may not necessarily have been prepared from the batch referred to.

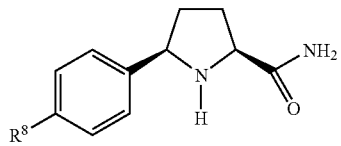

(If)

| No. | SM | $R^6$ | Characterization |
| --- | --- | --- | --- |
| E6 | D15 | 3-fluorobenzoxy | MS: (ES/+) m/z: 315 [MH⁺]. C18H19FN2O2 requires 314; 1H NMR (400 MHz, DMSO-d6) δ ppm 10.00 (br. s., 1H), 8.23 (br. s., 1H), 7.95 (s, 1H), 7.68 (s, 1H), 7.42 (d, 2H), 7.36-7.41 (m, 1H), 7.20-7.27 (m, 2H), 7.11 (dt, 1H), 7.03 (d, 2H), 5.13 (s, 2H), 4.47-4.60 (m, 1H), 4.15-4.30 (m, 1H), 2.18-2.36 (m, 2H), 2.04-2.17 (m, 1H), 1.88-2.04 (m, 1H). |
| E7 | D16 | 3-cyanobenzoxy | $R_t$ (HPLC) 3.40 min; MS: (ES/+) 322 m/z: [MH⁺]. C19H19N3O2 requires 321; ¹H-NMR (400 MHz, DMSO-$d_6$) δ (ppm): 1.99-2.07(m, 1H); 2.10-2.21 (m, 1H); 2.23-2.40 (m, 2H); 4.26-4.33 (m, 1H); 4.54-4.65 (m, 1H); 5.22 (s, 2H); 7.10 (d, 2H); 7.48 (d, 2H); 7.62 (t, 1H); 7.74 (s, 1H) 7.79 (s, 1H); 7.82 (d, 1H); 7.93 (s, 1H); 8.12 (br. s., 1H); 8.05 (s, 1H); 10.48 (br. s., 1H). |
| E8 | D17 | 4-fluorobenzoxy | $R_t$ (HPLC) 3.65 min; MS: (ES/+) 315 m/z: [MH⁺]. C18H19FN2O2 requires 314. |
| E9 | D18 | 2-cyanobenzoxy | $R_t$ (HPLC) 3.37 min; MS: (ES/+) 322 m/z: [MH⁺]. C19H19N3O2 requires 321; ¹H NMR (500 MHz, DMSO-d6) δ (ppm): 10.47 (br. s., 1H), 8.18 (br. s., 1H), 8.03 (s, 1H), 7.91 (d, 1H), 7.69-7.80 (m, 3H), 7.58 (dt, 1H), 7.49 (d, 2H), 7.11 (d, 2H), 5.28 (s, 2H), 4.61 (dd, 1H), 4.28 (dd, 1H), 2.22-2.41 (m, 2H), 2.10- 2.19 (m, 1H), 1.95-2.09 (m, 1H). |

-continued

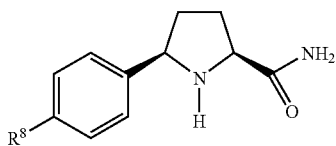

(If)

| No. | SM | R⁶ | Characterization |
|---|---|---|---|
| E10 | D19 | 4-cyanobenzoxy | R_t (HPLC) 3.39 min; MS: (ES/+) 322 m/z: [MH⁺]. C19H19N3O2 requires 321. |
| E11 | D20 | 2-(trifluoromethoxy)benzoxy | R_t (HPLC) 4.14 min; MS: (ES/+) 381 m/z: [MH⁺]. C19H19FN2O3 requires 380. ¹H NMR (500 MHz, DMSO-d₆) δ (ppm): 10.44 (br. s., 1H), 8.21 (br. s., 1H), 8.02 (s, 1H), 7.72 (s, 1H), 7.65 (dd, 1H), 7.50-7.55 (m, 1H), 7.48 (d, 2H), 7.43 (t, 2H), 7.08 (d, 2H), 5.16 (s, 2H), 4.59 (dd, 1H), 4.29 (dd, 1H), 2.23-2.39 (m, 2H), 2.11-2.19 (m, 1H), 1.96-2.08 (m, 1H). |
| E12 | D21 | (1R)-1-phenylethyloxy | R_t (HPLC) 3.75 min; MS: (ES/+) m/z: 311 [MH⁺]. C19H22N2O2 requires 310; ¹H NMR (500 MHz, DMSO-d₆) δ ppm 10.27 (br. s., 1H), 8.17 (br. s., 1H), 7.98 (s, 1H), 7.69 (s, 1H), 7.40 (d, 2H), 7.29-7.36 (m, 4H), 7.24 (t, 1H), 6.95 (d, 2H), 5.54 (q, 1H), 4.47- 4.56 (m, 1H), 4.21-4.29 (m, 1H), 2.17-2.39 (m, 2H), 2.06-2.16 (m, 1H), 1.91-2.06 (m, 1H), 1.54 (d, 3H). |
| E13 | D22 | 4-fluorophenoxy | R_t (HPLC) 3.47 min; MS: (ES/+) m/z: 301 [MH⁺]. C17H17FN2O2 requires 300; ¹H-NMR (500 MHz, DMSO-d6) δ ppm 10.51 (br. s., 1H), 8.28 (br. s., 1H), 8.03 (s, 1H), 7.74 (s, 1H), 7.55 (d, 2H), 7.26 (t, 2H), 7.07-7.12 (m, 2H), 7.04 (d, 2H), 4.63 (dd, 1H), 4.31 (dd, 1H), 2.26-2.43 (m, 2H), 2.11-2.21 (m, 1H), 1.96-2.11 (m, 1H). |
| E14 | D23 | 4-cyanophenoxy | R_t (HPLC) 3.31 min. MS: (ES/+) 308 m/z: [MH⁺]. C18H17N3O2 requires 307. |
| E15 | D24 | phenoxy | R_t (HPLC) 3.45 min; MS: (ES/+) 283 m/z: [MH⁺]. C17H18N3O2 requires 282. 1H NMR (500 MHz, DMSO-d6) δ (ppm): 10.23 (br. s., 1H), 8.22 (br. s., 1H), 7.95-8.07 (m, 1H), 7.74 (s, 1H), 7.56 (d, 2H), 7.41 (t, 2H), 7.18 (t, 1H), 7.08 (d, 2H), 7.02 (d, 2H), 4.63 (dd, 1H), 4.30 (dd, 1H), 2.27-2.44 (m, 2H), 2.11-2.22 (m, 1H), 1.96-2.12 (m, 1H). |
| E16 | D25 | 3-fluorophenoxy | R_t (HPLC) 3.61 min. MS: (ES/+) 301 m/z: [MH⁺]. C17H17FN2O2 requires 336. ¹H-NMR (400 MHz, DMSO-d₆) δ (ppm): 1.98-2.11 (m, 1H); 2.11-2.22 (m, 1H); 2.28-2.42 (m, 2H); 4.27-4.35 (m, 1H); 4.61-4.70 (m, 1H); 6.85 (d, 1H); 6.88 (dd, 1H); 7.00 (t, 1H); 7.14 (d, 2H); 7.44 (dd, 1H); 7.58 (d, 2H); 7.73 (s, 1H); 8.02 (s, 1H); 8.25 (br. s., 1H); 10.40 (br. s., 1H). |
| E17 | D26 | 2-cyanophenoxy | R_t (HPLC) 3.21 min. MS: (ES/+) m/z: 308 [MH⁺]. C17H17FN2O2 requires 336. 1H NMR (500 MHz, DMSO-d6) δ (ppm): 10.63 (br. s., 1H), 8.36 (br. s., 1H), 8.03-8.11 (m, 1H), 7.93 (dd, 1H), 7.76 (s, 1H), 7.71 (dt, 1H), 7.64 (d, 2H), 7.34 (t, 1H), 7.23 (d, 2H), 7.01 (d, 1H), 4.63-4.75 (m, 1H), 4.29-4.37 (m, 1H), 2.31-2.43 (m, 2H), 2.11-2.22 (m, 1H), 1.99-2.12 (m, 1H). |

The hydrochloride salts of the following compounds of formula (Ig) were prepared by a similar procedure to that used for Example 5, procedure 1. For each compound, reference to a starting material is provided. This is provided merely for assistance to the skilled chemist. The starting material may not necessarily have been prepared from the batch referred to.

(Ig)

| No. | SM | $R^6$ | Characterization |
|---|---|---|---|
| E18 | D29 | benzoxy | Rt (HPLC): 3.49 min. MS: (ES/+) m/z: 297 [MH+]: C18H20N2O2 requires 296. $^1$H NMR (500 MHz, DMSO-d6) δ (ppm): 9.39-9.14 (br. s., 2H), 8.01 (s, 1H), 7.67 (s, 1H), 7.48 (d, 2H), 7.46-7.42 (m, 2H), 7.38 (t, 2H), 7.34-7.29 (m, 1H), 7.06 (d, 2H), 5.13 (s, 2H), 4.61 (dd, 1H), 4.31 (t, 1H), 2.57-2.46 (m, 1H), 2.37-2.26 (m, 1H), 2.16-2.03 (m, 1H), 1.99-1.88 (m, 1H). |
| E19 | D31 | 2-fluorobenzoxy | Rt (HPLC): 3.54 min; Chiral HPLC. Column: chiralpak AD-H 5 um, 250 × 4.6 mm Mobile phase: A: n-Hexane; B: Isopropanol. Gradient: isocratic 30% B. Flow rate: 0.8 ml/min. UV wavelength range: 200-400 nm. Analysis time: 15 min. ret. time: 10.4 min; MS: (ES/+) m/z: 315 [MH$^+$]. C18H19FN2O2 requires 314; 1H NMR (500 MHz, DMSO-d6) δ (ppm): 9.37-9.13 (br. s., 2H), 8.01 (s, 1H), 7.68 (s, 1H), 7.55 (t, 1H), 7.49 (d, 2H), 7.45-7.37 (m, 1H), 7.29-7.20 (m, 2H), 7.08 (d, 2H), 5.17 (s, 2H), 4.62 (dd, 1H), 4.31 (t, 1H), 2.59-2.50 (m, 1H), 2.37-2.26 (m, 1H), 2.18-2.03 (m, 1H), 2.01-1.88 (m, 1H). |

Example 20

(5S)-5-{4-[(Phenylmethyl)oxy]phenyl}-D-prolinamide hydrochloride (E20)

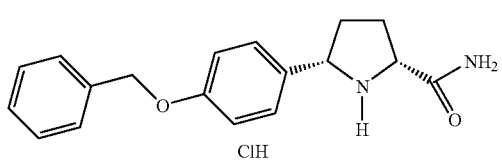

To a solution of 1,1-dimethylethyl (2R,5S)-2-(aminocarbonyl)-5-{4-[(phenylmethyl)oxy]phenyl}-1-pyrrolidinecarboxylate (D38, 50 mg, 0.126 mmol) in a mixture of ethyl acetate (0.9 ml) and methanol (0.1 ml) was added acetylchloride (50 µl, 0.63 mmol) at 0° C. The mixture was shaken for 2 h and slowly allowed to warm to room temperature. After evaporating the solvent, the residue was triturated with diethyl ether to afford the title compound as a white solid (35 mg, 85%); R$_t$ (HPLC): 3.55 min; MS: (ES/+) m/z: 297 [MH+], C18H20N2O2 requires 296; $^1$H NMR (400 MHz, DMSO-d6) δ (ppm): 10.50 (bs, 1H); 8.15 (bs, 1H); 8.05 (s, 1H); 7.73 (s, 1H); 7.42-7.49 (m, 4H); 7.40 (t, 2H); 7.30-7.36 (m, 1H); 7.08 (d, 2H); 5.15 (s, 2H); 4.60 (dd, 1H); 4.30 (dd, 1H); 2.23-2.40 (m, 2H); 2.10-2.20 (m, 1H); 1.95-2.08 (m, 1H).

Example 21

(5S)-5-(4-{[(2-fluorophenyl)methyl]oxy}phenyl)-D-prolinamide hydrochloride (E21)

Example 22

(5R)-5-(4-{[(2-fluorophenyl)methyl]oxy}phenyl)-D-prolinamide hydrochloride (E22)

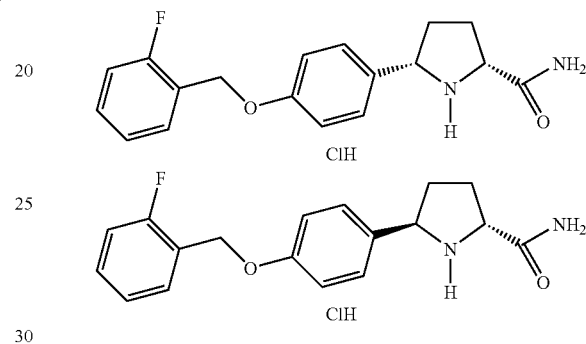

To a solution of 1,1-dimethylethyl (2R,5S)-2-(aminocarbonyl)-5-(4-{[(2-fluorophenyl)methyl]oxy}phenyl)-1-pyrrolidinecarboxylate (D40, 145 mg, 0.37 mmol) in DCM (6 ml) was added TFA (1.5 ml) dropwise at 0° C. The mixture was stirred for 1 h under these conditions. After evaporating the solvent, the resulting crude material was purified by SCX cartridge, to afford the title compound (100 mg, 92%) as a mixture of diastereoisomers. The diastereoisomers were separated via chiral semipreparative HPLC: Column: chiralpak AD-H; Mobile phase: n-Hexane:Ethanol=70/30; Flow rate: 13 ml/min; UV wavelength range: 225 nm; Analysis time: 25 min. Analytical chromatographic conditions: Chiral HPLC: Column: chiralpak AD-H 5 um, 250×4.6 mm; Mobile phase: A: n-Hexane; B: Ethanol; Gradient: isocratic 30% B; Flow rate: 0.8 ml/min; UV wavelength range: 200-400 nm; Analysis time: 30 min; R$_t$: 14.02 min (E21); R$_t$: 16.12 min (E20)

E21 (69.5 mg): R$_t$ (HPLC): 3.60 min. Chiral HPLC: Column: chiralcel OD 10 um, 250×4.6 mm; Mobile phase: A: n-Hexane; B: Ethanol; Gradient: isocratic 30% B; Flow rate: 0.8 ml/min; UV wavelength range: 200400 nm; Analysis time: 22 min; R$_t$: 17.6 min. [α]$_D$=+30.6°. $^1$H-NMR (400 MHz, DMSO-d$_6$) δ (ppm): 10.19 (br.s., 1H); 8.13 (br.s., 1H); 7.94 (s, 1H); 7.60-7.77 (m, 1H); 7.51 (dt, 1H); 7.43 (d, 2H); 7.34-7.41 (m, 1H); 7.23 d, 1H); 7.18 (dd, 1H); 7.05 (d, 2H); 5.13 (s, 2H); 4.49-4.60 (m, 1H); 4.19-4.28 (m, 1H); 2.17-2.38 (m, 1H); 2.05-2.16 (m, 1H); 1.92-2.03 (m, 1H).

E22 (32 mg): R$_t$ (HPLC): 3.55 min. Chiral HPLC: Column: chiralpak AD-H 5 um, 250×4.6 mm; Mobile phase: A: n-Hexane; B: Isopropanol; Gradient: isocratic 30% B; Flow rate: 0.8 ml/min; UV wavelength range: 200-400 nm; Analysis time: 15 min; R$_t$: 8.4 min. $^1$H-NMR (400 MHz, DMSO-d$_6$) δ (ppm): 9.25 (br.s., 2H); 8.01 (s, 1H); 7.68 (s, 1H); 7.55 (t, 1H); 7.49 (d, 2H); 7.37-7.45 (m, 1H); 7.20-7.29 (m, 2H); 7.08 (d, 2H); 5.17 (s, 2H); 4.62 (dd, 1H); 4.31 (t, 1H); 2.50-2.59 (m, 1H); 2.26-2.37 (m, 1H); 2.03-2.18 m, 1H); 1.88-2.01 (m, 1H).

Example 23

(5R)-5-(2-fluoro-4-{[(2-fluorophenyl)methyl]oxy}phenyl)-L-prolinamide hydrochloride (E23)

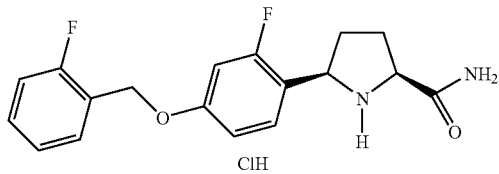

To a solution of 1,1-dimethylethyl (2S,5R)-2-(aminocarbonyl)-5-(2-fluoro-4-{[(2-fluorophenyl)methyl]oxy}phenyl)-1-pyrrolidinecarboxylate (D47, 130 mg, 0.300 mmol) in a mixture of ethyl acetate (2.3 ml) and methanol (0.230 ml) was added acetyl chloride (64 µl, 2.5 eq) at 0° C. The mixture was shaken for 2 h and slowly allowed to warm to room temperature. After evaporating the solvent, the residue was triturated with diethyl ether to afford the title compound as a white solid (101 mg, 92%); $R_t$ (HPLC): 3.66 min; MS: (ES/+) m/z: 333 [MH+], C18H18F2N2O2 requires 332; $^1$H NMR (400 MHz, DMSO-d6) δ (ppm): 10.36 (br. s., 1H), 8.35 (br. s., 1H), 8.04 (s, 1H), 7.72 (s, 1H), 7.51-7.64 (m, 2H), 7.40-7.49 (m, 1H), 7.20-7.32 (m, 2H), 7.05 (dd, 1H), 6.98 (dd, 1H), 5.19 (s, 2H), 4.81 (dd, 1H), 4.31 (dd, 1H), 2.22-2.42 (m, 2H), 2.01-2.22 (m, 2H).

Example 24

(5R)-5-{3-[(phenylmethyl)oxy]phenyl}-L-prolinamide hydrochloride (E24)

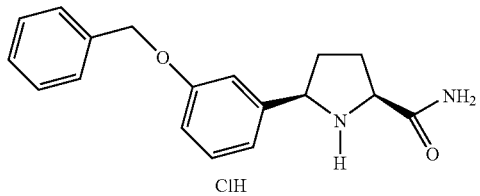

To a solution of 1,1-dimethylethyl (2S,5R)-2-(aminocarbonyl)-5-{3-[(phenylmethyl)oxy]phenyl}-1-pyrrolidinecarboxylate (D54, 142 mg, 0.358 mmol) in a mixture of ethyl acetate (2.3 ml) and methanol (0.23 ml) was added acetyl chloride (64 µl, 2.5 eq) at 0° C. The mixture was shaken for 1.5 h and slowly allowed to warm to room temperature. After evaporating the solvent, the residue was triturated with diethyl ether to afford the title compound as a white solid (71 mg, 60%); $R_t$ (HPLC): 3.51 min. MS: (ES/+) m/z: 297 [MH+], C18H20N2O2 requires 296; $^1$H NMR (400 MHz, DMSO-d6) δ (ppm): 10.52 (br. s., 1H), 8.41 (br. s., 1H), 8.03 (s, 1H), 7.73 (s, 1H), 7.31-7.50 (m, 6H), 7.26 (t, 1H), 7.10 (d, 1H), 7.06 (dd, 1H), 5.13 (s, 2H), 4.62 (dd, 1H), 4.32 (dd, 1H), 2.24-2.44 (m, 2H), 2.09-2.23 (m, 1H), 1.93-2.09 (m, 1H).

Example 25

(5R)-5-[4-{[(2-fluorophenyl)methyl]oxy}-3-(methyloxy)phenyl]-L-prolinamide hydrochloride (E25)

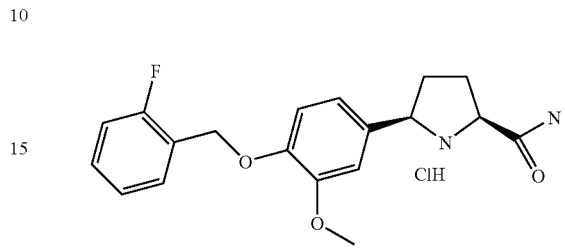

The title compound was synthesized via an analogous procedure to that described as procedure 2 for example 4 using methyl (5R)-5-[4-{[(2-fluorophenyl)methyl]oxy}-3-(methyloxy)phenyl]-L-prolinate (D62, 95 mg, 0.264 mmol). The free base was purified via flash chromatography using dichloromethane with MeOH (2% to 20%) and converted as described in example 4 by procedure 2 into the hydrochloric salt. MS: (ES/+) m/z: 344 [MH+], C19H21FN2O3 requires 344. $^1$H NMR (300 MHz, DMSO-d$_6$) δ ppm: 9.79 (br. s., 2H), 7.96 (s, 1H), 7.71 (s, 1H), 7.55 (t, 1H), 7.42 (q, 1H), 7.19-7.33 (m, 3H), 7.12 (d, 1H), 7.01 (d, 1H), 5.13 (s, 2H), 4.49-4.62 (m, 1H), 4.20-4.30 (m, 1H), 3.78 (s, 3H), 1.91-2.45 (m, 4H).

Example 26

(5R)-5-(4-{[(2-fluorophenyl)methyl]amino}phenyl)-L-prolinamide hydrochloride (E26)

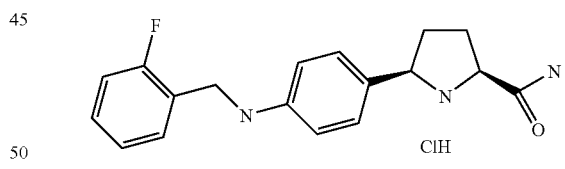

The title compound was synthesized via an analogous procedure to that described as procedure 2 for example 5 using Methyl (5R)-5-(4-{[(2-fluorophenyl)methyl]amino}phenyl)-L-prolinate (D68, 36 mg, 0.109 mmol). The free base was purified via flash chromatography using dichloromethane with MeOH (2% to 20%) and converted as described in example 4 by procedure 2 into the hydrochloric salt. MS: (ES/+) m/z: 314 [MH+], C18H20FN3O requires 313; $^1$H NMR (300 MHz, DMSO-d6) δ ppm 10.17-10.32 (m, 1H), 8.02 (s, 1H), 7.77-7.91 (m, 1H), 7.72 (s, 1H), 7.35-7.45 (m, 1H), 7.27-7.33 (m, 1H), 7.24 (d, 2H), 7.12-7.23 (m, 2H), 6.65 (d, 2H), 4.40-4.55 (m, 1H), 4.35 (s, 2H), 4.20-4.31 (m, 1H), 2.26-2.42 (m, 1H), 2.09-2.25 (m, 2H), 1.91-2.08 (m, 1H)

Example 27

(5R)-5-(3-cyano-4-{[(2-fluorophenyl)methyl]oxy}phenyl)-L-prolinamide hydrochloride (E27)

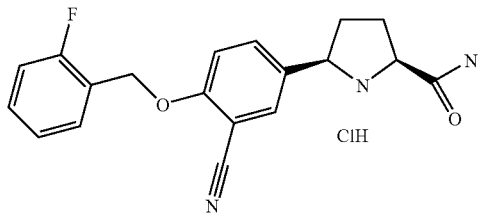

A solution of methyl (5R)-5-(3-cyano-4-{[(2-fluorophenyl)methyl]oxy}phenyl)-L-prolinate (D73, 64 mg, 0.180 mmol) in 7M NH3/MeOH (2 ml) was stirred 10.5 h at 40° C. The solvent was evaporated and the residue purified via flash chromatography using a DCM/MeOH (98:2 to 8:2) to afford (5R)-5-(3-cyano-4-{[(2-fluorophenyl)methyl]oxy}phenyl)-L-prolinamide (44 mg, 72%) as the free base. The title compound (32 mg) was prepared as described for example 4 in procedure 2. MS: (ES/+) m/z: 340 [MH+], C19H18FN3O2 requires 339. $^1$H NMR (300 MHz, DMSO-d6) δ ppm 10.37 (br. s., 1H), 8.54 (br. s., 1H), 8.04 (br. s., 1H), 7.97 (dd, 1H), 7.85 (dd, 1H), 7.74 (br. s., 1H), 7.63 (td, 1H), 7.50 (d, 1H), 7.43-7.55 (m, 1H), 7.25-7.36 (m, 2H), 5.32-5.44 (m, 2H), 4.56-4.82 (m, 1H), 4.21-4.42 (m, 1H), 2.22-2.43 (m, 2H), 1.94-2.26 (m, 2H).

Example 28

(5R)-5-[4-(2-phenylethyl)phenyl]-L-prolinamide hydrochloride (E28)

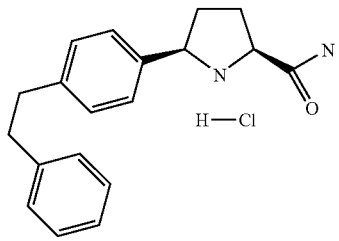

To a suspension of (5R)-5-[4-(2-phenylethyl)phenyl]-L-prolinamide (D81, 30 mg, 0.1 mmol) in diethyl ether (2 ml) was added hydrochloric acid (1N in Et2O, 150 μl) and the mixture was triturated. The solvent was removed under vacuum affording the title compound as a white solid (30 mg, 91%). R$_t$ (HPLC): 3.81 min; MS: (ES/+) m/z: 295 [MH]+ C19H22N2O requires 294; $^1$H NMR (500 MHz, DMSO-d$_6$) δ (ppm): 8.15-8.98 (br.s, 2H); 8.01 (s, 1H); 7.71 (s, 1H); 7.43 (d, 2H); 7.30 (d, 2H); 7.26 (d, 2H); 7.24 (t, 2H); 7.17 (t, 1H); 4.51-4.65 (m, 1H); 4.23-4.33 (m, 1H); 2.81-2.95 (m, 4H); 2.25-2.39 (m, 2H); 2.08-2.20 (m, 1H); 1.92-2.06 (m, 1H).

Example 29

(5R)-5-(5-{[(2-fluorophenyl)methyl]oxy}-2-pyridinyl)-L-prolinamide hydrochloride (E29)

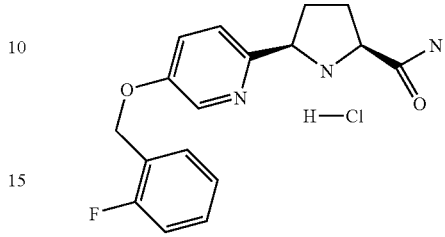

Methyl (5R)-5-(5-{[(2-fluorophenyl)methyl]oxy}-2-pyridinyl)-L-prolinate (D86, 50 mg) was dissolved in ammonia 7M in methanol (2 ml) and the mixture was stirred overnight at room temperature. The solvent was removed under vacuum; the residue was dissolved in diethyl ether (1 ml) and hydrochloric acid (0.35 ml, 1M solution in Et2O) was added. The suspension was triturated and the solvent removed affording the title compound as a white solid (38 mg, 72%). R$_t$ (HPLC): 3.34 min; MS: (ES/+) m/z: 316 [MH]+ C17H18FN3O2 requires 315; $^1$H NMR (500 MHz, DMSO-d$_6$) δ (ppm): 10.43-10.64 (m, 1H); 8.37 (d, 1H); 8.29-8.41 (m, 1H); 8.00-8.06 (m, 1H); 7.72-7.77 (m, 1H); 7.59 (dd, 1H); 7.54 (t, 1H); 7.46 (t, 1H); 7.36-7.44 (m, 1H); 7.18-7.26 (m, 2H); 5.21 (s, 2H); 7.71-4.89 (m, 1H); 4.20-4.37 (m, 1H); 2.25-2.45 (m, 2H); 1.91-2.09 (m, 1H); 1.67-1.89 (m, 1H).

Example 30 rac-(2R,3aR,6aR)-2-(4-{[2-fluorophenyl)methyl]oxy}phenyl)hexahydropyrrolo[3,4-b]pyrrol-6(1H)-one hydrochloride (E30)

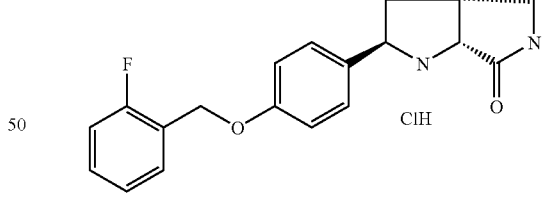

rac-(2R,3aR,6aR)-2-(4-{[(2-fluorophenyl)methyl]oxy}phenyl)-1-(phenylmethyl)hexahydropyrrolo[3,4-b]pyrrol-6(1H)-one (D94, 42 mg, 0.1 mmol) was dissolved in dry MeOH (12 ml), some drops of AcOH and 42 mg of Pd/C (10%) was added and the solution was stirred at room temperature under 1 atm of hydrogen overnight. The solvent was evaporated and the residue purified by mass directed preparative HPLC to give the free base of the title compound (15 mg). The free base was converted into the hydrochloric salt via an analogous procedure to that described hereinabove to give the title compound.

Example 31

(5R)-5-(4-{[(2-fluorophenyl)methyl]oxy}phenyl)-N-methyl-L-prolinamide hydrochloride (E31)

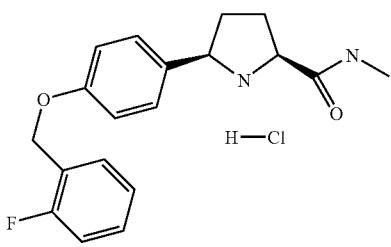

To a solution of 1,1-dimethylethyl (2R,5S)-2-(4-{[(2-fluorophenyl)methyl]oxy}phenyl)-5-[(methylamino)carbonyl]-1-pyrrolidinecarboxylate (D96, 40 mg, 0.09 mmol) in ethyl acetate (0.9 ml) and methanol (0.1 ml) at 0° C. was added AcCl (40 μl, 0.56 mmol) and the mixture was stirred for two hours at room temperature. The solvent was removed under nitrogen flow and the residue triturated with Et$_2$O. The solvent was removed to afford the title compound as a white solid (28 mg, 85%). R$_t$ (HPLC): 3.74 min; MS: (ES/+) m/z: 329-[MH+] C$_{19}$H$_{21}$FN2O$_2$ requires 328; $^1$H NMR (500 MHz, DMSO-d$_6$) δ (ppm): 10.03-10.78 (br.s, 1H); 8.56 (q, 1H); 7.95-8.46 (br.s, 1H); 7.55 (dt, 1H); 7.49 (d, 2H); 7.39-7.46 (m, 1H); 7.20-7.29 (m, 2H); 7.09 (d, 2H); 5.16 (s, 2H); 4.58 (dd, 1H); 4.28 (dd, 1H); 2.70 (d, 3H); 2.21-2.37 (m, 2H); 1.98-2.17 (m, 2H).

Example 32

(5R)-5-(4-{[(2-fluorophenyl)methyl]oxy}phenyl)-N,N-dimethyl-L-prolinamide hydrochloride (E32)

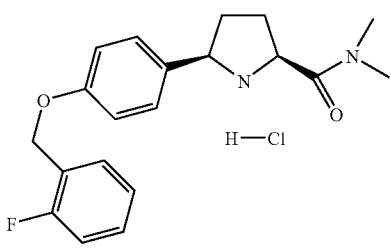

To a solution of the mixture D95 (20 mg) in N,N-dimethylformamide at 0° C. was added sodium hydride (10.0 mg, 0.25 mmol, 60% dispersion in mineral oil) and the mixture was stirred for 10 min at the same temperature. Methyl iodide (20 μl, 0.3 mmol) was added and the mixture was stirred for one hour at room temperature. The reaction was quenched with water and extracted with ethyl acetate. The organic layer was washed with ice cold brine, dried (Na$_2$SO$_4$) and evaporated. The residue was purified by chromatography on silica gel affording the title compound as a white solid (16 mg). This residue was dissolved in ethyl acetate (0.45 ml) and methanol (0.05 ml) at 0° C. was added AcCl (16 μl) and the mixture was stirred for two hours at room temperature. The solvent was removed under nitrogen flow and the residue triturated with Et$_2$O. The solvent was removed to afford the title compound as a white solid (10 mg, 85%). R$_t$ (HPLC): 3.84 min; MS: (ES/+) m/z: 343 [MH]+ C$_{20}$H$_{23}$FN2O$_2$ requires 342; $^1$H NMR (500 MHz, DMSO-d$_6$) δ (ppm): the broad signals of the acid protons in the range between 7.50 and 11.50; 7.55 (dt, 1H); 7.49 (d, 2H); 7.39-7.46 (m, 1H); 7.21-7.29 (m, 2H); 7.10 (d, 2H); 5.18 (s, 2H); 4.68-4.79 (m, 1H); 4.52-4.65 (m, 1H); 3.04 (s, 3H); 2.92 (s, 3H); 1.90-2.48 (m, 4H).

Example 33

(5R)-5-(4-{[(2-fluorophenyl)methyl]oxy}phenyl)-L-prolinamide methanesulfonate (E33)

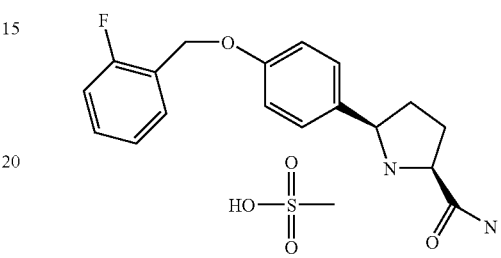

EtOAc (6 ml) was added to (5R)-5-(4-{[(2-Fluorophenyl)methyl]oxy}phenyl)-L-prolinamide (E4, 300 mg) and this was heated at 60° C. for an hour to dissolve the compound. Then methanesulfonic acid (65 μl, 1.05 eq) was added to the solution and as soon as the acid was added, the solution went cloudy. This was then left to temperature cycle (0-40° C.) for 2 days. The compound was isolated by filtration as a white solid, washed with EtOAc and dried in vacuo at 40° C. overweek-end to afford 335 mg of the title compound.

Melting point: 192° C.

Biological Assay

Na Channel Assay Protocol

The ability of the compounds of the invention to modulate the voltage-gated sodium channel subtype NaV 1.3 may be determined by the following assay.

Cell Biology

Stable cell lines expressing hNaV1.3 channels were created by transfecting CHO cells with the pCIN5-hNav1.3 vector using the lipofectamine (Invitrogen) transfection method. pCIN5 is a bicistronic vector for the creation of mammalian cell lines that predisposes all neomycin resistant cells to express recombinant protein (see Rees S., Coote J., Stable J., Goodson S., Harris S. & Lee M. G. (1996) Biotechniques, 20, 102-112) by virtue of the recombinant cDNA being linked to the neomycin-selectable marker cDNA downstream of the CMV promoter (for full details see Chen Y H, Dale T J, Romanos M A, Whitaker W R, Xie X M, Clare J J. Cloning, distribution and functional analysis of the type III sodium channel from human brain Eur J Neurosci, 2000 December; 12, 4281-9). Cells were cultured in Iscove's modified Dulbecco's medium (Invitrogen) containing, 10% fetal bovine serum, 1% L-glutamine, 1% Penicillin-Streptomycin (Invitrogen), 1% non-essential amino acids, 2% H-T supplement and 1% G418 (Invitrogen) and maintained at 37° C. in a humidified environment containing 5% CO2 in air. Cells were liberated from the T175 culture flask for passage and harvesting using Versene (Invitrogen).

Cell Preparation

Cells were grown to 60-95% confluence in a T75 flask. Cells were lifted by removing the growth media and incubating with 1.5 ml of warmed (37° C.) Versene (Invitrogen, 15040-066) for 6 min. Lifted cells were suspended in 10 ml of PBS (Invitrogen, 14040-133). Cell suspension was then placed into a 10-ml centrifuge tube and centrifuged for 2 min at 700 rpm. After centrifugation, the supernatant was removed and the cell pellet was resuspended in 3 ml of PBS.

Electrophysiology

Currents were recorded at room temperature (21-23° C.) using the IonWorksHT planar array electrophysiology technology (Molecular Devices Corp.). Stimulation protocols and data acquisition were carried out using a microcomputer (Dell Pentium 4). In order to determine planar electrode hole resistances (Rp), a 10 mV, 160 ms potential difference was applied across each hole. These measurements were performed before cell addition. After cell addition a seal test was performed prior to antibiotic (amphotericin) circulation to achieve intracellular access. Leak subtraction was conducted in all experiments by applying a 160 ms hyperpolarizing (10 mV) prepulse 200 ms before the test pulses to measure leak conductance. Test pulses stepping from the holding potential of −90 mV to 0 mV were applied for 20 ms and repeated 10 times at a frequency of 10 Hz. In all experiments, the test pulse protocol was performed in the absence (pre-read) and presence (post-read) of a compound. Pre- and post-reads were separated by a compound addition followed by a 3-3.5 min incubation.

Solutions and Drugs

The intracellular solution contained the following (in mM): K-gluconate 100, KCl 40 mM, MgCl2 3.2, EGTA 3, HEPES 5, adjusted to pH 7.25. Amphotericin was prepared as 30 mg/ml stock solution and diluted to a final working concentration of 0.1 mg/ml in internal buffer solution. The external solution was Dulbecco's PBS (Invitrogen) and contained the following (in mM): CaCl2 0.90, KCl 2.67, K3PO4 1.47, MgCl2 0.50, NaCl 138, Na3PO4 8.10, with a pH of 7.4. Compounds were prepared in DMSO as 10 mM stock solutions and subsequent 1:3 serial dilutions performed. Finally the compounds were diluted 1:100 in external solution resulting in a final DMSO concentration of 1%.

Data Analysis

The recordings were analysed and filtered using both seal resistance (>40 MΩ) and peak current amplitude (>200 pA) in the absence of compound to eliminate unsuitable cells from further analysis. Paired comparisons between pre-drug and post-drug additions were used to determine the inhibitory effect of each compound. The concentrations of compounds required to inhibit current elicited by the $1^{st}$ depolarising pulse by 50% (tonic pIC50) were determined by fitting of the Hill equation to the concentration response data. In addition the use-dependent inhibitory properties of the compounds were determined by assessing the effect of compounds on the $10^{th}$ versus $1^{st}$ depolarising pulse. The ratio of the $10^{th}$ over $1^{st}$ pulse was calculated in the absence and presence of drug and the % use-dependent inhibition calculated. The data was fitted using the same equation as for the tonic pIC50 and the concentration producing 15% inhibition (use-dependent $pUD_{15}$) calculated.

The compounds of Examples 1 to 3 and 5 to 32 were tested in the above assay and gave $pUD_{15}$ values of 4.5 or greater.

Monoamine Oxidase-B Assay Protocol

The protocol describes the assay for testing MAO-B inhibition. It is a fluorescence-based end-point assay using benzylamine as substrate. Oxidation of the substrate by MAO-B leads to hydrogen peroxide release, and this product is then utilised by peroxidase to convert non-fluorescent Amplex Red™ into fluorescent resorufin. The global reaction is:

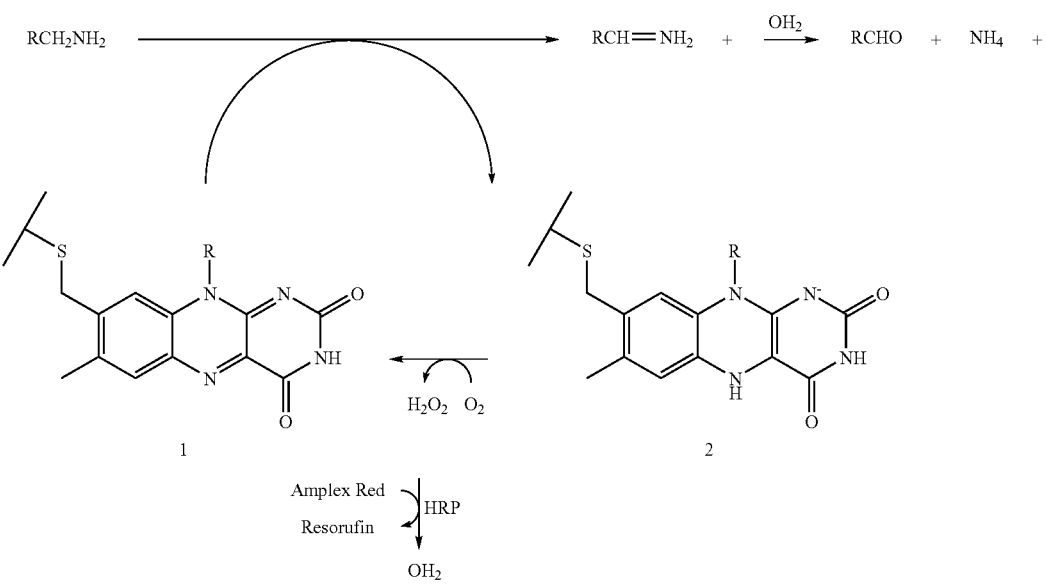

Thus inhibition of the enzyme by a test compounds leads to reduced fluorescence.

The assay uses human recombinant monoamine oxidase B that is present in microsomes from baculovirus infected insect cells (Supplied by Sigma). Compounds are tested over a range of concentrations in order to determine the concentration that causes half-maximal inhibition of the enzyme activity in the assay (IC50): Pargyline (Sigma) is used as a positive control in the assay, giving an IC50 in the range 0.4-2 μM.

Dispense 0.1 µl of test compound in neat DMSO in black low volume Greiner 384-well plate. Add 5 µl of substrate solution (400 µM benzylamine (Sigma), 50 µM Amplex Red (Molecular Probes), 50 mM potassium phosphate, pH 7.4). Add 5 µl of the assay buffer (50 mM potassium phosphate, pH 7.4) to blank wells, Add 5 µl of the enzyme solution (0.23 IU/ml human recombinant monoamine oxidase B, 1 IU/ml horseradish peroxidase type XII (Sigma), 50 mM potassium phosphate, pH 7.4) to remaining wells. Shake to ensure proper mixing. Incubate for 60 minutes at room temperature in darkness. Read fluorescence using Analyst/Gemini (Molecular Devices; Resorufin: Ex530/Em580/Dichr561 (Analyst)–Ex555/Em590/Cutoff570 (Gemini)).

The effect of a given compound is calculated as:

% Inh=100×[(data−control1)/(control2−control1)], where control1 corresponds to the enzyme showing its maximum activity (i.e., not inhibited) and control2 corresponds to minus enzyme fluorescence in absence of HRP.

The invention claimed is:

1. A compound of formula (I), or a pharmaceutically acceptable salt thereof

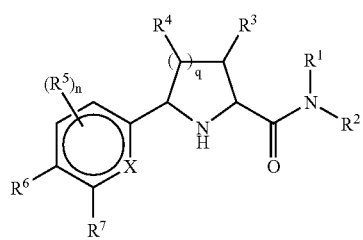

wherein
$R^1$ and $R^2$ are independently hydrogen, $C_{1-6}$alkyl or $C_{3-6}$cycloalkyl$C_{1-6}$alkyl; or such $R^1$ and $R^2$, together with the nitrogen to which they are attached, form an unsubstituted 3-, 4-, 5- or 6-membered saturated ring;
q is 1 or 2;
$R^3$ and $R^4$ are hydrogen; or when q is 1, $R^3$ and $R^4$, together with the interconnecting atoms, form a cyclopropane ring; or such $R^3$ and $R^1$, together with the interconnecting atoms form a saturated or unsaturated 5- to 6-membered ring;
X is carbon or nitrogen;
n is 0, 1 or 2, wherein when present each $R^5$ is independently selected from $C_{1-3}$alkyl, halogen, cyano, halo$C_{1-3}$alkyl, hydroxy, $C_{1-3}$alkoxy and $C_{1-3}$haloalkoxy;
either $R^6$ or $R^7$ is —O—$R^8$, —OCHR$^9$R$^8$, NCH$_2$R$^8$ or (CH$_2$)$_2$R$^8$ and the other $R^6$ or $R^7$ is hydrogen or $R^5$; wherein $R^8$ is a phenyl ring optionally substituted by one or more groups independently selected from $C_{1-3}$alkyl, halogen, cyano, halo$C_{1-3}$alkyl, hydroxy, $C_{1-3}$alkoxy and $C_{1-3}$haloalkoxy; and
$R^9$ is hydrogen or $C_{1-3}$alkyl.

2. A compound according to claim 1 wherein X is C.
3. A compound according to claim 1 wherein q is 1.
4. A compound according to claim 1 wherein $R^6$ is —O—$R^8$ or —OCHR$^9$R$^8$, and $R^7$ is hydrogen or $R^5$; and wherein $R^8$ is a phenyl ring optionally substituted by one or more groups independently selected from $C_{1-3}$alkyl, halogen, cyano, halo$C_{1-3}$alkyl, hydroxy, $C_{1-3}$alkoxy and $C_{1-3}$haloalkoxy.
5. A compound according to claim 1, wherein $R^3$ and $R^4$ are hydrogen.
6. A compound according to claim 1 wherein $R^3$ and $R^1$, together with the interconnecting atoms form a saturated or unsaturated 5-membered ring.
7. A compound selected from:
(2S,6R)-6-(4-{[(3-fluorophenyl)methyl]oxy}phenyl)-2-piperidinecarboxamide;
(2R,6S)-6-(4-{[(3-fluorophenyl)methyl]oxy}phenyl)-2-piperidinecarboxamide;
(5R)-5-{4-[(phenylmethyl)oxy]phenyl}-L-prolinamide;
(5R)-5-(4-{[(3-fluorophenyl)methyl]oxy}phenyl)-L-prolinamide;
(5R)-5-(4-{[(3-cyanophenyl)methyl]oxy}phenyl)-L-prolinamide;
(5R)-5-(4-{[(4-fluorophenyl)methyl]oxy}phenyl)-L-prolinamide;
(5R)-5-(4-{[(2-cyanophenyl)methyl]oxy}phenyl)-L-prolinamide;
(5R)-5-(4-{[(4-cyanophenyl)methyl]oxy}phenyl)-L-prolinamide;
(5R)-5-{-4-[({2-[(trifluoromethyl)oxy]phenyl}methyl)oxy]phenyl}-L-prolinamide;
(5R)-5-(4-{[(1R)-1-phenylethyl]oxy}phenyl)-L-prolinamide;
(5R)-5-{4-[(4-fluorophenyl)oxy]phenyl}-L-prolinamide;
(5R)-5-{4-[(4-cyanophenyl)oxy]phenyl}-L-prolinamide;
(5R)-5-[4-(phenyloxy)phenyl]-L-prolinamide;
(5R)-5-{4-[(3-fluorophenyl)oxy]phenyl}-L-prolinamide;
(5R)-5-{4-[(2-cyanophenyl)oxy]phenyl}-L-prolinamide;
(5S)-5-{4-[(phenylmethyl)oxy]phenyl}-L-prolinamide;
(5S)-5-{4-[(phenylmethyl)oxy]phenyl}-D-prolinamide;
(5R)-5-(2-fluoro-4-{[(2-fluorophenyl)methyl]oxy}phenyl)-L-prolinamide;
(5R)-5-{3-[(phenylmethyl)oxy]phenyl}-L-prolinamide;
(5R)-5-[4-{[(2-fluorophenyl)methyl]oxy}-3-(methyloxy)phenyl]-L-prolinamide;
(5R)-5-(4-{[(2-fluorophenyl)methyl]amino}phenyl)-L-prolinamide;
(5R)-5-(3-cyano-4-{[(2-fluorophenyl)methyl]oxy}phenyl)-L-prolinamide;
(5R)-5-[4-(2-phenylethyl)phenyl]-L-prolinamide;
(5R)-5-(5-{[(2-fluorophenyl)methyl]oxy}-2-pyridinyl)-L-prolinamide;
(2S,3aS,6aS)-2-(4-{[(2-fluorophenyl)methyl]oxy}phenyl)hexahydropyrrolo[3,4-b]pyrrol-6(1H)-one;
(5R)-5-(4-{[(2-fluorophenyl)methyl]oxy}phenyl)-N-methyl-L-prolinamide;
(5R)-5-(4-{[(2-fluorophenyl)methyl]oxy}phenyl)-N,N-dimethyl-L-prolinamide;
and pharmaceutically acceptable salts thereof.

8. A pharmaceutical composition comprising a compound as claimed in claim 1 and a pharmaceutically acceptable carrier therefor.

9. A method of treating depression or a mood disorder in a mammal comprising administering an effective amount of a compound according to claim 1.

10. A method of treating a bipolar disorder in a mammal comprising administering an effective amount of a compound according to claim 1.

11. A method according to claim 9 wherein the mammal is human.

12. A method according to claim 10 wherein the mammal is human.

13. A method of treating compulsive eating disorder or binge eating disorder in a mammal comprising administering an effective amount of a compound according to claim 1.

14. A method according to claim 13 wherein the mammal is human.

15. A method of treating epilepsy in a mammal comprising administering an effective amount of a compound according to claim 1.

16. A method according to claim 15 wherein the mammal is human.

* * * * *